(12) United States Patent (10) Patent No.: US 9,273,316 B2
Primiano et al. (45) Date of Patent: Mar. 1, 2016

(54) REAGENTS AND METHODS FOR TREATING CANCER

(75) Inventors: Thomas Primiano, Monona, WI (US); Lonnie Bookbinder, Corvallis, MT (US); Bey-Dih Chang, Madison, WI (US); Jeremy Heidel, Madison, WI (US)

(73) Assignee: PeptiMed, Inc., Madison, WI (US)

( * ) Notice: Subject to any disclaimer, the term of this patent is extended or adjusted under 35 U.S.C. 154(b) by 0 days.

(21) Appl. No.: 13/113,963

(22) Filed: May 23, 2011

(65) Prior Publication Data

US 2011/0293698 A1 Dec. 1, 2011

Related U.S. Application Data

(60) Provisional application No. 61/347,104, filed on May 21, 2010.

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC ........ *C12N 15/1135* (2013.01); *C12N 2310/14* (2013.01)

(58) Field of Classification Search
CPC .............................. C12N 15/113; A61K 48/00
See application file for complete search history.

(56) References Cited

U.S. PATENT DOCUMENTS

2005/0255487 A1* 11/2005 Khvorova et al. ................. 435/6
2012/0003697 A1* 1/2012 Stevens ......................... 536/24.5

FOREIGN PATENT DOCUMENTS

| EP | 1752536 A1 | 2/2007 |
|---|---|---|
| WO | 0125422 A2 | 4/2001 |
| WO | 2005116204 A1 | 12/2005 |
| WO | 2007045243 A2 | 4/2007 |
| WO | 2007134245 A2 | 11/2007 |

OTHER PUBLICATIONS

Li et al., Molecular Pharmaceutics, vol. 3, No. 5, pp. 579-588, 2006.*
International Search Report from International Application No. PCT/US2011/037609 mailed Aug. 5, 2011.
International Search Report from International Application No. PCT/US2011/058856 mailed Jun. 22, 2012.
"Abstracts from the 7th International Meeting of the Sphingolipid Club held in Leiden, The Netherlands, Nov. 14-16, 2008", Naunyn-Schmied Arch Pharmacol. 380(4):359-72 (2009).
Alliston et al., "Repression of bone morphogenetic protein and activin-inducible transcription by Evi-1." J Biol Chem. 280(25): 24227-37 (2005).
Bidwell et al., "Development of elastin-like polypeptide for thermally targeted delivery of doxorubicin." Biochem Pharmacol. 73(5): 620-31 (2007).
Bordereaux et al., "Alternative splicing of the EVI1 zinc finger gene generates mRNAs which differ by the number of zinc finger motifs." Oncogene 5(6): 925-27 (1990).
Brooks et al., "Expression of the zinc finger gene EVI-1 in ovarian and other cancers." Br J Cancer. 74(10): 1518-25 (1996).
Buonamici et al., "EVI1 abrogates interferon-α response by selectively blocking PML induction." J Biol Chem. 280(1): 428-36 (2005).
Cattaneo & Nucifora, "EVI1 recruits the histone methyltransferase SUV39H1 for transcription repression." J Cell Biochem. 105(2): 344-52 (2008).
Chakraborty et al., Interaction of EVI1 with cAMP-responsive element-binding protein-binding protein (CBP) and p300/CBP-associated factor (P/CAF) results in reversible acetylation of EVI1 and in co-localization in nuclear speckles.) J Biol Chem. 276(48): 44936-43 (2001).
Chen et al., "Intelligent biosynthetic nanobiomaterials (IBNs) for hyperthermic gene delivery." Pharm Res. 25(3): 683-91 (2007).
Delwel et al., "Four of the seven zinc fingers of the EVI1 myeloid-transforming gene are required for sequence-specific binding to GA(C/T)AAGA(T/C)AAGATAA." Mol Cell Biol. 13(7): 4291-300 (1993).
Fuchs "EVI1and its role in myelodysplastic syndrome, myeloid leukemia and other malignant diseases." Casopis Lekaru Ceskych 145(8): 619-24 (2006).
Izutsu et al., "The corepressor CtBP interacts with Evi-1 to repress transforming growth factor beta signaling." Blood. 97(9): 2815-22 (2001).
Jazaeri et al., "Evaluation of EVI1 and EVI1s (Delta324) as potential therapeutic targets in ovarian cancer." Gynecol Oncol. 118(2): 189-95 (2010).
Kang et al., "Identification of novel candidate target genes, including EPHB3, MASP1 and SST at 3q26.2-q29 in squamous cell carcinoma of the lung." BMC Cancer 9: 237-52 (2009).
Kreider et al., "Loss of erythropoietin responsiveness in erythroid progenitors due to expression of the Evi-1 myeloid-transforming gene." Proc Natl Acad Sci USA 90(14): 6454-58 (1993).
Kumar et al., "Evi1 Promotes Leukemogenesis by Anti-Apoptotic Rather Than Differentiation-Blocking Effects in Murine MLL-AF9 Leukemia." Abstract of Oral Presentation at 50th Annual American Society of Hematology Meeting Dec. 8, 2008, Blood 112(11): Abstract 593 (2008).
Kurokawa et al., "The oncoprotein EVI-1 represses TGF-beta signalling by inhibiting Smad3." Nature 394(6688): 92-96 (1998).
Kurokawa et al., "The evi-1 oncoprotein inhibits c-Jun N-terminal kinase and prevents stress-induced cell death." EMBO J. 19(12): 2958-68 (2000).
Liu et al., "Evi1 is a survival factor which conveys resistance to both TGFbeta- and taxol-mediated cell death via PI3K/AKT." Oncogene 25(25): 3565-75 (2006).

(Continued)

*Primary Examiner* — Amy Bowman
(74) *Attorney, Agent, or Firm* — McDonnell Boehnen Hulbert & Berghoff LLP

(57) ABSTRACT

This invention describes a genetic system for targeting the EVI1 gene in mammalian cells. The EVI1 gene is an oncogenic transcription factor that, when expressed, accelerates cell division and inhibits death of cells. Nucleotide sequences that block the expression of EVI1 and drug delivery systems for them are described. These nucleotide sequences cause a block in cell growth and division and trigger death of mammalian cells, including lung and ovarian cancer cells.

16 Claims, 8 Drawing Sheets

(56) References Cited

OTHER PUBLICATIONS

Liu et al., "A genetically synthetic protein-based cationic polymer for siRNA delivery." Med Hypotheses. 76(2): 239-40 (2011).

Matsugi et al., "Identification, nuclear localization, and DNA-binding activity of the zinc finger protein encoded by the Evi-1 myeloid transforming gene." Mol Cell Biol. 10(3): 1259-64 (1990).

Mitani et al., "Growth inhibition of leukaemic cells carrying the t(3;21) by the AML1/EVI-1-specific antisense oligonucleotide." Br J Haematol. 90(3): 711-14 (1995).

Morishita et al., "The human Evi-1 gene is located on chromosome 3q24-q28 but is not rearranged in three cases of acute nonlymphocytic leukemias containing t(3;5)(q25;q34) translocations." Oncogene Res 5(3): 221-31 (1990).

Morishita et al., "Unique expression of the human Evi-1 gene in an endometrial carcinoma cell line: sequence of cDNAs and structure of alternatively spliced transcripts." Oncogene 5(7): 963-71 (1990).

Morishita et al., "EVI-1 zinc finger protein works as a transcriptional activator via binding to a consensus sequence of GACAAGATAAGATAAN1-28 CTCATCTTC." Oncogene 10(10): 1961-67 (1995).

Nitta et al., "Oligomerization of Evi-1 regulated by the PR domain contributes to recruitment of corepressor CtBP." Oncogene 24(40): 6165-73 (2005).

Palmer et al., "Evi-1 transforming and repressor activities are mediated by CtBP co-repressor proteins." J Biol Chem. 276(28): 25834-40 (2001).

Perkins et al., "EVI-1, a murine zinc finger proto-oncogene, encodes a sequence-specific DNA-binding protein." Mol Cell Biol. 11(5): 2665-74 (1991).

Perkins et al., "Role of EVI1 in cell cycle regulation: Relevance of specific target genes." Abstract of Poster Presented at 47th Annual American Society of Hematology Meeting Dec. 10-13, 2005, Blood 106(11): Abstract 1614 (2005).

Sood et al., "MDS1/EVI1 enhances TGF-beta1 signaling and strengthens its growth-inhibitory effect but the leukemia-associated fusion protein AML1/MDS1/EVI1, product of the t(3;21), abrogates growth-inhibition in response to TGF-beta1." Leukemia 13(3): 348-57 (1999).

Spensberger & Delwel, "A novel interaction between the proto-oncogene Evi1 and histone methyltransferases, SUV39H1 and G9a." FEBS Lett. 582(18): 2761-67 (2008).

Tanaka et al., "Evi-1 raises AP-1 activity and stimulates c-fos promoter transactivation with dependence on the second zinc finger domain." J Biol Chem. 269(39): 24020-26 (1994).

Vinatzer et al., "The leukaemia-associated transcription factors EVI-1 and MDS1/EVI1 repress transcription and interact with histone deacetylase." Br J Haematol. 114(3): 566-73 (2001).

Wieser, "The oncogene and developmental regulator EVI1: expression, biochemical properties, and biological functions." Gene 396(2): 346-57 (2007).

Yatsula et al., "Identification of binding sites of EVI1 in mammalian cells." J Biol Chem. 280(35): 30712-22 (2005).

Yokoi et al., "TERC identified as a probable target within the 3q26 amplicon that is detected frequently in non-small cell lung cancers." Clin Cancer Res. 9(13): 4705-13 (2003).

Yuasa et al., "Oncogenic transcription factor Evi1 regulates hematopoietic stem cell proliferation through GATA-2 expression." EMBO J. 24(11): 1976-87 (2005).

\* cited by examiner

Figure 6A and B.
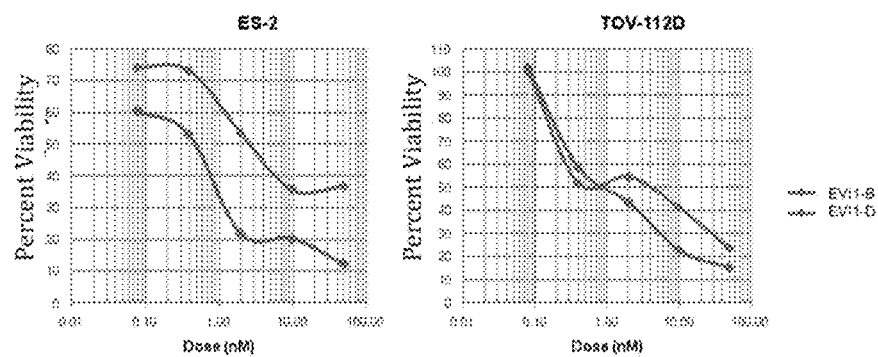
Figure 7A
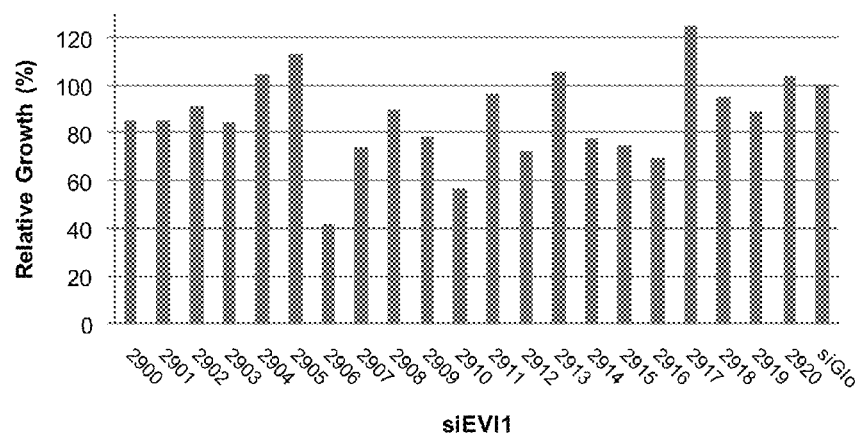

REAGENTS AND METHODS FOR TREATING CANCER

CROSS REFERENCE TO RELATED APPLICATION

This application claims benefit of U.S. Provisional Application No. 61/347,104, filed May 21, 2010, which is incorporated herein by reference in its entirety.

BACKGROUND OF THE INVENTION

1. Field of the Invention

This invention relates to cancer and reagents and methods for treating cancer. The invention generally relates to reagents and methods for inhibiting tumor cell growth, and provides said reagents and methods per se as well as in embodiments adjunct or complimentary to conventional anticancer treatments. The invention specifically provides isolated ribonucleic acid oligonucleotides, in single-stranded and double-stranded forms, that inhibit tumor cell growth, particularly in short interfering RNA (siRNA) embodiments, as well as pharmaceutical compositions thereof. Methods for using said reagents to inhibit cell growth are also provided.

2. Background of the Related Art

Tumor cell growth is known to involve expression of numerous genes, and particularly the dysregulation of that expression. Several genes having dysregulation are genes that are normally expressed during development but are improperly expressed in the tumor cell, contributing to uncontrolled growth, invasiveness and other phenotypic hallmarks of cancer.

One such gene is termed EVI1. The EVI1 (ecotropic virus integration site 1) gene, which encodes a zinc finger protein, plays important roles both in normal development and in oncogenesis. Overexpression of EVI1 has been found in certain solid tumors, such as those of the female reproductive organs, and EVI1 has been shown to be a key contributor to the emergence and clinical characteristics of myeloid malignancies, including acute myeloid leukemia (AML), chronic myeloid leukemia (CML), and myelodysplastic syndromes (MDS).

Human EVI1 is localized to chromosome 3, band q26 (Morishita et al., 1990, The human EVI1 gene is located on chromosome 3q24-q28 but is not rearranged in three cases of acute nonlymphocytic leukemias containing t(3; 5)(q25; q34) translocations, *Oncogene Res* 5: 221-31), spans 60 kb, and contains 16 exons, with multiple alternative 5' mRNA variants and several alternatively-spliced transcripts (Wieser, 2007, The oncogene and developmental regulator EVI1: expression, biochemical properties, and biological functions, *Gene* 396: 346-57). The major EVI1 form is a 1051-amino-acid protein with an apparent molecular weight of 145 kDa (Morishita et al., 1990, Unique expression of the human EVI1 gene in an endometrial carcinoma cell line: sequence of cDNAs and structure of alternatively spliced transcripts, *Oncogene* 5: 963-71; Matsugi et al., 1990, Identification, nuclear localization, and DNA-binding activity of the zinc finger protein encoded by the EVI1 myeloid transforming gene, *Mol Cell Biol* 10: 1259-64). EVI1 has multiple zinc finger domains that are organized into two sets, one each of seven and three zinc finger domains. A repression domain has been identified between the two sets of zinc finger domains, as well as an acidic region at the C-terminus (see FIG. 1). One particular transcript from the EVI1 gene, termed "the Δ324 transcript," is an alternative splice variant of EVI1 encoding an 88-kDa protein lacking zinc fingers 6 and 7; it is found at low levels in human and mouse cells (Bordereaux et al., 1990, Alternative splicing of the EVI1 zinc finger gene generates mRNAs which differ by the number of zinc finger motifs, *Oncogene* 5: 925-7.). Another variant, termed "the -Rp9 variant," lacks nine amino acids in the repression domain and is quite common in human and mouse cells.

The EVI1 protein is located in the nucleus and can bind to specific DNA sequences independently through both of its zinc finger domains (Perkins et al., 1991, EVI1, a murine zinc finger proto-oncogene, encodes a sequence-specific DNA-binding protein, *Mol Cell Biol* 11: 2665-74; Delwel et al., 1993, Four of the seven zinc fingers of the EVI1 myeloid-transforming gene are required for sequence-specific binding to GA(C/T)AAGA(T/C)AAGATAA, *Mol Cell Biol* 13: 4291-300; Morishita et al., 1995, EVI1 zinc finger protein works as a transcriptional activator via binding to a consensus sequence of GACAAGATAAGATAA(N1-28)CT-CATCTTC, *Oncogene* 10: 1961-7). The proximal zinc finger domain recognizes a consensus sequence of 15 nucleotides consisting of GA(C/T)AAGA(T/C) AAGATAA (SEQ ID NO: 201), and EVI1 has been shown to bind directly to the Gata2 promoter through this domain (Yuasa et al., 2005, Oncogenic transcription factor Evil regulates hematopoietic stem cell proliferation through GATA-2 expression, *EMBO J* 24: 1976-87; Yatsula et al., 2005, Identification of binding sites of EVI1 in mammalian cells, *J Biol Chem* 280: 30712-22). Additionally, the binding site for this domain has a Gata1 consensus motif that may compete with Gata1 for DNA binding (Kreider et al., 1993, Loss of erythropoietin responsiveness in erythroid progenitors due to expression of the EVI1 myeloid-transforming gene, *Proc Natl Acad Sci USA* 90: 6454-8). Although in vitro studies showed that the distal zinc finger domain recognizes the consensus GAAGATGAG (SEQ ID NO: 202), to date, there is no report of genes that are directly regulated by EVI1 through the distal zinc finger domain.

EVI1 also interacts with several transcription regulators as shown in FIG. 2. In particular, interaction with the co-repressor CtBP is important for EVI1 function (Izutsu et al., 2001, The corepressor CtBP interacts with EVI1 to repress transforming growth factor beta signaling, *Blood* 97: 2815-22; Palmer et al., 2001, EVI1 transforming and repressor activities are mediated by CtBP co-repressor proteins, *J Biol Chem* 276: 25834-40). CtBP increases the transcriptional repression of a reporter gene by EVI1, and point mutations in EVI1 that abolish the interaction significantly decrease EVI1-mediated transcriptional repression, growth inhibition of Mv1Lu cells in response to transforming growth factor (TGF)-β, and transformation of Rat-1 fibroblasts.

EVI1 also interacts with histone deacetylases directly or through CtBP, and histone deacetylase inhibitor partially relieves transcriptional repression by EVI1 (Vinatzer et al., 2001, The leukaemia-associated transcription factors EVI1 and MDS1/EVI1 repress transcription and interact with histone deacetylase, *Br J Haematol* 114: 566-73; Chakraborty et al., 2001, Interaction of EVI1 with cAMP-responsive element-binding protein-binding protein (CBP) and p300/CBP-associated factor (P/CAF) results in reversible acetylation of EVI1 and in co-localization in nuclear speckles, *J Biol Chem* 276: 44936-43; Spensberger & Delwel, 2008, A novel interaction between the proto-oncogene Evil and histone methyltransferases, SUV39H1 and G9a, *FEBS Lett* 582: 2761-7). It has also been shown that EVI1 binds to the coactivators CREB binding protein (CBP) and P300/CBP-associated factor (P/CAF), and co-expression of CBP could transform a repressive effect of EVI1 on a reporter gene into a moderately-activating effect (Cattaneo & Nucifora, 2008, EVI1 recruits the histone methyltransferase SUV39H1 for transcription repression, *J Cell Biochem* 105: 344-52). Furthermore, it was recently shown that EVI1 associates with the histone H3 lysine 9-specific histone methyltransferases SUV39H1 and G9a (Kurokawa et al., 1998, The oncoprotein EVI1 represses TGF-β signaling by inhibiting Smad3, *Nature* 394: 92-6; Sood et al., 1999, MDS1/EVI1 enhances TGF-β1 signaling and strengthens its growth-inhibitory effect but the leukemia-associated fusion protein AML1/MDS1/EVI1, product of the t(3; 21), abrogates growth-inhibition in response to TGF-β1, *Leukemia* 13: 348-5718,19). Thus, EVI1 forms higher-order complexes with various transcriptional regulators, and these associations are important for transcriptional regulation by EVI1 (see FIG. 2).

In addition, it has been shown that EVI1 affects various signaling pathways, including the TGF-β pathway (which has been the best-characterized). TGF-β controls proliferation and cellular differentiation of most cell types and plays an important role in inhibiting tumor development. EVI1 significantly represses TGF-β-mediated activation of the p3TP-Lux reporter plasmid in HepG2 cells, and EVI1 suppresses TGF-β-mediated growth inhibition in Mv1Lu and 32D cells (Alliston et al., 2005, Repression of BMP and activin-inducible transcription by EVI1, *J Biol Chem* 280: 24227-37; Nitta et al., 2005, Oligomerization of EVI1 regulated by the PR domain contributes to recruitment of corepressor CtBP 2005, *Oncogene* 24: 6165-73). Furthermore, EVI1 interferes with the induction of endogenous genes by TGF-β and other TGF-β family members in *Xenopus* animal cap explants and in C2C12 cells (Alliston et al., 2005, Id.). EVI1 inhibits TGF-β signaling through at least two possible mechanisms: reduction of Smad3 activity by physical interaction, and recruitment of the co-repressor CtBP (Izutsu et al., 2001, ibid; Kurokawa et al., 1998, ibid.).

One EVI1 transcript variant, termed MDS1/EVI1, consists of sequences derived from the MDS1 gene (which is located upstream of EVI1 and is also expressed on its own) and EVI1 (Wieser, 2007, ibid.). In contrast to EVI1, MDS1-EVI1 enhances TGF-β-induced growth inhibition in 32D cells (Sood et al., 1999, ibid.) and cannot efficiently repress TGF-β-mediated activation of p3TP-Lux in HepG2 cells (Nitta et al., 2005, ibid.). The lower repressive activity correlates with a reduced ability of MDS1/EVI1, compared with EVI1, to bind to the co-repressor CtBP (Id.) (see FIG. 2).

In contrast, certain cellular proteins induce apoptosis, the disruption thereof being another way tumor cell growth is promoted. Examples of such cellular proteins include the c-Jun N-terminal kinases (JNK), which are mitogen-activated protein kinases that are responsive to various stress stimuli and play an important role in triggering apoptosis. EVI1 significantly suppresses the JNK1-mediated phosphorylation of c-Jun. Conversely, reduction of EVI1 expression using antisense oligonucleotide recovers endogenous JNK1 activity experimentally in MOLM-1 and HEC1B cells (Kurokawa et al., 2000, The EVI1 oncoprotein inhibits c-Jun N-terminal kinase and prevents stress-induced cell death, *EMBO J* 19: 2958-68). EVI1 physically interacts with JNK through the proximal zinc finger domain, and an EVI1 mutant lacking this domain fails to suppress JNK1 activity. EVI1 also protects cells from stress-induced cell death with dependence on the ability to inhibit JNK (Id.) (see FIG. 2).

In addition to JNK, several mechanisms have been proposed to play a role in the survival function of EVI1. EVI1 protects murine bone marrow progenitors from apoptosis by activating the Promyelocytic leukemia (Pml) gene (Buonamici et al., 2005, EVI1 abrogates interferon-α response by selectively blocking PML induction, *J Biol Chem* 280: 428-36). It was also reported that EVI1 suppresses TGF-β or taxol-mediated apoptosis through a phosphoinositide 3-kinase (PI3K)-Akt dependent mechanism in RIE cells (Liu et al., Evi1 is a survival factor which conveys resistance to both TGFβ- and taxol-mediated cell death via PI3K/AKT, *Oncogene* 25: 3565-75). Activator protein (AP)-1 is a transcription factor complex consisting of a Fos-Jun heterodimer or Jun-Jun homodimer. It regulates gene expression in response to a variety of stimuli, and controls a number of cellular processes including differentiation, proliferation, and apoptosis. EVI1 raises AP-1 activity and stimulates c-fos promoter activation with dependence on its distal zinc finger domain in NIH3T3 and P19 cells (Tanaka et al., 1994, EVI1 raises AP-1 activity and stimulates c-fos promoter transactivation with dependence on the second zinc finger domain. *J Biol Chem* 269: 24020-6). Because the distal zinc finger domain is required for EVI1-mediated transformation of Rat-1 cells, the enhanced AP-1 activity probably contributes to cell transformation by EVI1.

EVI1 is highly expressed in certain cancer cell types. The EVI1 gene is amplified in 76% of squamous cell carcinoma, the most abundant type of non-small cell carcinoma (Kang et al., 2009, Identification of novel candidate target genes, including EPHB3, MASP1 and SST at 3q26.2-q29 in squamous cell carcinoma of the lung, *BMC Cancer* 9: 237-52). The EVI1 gene is also amplified in lung adenocarcinoma (Id.). The expression of EVI1 was significantly higher in 19 of 25 human non-small cell lung cancer samples, as determined by real time quantitative RT-PCR, compared with non-tumor tissues (Yokoi et al., 2003, TERC identified as a probable target within the 3q26 amplicon that is detected frequently in non-small cell lung cancers, *Clin Cancer Res.* 9: 4705-13). A study by Brooks et al. demonstrated, by RT-PCR, that EVI1 was highly expressed in 22 of 25 human ovarian tumors samples, and 6 of 7 melanoma samples (Brooks et al., 1996, Expression of the zinc finger gene EVI1 in ovarian and other cancers, *Br. J. Cancer* 74: 1518-25).

Thus, because inter alia of its role in oncogenesis, EVI1 is a desirable therapeutic target for the treatment of certain cancers, and there exists a need in the art for reagents and methods for inhibiting EVI1 expression or activity or both in order to inhibit tumor cell growth, induce apoptosis in tumor cells, and otherwise provide methods for improved cancer treatment, either used alone or in conjunction with conventional anticancer agents.

SUMMARY OF THE INVENTION

This invention provides reagents and methods for inhibiting EVI1 expression or activity or both in order to inhibit tumor cell growth, induce apoptosis in tumor cells, and otherwise provide methods for improved cancer treatment, either used alone or in conjunction with conventional anticancer agents.

In a first aspect, the invention provides isolated oligoribonucleotides having a sequence that is a contiguous portion of nucleotide sequence of the human EVI1 gene sequence (identified herein as SEQ ID NO: 1 and as GenBank Accession No. EVI1 v3 NM_001105078.3 and NP_001098548), wherein said contiguous portion of the nucleotide sequence of SEQ ID NO: 1 is from nucleotide 246 through 266, nucleotide 969 through 1002, nucleotide 2900 through 2920 or nucleotide 2984 through 3004, and a pharmaceutically acceptable salt thereof, that is capable of reducing expression of human EVI I in a tumor cell. In particular embodiments, the invention provides isolated oligoribonucleotides that are single-stranded and comprise 19 to 21 ribonucleotide residues. In particular embodiments, the invention provides isolated oligoribonucleotides that are double-stranded and comprise 19 to 21 ribonucleotide residues.

In specific embodiments, the invention provides reagents that are oligoribonucleotides identified by nucleotide 246 through 266 of SEQ ID NO: 1. Particular but non-limiting examples of such oligonucleotides are identified by SEQ ID NOS: 17 through 56. The invention provides reagents that are double-stranded, small interfering RNAs or small (short) hairpin (shRNA) comprising the combination SEQ ID NOs: 17 and 18, SEQ ID NOS: 19 and 20, SEQ ID NOS: 21 and 22, SEQ ID NOS: 23 and 24, SEQ ID NOS: 25 and 26, SEQ ID NOS: 27 and 28, SEQ ID NOS: 29 and 30, SEQ ID NOS: 31 and 32, SEQ ID NOS: 33 and 34, SEQ ID NOS: 35 and 36, SEQ ID NOS: 37 and 38, SEQ ID NOS: 39 and 40, SEQ ID NOS: 41 and 42, SEQ ID NOS: 43 and 44, SEQ ID NOS: 45 and 46, SEQ ID NOS: 47 and 48, SEQ ID NOS: 49 and 50, SEQ ID NOS: 51 and 52, SEQ ID NOS: 53 and 54, or SEQ ID NOS: 55 and 56.

In additional specific embodiments, the invention provides reagents that are oligoribonucleotides identified by nucleotide 969 through 989 or nucleotide 892 through 1002 of SEQ ID NO: 1. Particular but non-limiting examples of such oligonucleotides are identified by SEQ ID NOS: 57 through 120. The invention provides reagents that are double-stranded, small interfering RNAs (siRNAs) or small (short) hairpin (shRNA) comprising the combination of SEQ ID NOs: 57 and 58, SEQ ID NOS: 59 and 60, SEQ ID NOS: 61 and 62, SEQ ID NOS: 63 and 64, SEQ ID NOS: 65 and 66, SEQ ID NOS: 67 and 68, SEQ ID NOS: 69 and 70, SEQ ID NOS: 71 and 72, SEQ ID NOS: 73 and 74, SEQ ID NOS: 75 and 76, SEQ ID NOS: 77 and 78, SEQ ID NOS: 79 and 80, SEQ ID NOS: 81 and 82, SEQ ID NOS: 83 and 84, SEQ ID NOS: 85 and 86, SEQ ID NOS: 87 and 88, SEQ ID NOS: 89 and 90, SEQ ID NOS: 91 and 92, SEQ ID NOS: 93 and 94, SEQ ID NOS: 95 and 96, SEQ ID NOS: 97 and 98, SEQ ID NOS: 99 and 100, SEQ ID NOS: 101 and 102, SEQ ID NOS: 103 and 104, SEQ ID NOS: 105 and 106, SEQ ID NOS: 107 and 108, SEQ ID NOS: 109 and 110, SEQ ID NOS: 111 and 112, SEQ ID NOS: 113 and 114, SEQ ID NOS: 115 and 116, SEQ ID NOS: 117 and 118, or SEQ ID NOS: 119 and 120.

In further additional specific embodiments, the invention provides reagents that are oligoribonucleotides identified by nucleotide 2900 through 2920 of SEQ ID NO: 1. Particular but non-limiting examples of such oligonucleotides are identified by SEQ ID NOS: 121 through 160. The invention provides reagents that are double-stranded, small interfering RNAs (siRNAs) or small (short) hairpin (shRNA) comprising the combination of SEQ ID NOs: 121 and 122, SEQ ID NOS: 123 and 124, SEQ ID NOS: 125 and 126, SEQ ID NOS: 127 and 128, SEQ ID NOS: 129 and 130, SEQ ID NOS: 131 and 132, SEQ ID NOS: 133 and 134, SEQ ID NOS: 135 and 136, SEQ ID NOS: 137 and 138, SEQ ID NOS: 139 and 140, SEQ ID NOS: 141 and 142, SEQ ID NOS: 143 and 144, SEQ ID NOS: 145 and 146, SEQ ID NOS: 147 and 148, SEQ ID NOS: 149 and 150, SEQ ID NOS: 151 and 152, SEQ ID NOS: 153 and 154, SEQ ID NOS: 155 and 156, SEQ ID NOS: 157 and 158, or SEQ ID NOS: 159 and 160.

In yet further additional specific embodiments, the invention provides reagents that are oligoribonucleotides identified by nucleotide 2984 through 3004 of SEQ ID NO: 1. Particular but non-limiting examples of such oligonucleotides are identified by SEQ ID NOS: 161 through 200. The invention provides reagents that are double-stranded, small interfering RNAs (siRNAs) or small (short) hairpin (shRNA) comprising the combination of SEQ ID NOs: 161 and 162, SEQ ID NOS: 163 and 164, SEQ ID NOS: 165 and 166, SEQ ID NOS: 167 and 168, SEQ ID NOS: 169 and 170, SEQ ID NOS: 171 and 172, SEQ ID NOS: 173 and 174, SEQ ID NOS: 175 and 176, SEQ ID NOS: 177 and 178, SEQ ID NOS: 179 and 180, SEQ ID NOS: 181 and 182, SEQ ID NOS: 183 and 184, SEQ ID NOS: 185 and 186, SEQ ID NOS: 187 and 188, SEQ ID NOS: 189 and 190, SEQ ID NOS: 191 and 192, SEQ ID NOS: 193 and 194, SEQ ID NOS: 195 and 196, SEQ ID NOS: 197 and 198, or SEQ ID NOS: 199 and 200.

The invention specifically provides reagents that are isolated oligoribonucleotides identified by SEQ ID NOs: 2, 3, 4, 5, or 6. These embodiments are particularly provided as double-stranded, small interfering RNAs (siRNAs) or small (short) hairpin (shRNA) comprising the combination of SEQ ID NOs: 7 and 8, SEQ ID NOS: 9 and 10, SEQ ID NOS: 11 and 12, SEQ ID NOS: 13 and 14 or SEQ ID NOS: 15 and 16.

The invention further provides pharmaceutical compositions comprising any of said isolated oligoribonucleotides of the invention and a pharmaceutically acceptable salt, carrier, excipient or adjuvant. In certain embodiments, the pharmaceutical compositions of the invention are encapsulated into a liposome, wherein is certain additional particular embodiments said liposome is PEGylated and/or comprises a cell-targeting moiety, wherein said cell targeting moiety is but is not limited to a protein, a peptide or an aptamer. In certain additional embodiments, said pharmaceutical composition further comprises a nanoparticle, wherein said nanoparticle can contain inter alia lipids, cyclodextrin, chitosan, carbohydrate polymers, elastin-like polymers, or calcium phosphate polymers or combination thereof. In these embodiments, said nanoparticle can be PEGylated and/or comprises a cell-targeting moiety, wherein said cell targeting moiety is but is not limited to a protein, a peptide or an aptamer.

In a second aspect, the invention provides methods for inhibiting tumor cell growth, comprising the step of contacting a tumor cell with an effective amount of any of said isolated oligoribonucleotides of the invention. The invention also provides method for inhibiting tumor growth, comprising the step of administering to a human patient in need thereof a therapeutically effective amount of a pharmaceutical composition of the invention comprising any of said isolated oligoribonucleotides of the invention and a pharmaceutically acceptable salt, carrier, excipient or adjuvant. In particular embodiment, said pharmaceutical compositions are administered alone or in combination or conjunction with one or a plurality of conventional anticancer drugs or agents. In particular embodiments, said tumor is a malignant tumor of lung, breast, prostate, or ovarian tissue or organ origin, or melanoma or acute myelocytic leukemia.

The reagents and methods provided by this invention have certain advantages over the prior art. These include but are not limited to that the side-effects of cancer therapy are minimized by the specific targeting of the oligoribonucleotide to the EVI1 RNA, resulting in death of tumor cell and sparing normal tissues; that the EVI1-inhibiting oligoribonucleotide can be delivered in tumor-seeking liposomes, thereby increasing potency and efficacy of therapy; that the EVI1-inhibiting effect can be combined with traditional chemotherapeutic treatments by adding both factors into tumor-seeking liposomes to synergistically ablate growing tumors; and that the EVI1 inhibitor may be administered by any advantageous therapeutic route to enhance drug retention and increase drug concentration in the tumor.

Specific preferred embodiments of the present invention will become evident from the following more detailed description of certain preferred embodiments and the claims.

BRIEF DESCRIPTION OF THE DRAWINGS

FIG. 6 is a graph showing concentration-dependent effects of siRNA against the EVI1 gene on cell survival. Ovarian tumor cells TOD112D and ES-2 were seeded into each well of a 12 well plate. Increasing concentrations of siRNA were introduced into the cells using 1 microliter of Dharmafect reagent in 2 ml of medium. The number of viable cells was determined using trypan blue staining and counting in a hemacytometer.

FIGS. 7A and 7B are graphs showing the results of tumor cell growth inhibition by siRNA species produced by tiling siRNA sequences 10 bp upstream and downstream of siEVI1-2910 (SEQ ID NOs: 121-160) to inhibit ovarian tumor cell growth. A concentration of 2.5 nM of each siRNA was administered using DharmaFECT transfection reagent to TOV-112D (FIG. 7A) or ES-2 (FIG. 7B) ovarian tumor cells. Results are depicted as percent growth inhibition of TOV-112D or ES-2 ovarian tumor cells relative to a transfection (siGlo) control.

DETAILED DESCRIPTION OF THE PREFERRED EMBODIMENTS

Figure 1:
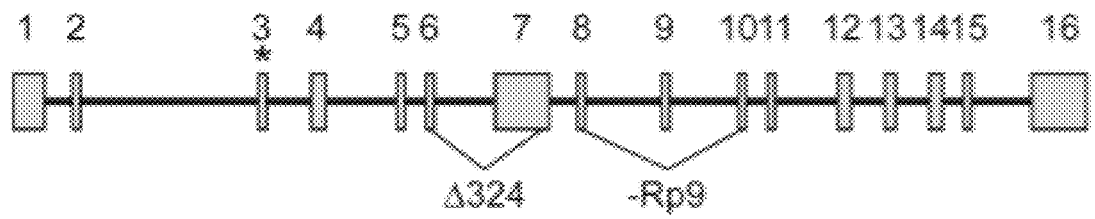
FIG. 1 is a schematic representation of the exon/intron structure of the human EVI1 gene on human chromosome 3.
Figure 2:
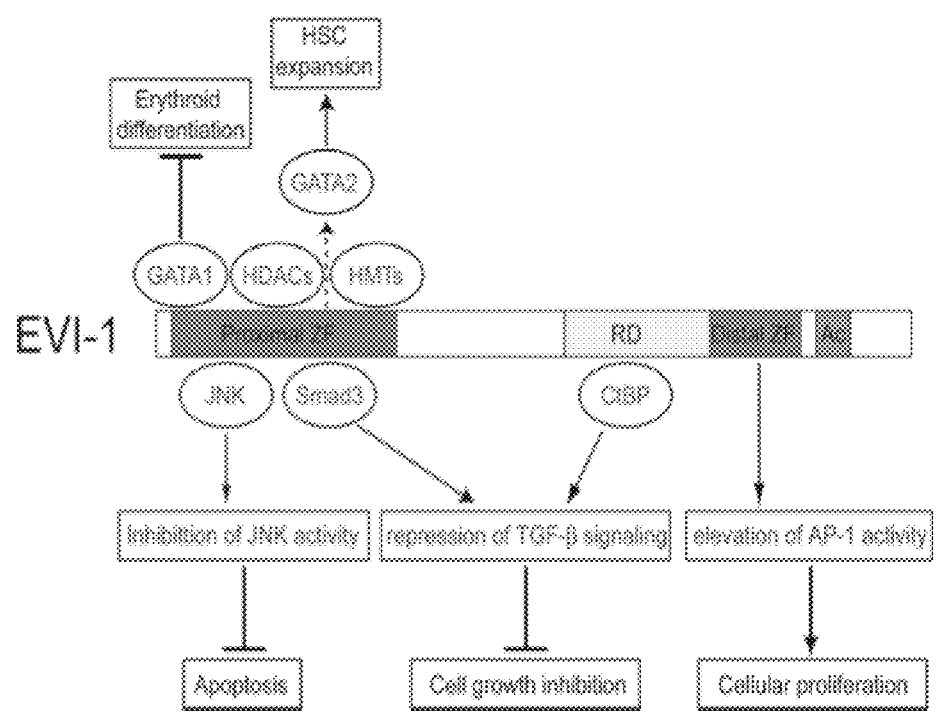
FIG. 2 is a schematic diagram of stimulatory and inhibitory interactions between human EVI1 protein and several human apoptosis-related proteins.
Figure 3:
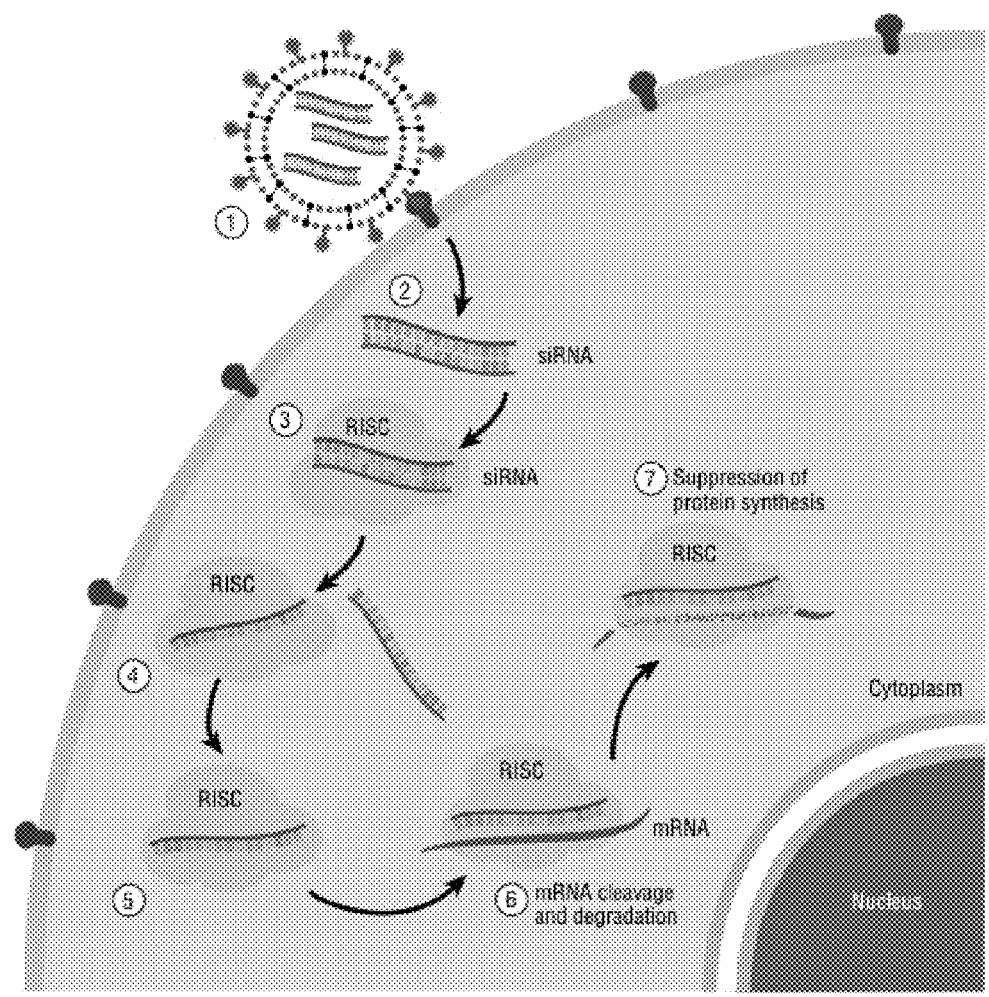
FIG. 3 is a schematic diagram of a pathway for activity of an siRNA silencing mechanism in mammalian cells. As shown in the Figure, 1) Small interfering RNAs of a 21 bp sequence specific to a portion of the gene targeted for silencing is introduced into the cells using a nanoparticle delivery system; 2) the siRNA is freed from the nanoparticle due to proteolytic digestion of elastin peptide comprising particular embodiments of said nanoparticles; 3) the siRNA binds to RISC protein complexes; 4) the sense-strand is removed from the RISC complex; 5) the siRNA RISC complex binds the target mRNA; 6) the target mRNA is degraded by nucleases; and 7) protein expression is suppressed.

Conventional techniques well known to those with skill in the art were used for oligonucleotide synthesis, and enzymatic reactions and purification techniques were performed according to manufacturers' specifications or as commonly accomplished in the art or as described herein. The techniques and procedures were generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, molecular biology, genetic engineering, analytical chemistry, synthetic organic chemistry, and medicinal and pharmaceutical chemistry described herein are those well-known and commonly used in the art. Standard techniques can be used for chemical syntheses, chemical analyses, and treatment of patients.

Unless otherwise required by context, singular terms shall include pluralities and plural terms shall include the singular.

As utilized in accordance with the present disclosure, the following terms, unless otherwise indicated, shall be understood to have the following meanings:

The invention provides isolated polynucleotides, particularly polynucleotides encoding a portion of human EVI1. As used herein, the term "isolated polynucleotide" means a polynucleotide of genomic, cDNA, or synthetic origin or a combination thereof, which by virtue of its source the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "polynucleotide" as used herein means a polymeric form of nucleotides that are at least 10 bases in length. In certain embodiments, the bases may be ribonucleotides or deoxyribonucleotides or a modified form of either type of nucleotide. The term includes single and double stranded forms of DNA or RNA The term "PEGylated" as used herein means attachment (covalent or otherwise) of one or a plurality of polyethylene glycol molecules to a protein, lipid or other biomolecule.

The term "oligonucleotide" as used herein includes naturally occurring, and modified nucleotides linked together by naturally occurring, and/or non-naturally occurring oligonucleotide linkages. Oligonucleotides are a polynucleotide subset generally comprising no more than 200 nucleotides. In certain embodiments, oligonucleotides are 10 to 60 nucleotides in length. In certain embodiments, oligonucleotides are 12, 13, 14, 15, 16, 17, 18, 19, 20, 21, or 30 to 40 bases in length. Oligonucleotides can be single stranded, e.g. for use as antisense RNAs, or double-stranded, as small interfering RNAs (siRNAs) or small (or short) hairpin RNAs (shRNAs). An oligonucleotide can include a detectable label, such as a radiolabel, a fluorescent label, an antigenic label or a hapten.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphate, phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res. 14: 9081; Stec et al., 1984, J. Am. Chem. Soc. 106: 6077; Stein et al., 1988, Nucl. Acids Res. 16: 3209; Zon et al., 1991, Anti-Cancer Drug Design 6: 539; Zon et al., 1991, OLIGONUCLEOTIDES AND ANALOGUES: A PRACTICAL APPROACH, (F. Eckstein, ed.), Oxford University Press, Oxford England, pp. 87-108; Stec et al., U.S. Pat. No. 5,151,510; Uhlmann and Peyman, 1990, Chemical Reviews 90: 543, the disclosures of each of which are hereby incorporated by reference for any purpose.

The term "vector" is used to refer to a molecule (e.g., nucleic acid, plasmid, or virus) used to transfer coding information to a host cell or a target cell. Viral vectors suitable for the methods of the invention include those derived from, for example, adenovirus, adeno-associated virus, retroviruses, herpes simplex virus, or vaccinia virus.

The term "expression vector" refers to a vector that is suitable for transformation of a host cell or a target cell and contains nucleic acid sequences comprising control sequences that direct and/or control the expression of inserted nucleic acid sequences. The term "expression" includes, but is not limited to, processes such as transcription and RNA splicing, if introns are present.

An expression vector of the invention can comprise a DNA or RNA sequence having a coding sequence that is operatively linked to a control sequence. The term "control sequence" or "control element" as used herein refers to polynucleotide sequences that can effect the expression and processing of coding sequences to which they are ligated. The nature of such control sequences may differ depending upon the host organism. According to certain embodiments, control sequences for prokaryotes may include promoters, repressors, operators, ribosomal binding sites, and transcription termination sequences and antisense mRNA. According to certain embodiments, control sequences for eukaryotes may include promoters, enhancers and transcription termination sequences, or sequences that regulate protein degradation, mRNA degradation, nuclear localization, nuclear export, cytoplasmic retention, protein phosphorylation, protein acetylation, protein sumolation, or RNA inhibition (RNAi). In certain embodiments, "control sequences" can include leader sequences and/or fusion partner sequences. "Control sequences" are "operatively linked" to a coding sequence when the "control sequence" effects expression and processing of coding sequences to which they are ligated.

As used herein, the phrase "tissue specific promoters" refers to nucleic acid sequences comprising control sequences that are capable of directing transcription of a coding sequence and that are activated specifically within a specific cell type. For example, liver specific promoters that drive expression of genes in liver cells include, but are not limited to, promoters from genes encoding human or mouse α1-antitrypsin, albumin promoter, serum amyloid A, transthyretin, hepatocyte nuclear factor 6, and major urinary protein (MUP).

Typically, expression vectors used in a host cells or target cell contain sequences for vector maintenance and for expression of exogenous nucleotide sequences. Such sequences, collectively referred to as "flanking sequences" in certain embodiments will typically include one or more of the following nucleotide sequences: a promoter, one or more enhancer sequences, a transcriptional termination sequence, a complete intron sequence containing a donor and acceptor splice site, a ribosome binding site, a polyadenylation signal sequence, a polylinker region comprising one or a plurality of restriction endonuclease sites for inserting nucleic acid encoding an siRNA to be expressed, and a selectable marker element.

Flanking sequences may be homologous (i.e., from the same species and/or strain as the host cell or the target cell), heterologous (i.e., from a species other than the host cell or the target cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell or the target cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. The flanking sequence also may be synthesized using the methods described herein for nucleic acid synthesis or cloning.

Where all or only a portion of the flanking sequence is known, it may be obtained using in vitro amplification methods such as polymerase chain reaction (PCR) and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen column chromatography (Chatsworth, Calif.), or other methods known to the skilled artisan. The selection of suitable enzymes to accomplish this purpose is readily apparent to one of ordinary skill in the art.

A transcription termination sequence is typically located 3' to the end of a polypeptide-coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein. Eukaryotes have a sequence that functions both as a transcription termination signal and as a poly A signal required for endonuclease cleavage followed by the addition of poly A residues (usually consisting of about 200 A residues).

The expression and cloning vectors of the present invention will typically contain a promoter that is recognized by the host organism and operatively linked to nucleic acid encoding a portion of the human EVI1 gene. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no experimental control over gene expression. A large number of promoters, recognized by a variety of potential host cells or target cells, are well known.

Suitable promoters for use with mammalian cells are well known and include, but are not limited to, those obtained from the genomes of eukaryotic viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bernoist and Chambon, 1981, Nature 290: 304-10); the CMV promoter; the promoter contained in the 3' long terminal repeat of Rous sarcoma virus (Yamamoto, et al., 1980, Cell 22: 787-97); the herpes thymidine kinase promoter (Wagner et al., 1981, Proc. Natl. Acad. Sci. U.S.A. 78: 1444-45); and the regulatory sequences of the metallothionine gene (Brinster et al., 1982, Nature 296: 39-42). Also of interest are the following animal transcriptional control regions, which exhibit tissue specificity and have been utilized in transgenic animals: the elastase I gene control region that is active in pancreatic acinar cells (Swift et al., 1984, Cell 38: 639-46; Ornitz et al., 1986, Cold Spring Harbor Symp. Quaint. Biol. 50: 399409; MacDonald, 1987, Hepatology 7: 425-515); the insulin gene control region that is active in pancreatic beta cells (Hanahan, 1985, Nature 315: 115-22); the mouse mammary tumor virus control region that is active in testicular, breast, lymphoid and mast cells (Leder et al., 1986, Cell 45: 485-95); the beta-globin gene control region that is active in myeloid cells (Mogram et al., 1985, Nature 315: 338-40; Kollias et al., 1986, Cell 46: 89-94); the myelin basic protein gene control region that is active in oligodendrocyte cells in the brain (Readhead et al., 1987, Cell 48: 703-12); the myosin light chain-2 gene control region that is active in skeletal muscle (Sani, 1985, Nature 314: 283-86); the gonadotropic releasing hormone gene control region that is active in the hypothalamus (Mason et al., 1986, Science 234: 1372-78); and most particularly the immunoglobulin gene control region that is active in lymphoid cells (Grosschedl et al., 1984, Cell 38: 647-58; Adames et al., 1985, Nature 318: 533-38; Alexander et al., 1987, Mol. Cell Biol. 7: 1436-44).

Preferably, the promoter of an expression vector of the invention is active in the tissue from which a target or host cell is derived. For example, if the cell is a liver cell, one could advantageously use the albumin gene control region (Pinkert et al., 1987, Genes and Devel. 1: 268-76); the alpha-fetoprotein gene control region (Krumlauf et al., 1985, Mol. Cell Biol. 5: 1639-48; Hammer et al., 1987, Science 235: 53-58); or the alpha 1-antitrypsin gene control region (Kelsey et al., 1987, Genes and Devel. 1: 161-71), all of which are active in the liver.

The vectors of the invention can also contain an enhancer sequence that increases transcription in higher eukaryotic cells. Enhancers are cis-acting elements of DNA, are usually about 10-300 bp in length, and act on promoters to increase transcription Enhancers are relatively orientation- and position-independent, They have been found within introns as well as within several kilobases both 5' and 3' to the transcription unit. Several enhancer sequences available from mammalian genes are known (e.g., enhancers from globin, elastase, albumin, alpha-feto-protein, insulin, transthyretin, and HNF-6 genes). An enhancer from a virus also can be used to increase expression of a gene. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically located at a site 5' from the promoter.

Expression vectors of the invention may be constructed from a convenient starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding, for example, an EVI1 siRNA has been inserted into the proper site of the vector, the completed vector may be inserted into a suitable host cell or a target cell. The introduction of all expression vector encoding EVI1 siRNA into a selected host cell or target cell may be accomplished by well-known methods including methods such as transfection, infection, calcium chloride, electroporation, microinjection, lipofection, DEAE-dextran method, or other known techniques as described above. The method selected will in part be a function of the type of host cell or target cell to be used. These methods and other suitable methods are well known to the skilled artisan, and are set forth, for example, in Sambrook et al., 2001, MOLECULAR CLONING: A LABORATORY MANUAL, 3d ed., Cold Spring Harbor Laboratory Press, Cold Spring Harbor, N.Y.

The term "host cell" is used to refer to a cell into which has been introduced, or that is capable of having introduced, a nucleic acid sequence and then of expressing a gene of interest. The term includes the progeny of the parent cell, whether or not the progeny is identical in morphology or in genetic make-up to the original parent, so long as the gene is present. In preferred embodiments, the host cell is a eukaryotic cell, more preferably a mammalian cell and most preferably a rodent or human cell.

Selection of an appropriate target cell will also depend on the various factors discussed above for selection of an appropriate host cell. In addition, a target cell can be selected based on the disease or condition that affects a patient who is to be treated by methods of the invention.

The term "transfection" is used to refer to the uptake of foreign or exogenous DNA by a cell, and a cell has been "transfected" when the exogenous DNA has been introduced inside the cell. A number of transfection techniques are well known in the art and are disclosed herein. See, e.g., Graham et al., 1973, Virology 52: 456; Sambrook et al., 2001, MOLECULAR CLONING: A LABORATORY MANUAL, 3d ed., Cold Spring Harbor Laboratory Press, Cold Spring Harbor, N.Y.; Davis et al., 1986, BASIC METHODS IN MOLECULAR BIOLOGY (Elsevier); and Chu et al., 1981, Gene 13: 197. Such techniques can be used to introduce an exogenous DNA into suitable host cells.

The term "agent" is used herein to denote a chemical compound, a mixture of chemical compounds, a biological macromolecule, or an extract made from biological materials.

The term "pharmaceutical composition" as used herein refers to a composition comprising a pharmaceutically acceptable carrier, excipient, or diluent and a chemical compound, peptide, or composition as described herein that is capable of inducing a desired therapeutic effect when properly administered to a patient.

The term "therapeutically effective amount" refers to the amount of growth hormone or a pharmaceutical composition of the invention or a compound identified in a screening method of the invention determined to produce a therapeutic response in a mammal. Such therapeutically effective amounts are readily ascertained by one of ordinary skill in the art and using methods as described herein.

As used herein, "substantially pure" means an object species that is the predominant species present (i.e., on a molar basis it is more abundant than any other individual species in the composition). In certain embodiments, a substantially purified fraction is a composition wherein the object species comprises at least about 50 percent (on a molar basis or on a weight or number basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (wherein contaminating species cannot be detected in the composition by conventional detection methods) wherein the composition consists essentially of a single macromolecular species.

The term "patient" includes human and animal subjects.

As used herein, the terms "tumor growth" and "tumor cell proliferation" are used to refer to the growth of tumor cells. The term "tumor cell" as used herein refers to a cell that is neoplastic. A tumor cell can be benign, i.e. one that does not form metastases and does not invade and destroy adjacent normal tissue, or malignant, i.e. one that invades surrounding tissues, is capable of producing metastases, may recur after attempted removal, and is likely to cause death of the host. Preferably a tumor cell that is subjected to a method of the invention is an epithelial-derived tumor cell, such as a tumor cell derived from skin cells, lung cells, intestinal epithelial cells, colon epithelial cells, testes cells, breast cells, prostate cells, brain cells, bone marrow cells, blood lymphocytes, ovary cells or thymus cells.

A preferred embodiment of the invention comprises a drug, a nucleotide with a sequence recognizing a portion of the RNA expressed from the EVI1 gene Inhibition of the expression of EVI1 within a cell causes a block of the cell's division and/or an activation of apoptosis. In one embodiment of the invention, the nucleotide binds by Watson-Crick sequence complementarity to the EVI1 gene sequence to block its expression. The nucleotide may be a DNA oligonucleotide of a length sufficient to inhibit expression of the EVI1 gene at the DNA or RNA level. In another embodiment, the nucleotide may be double-stranded RNA (dsRNA) that, in association with the RNA processing mechanism, down-regulates the expression of EVI1. This dsRNA may be a small interfering RNA (siRNA) of approximately 20 basepairs.

In another embodiment of the invention, the EVI1-inhibiting nucleotide is encapsulated in a liposome or nanoparticle that can protect the nucleotide in the circulating blood and concentrate the nucleotide in targeted tissues. Liposomes are lipid surface molecules that form layers surrounding the nucleotide. Typically, cationic liposomes are used to encapsulate negatively charged nucleotides. Nanoparticles are typically chemically based shell structures that bind up the nucleotide and stabilize the molecule in the blood. Nanoparticles typically comprise sugar, dextran, calcium phosphate, chitosan, peptide and/or plastic polymers.

In a further embodiment of the invention, targeting ligands are associated with the liposome or nanoparticle containing the EVI1-inhibiting molecule, that target receptors on tumor cells designated for apoptotic destruction. The liposomes may also be coated with polyethylene glycol (i.e., are PEGylated) to prolong the lifetime of the liposomes in the circulation. Similarly, nanoparticles may be so coated.

Targeting molecules may be organic chemical linkers termed aptamers that specifically bind receptors on the surface of a target cell. The aptamers may be covalently linked to the lipids of the liposome or polymers of the nanoparticles. Other molecules that may be used to target liposomes or nanoparticles to tumor cells are peptides, proteins or antibodies that are directed to a specific receptor on the surface of tumor cells. In preferred embodiments of the invention, the liposomes or nanoparticles may be directed towards acute myelocytic leukemia, lung, ovarian, skin or other types of cancer cells.

In certain embodiments, this application relates to double stranded RNAs (dsRNA) and RNAi constructs. The term "dsRNA" as used herein refers to a double stranded RNA molecule capable of RNA interference (RNAi), including siRNA. In addition, RNAi is a term initially applied to a phenomenon observed in plants and worms where double-stranded RNA (dsRNA) blocks gene expression in a specific and post-transcriptional manner. RNAi provides a useful method of inhibiting or reducing gene expression in vitro or in vivo.

The term "short interfering RNA," "siRNA," or "short interfering nucleic acid," as used herein, refers to any nucleic acid capable of mediating RNAi or gene silencing when processed appropriately by a cell. For example, the siRNA can be a double-stranded polynucleotide molecule comprising self-complementary sense and antisense regions, wherein the antisense region comprises complementarity to a target gene. The siRNA can be a single-stranded hairpin polynucleotide having self-complementary sense and antisense regions, wherein the antisense region comprises complementarity to a target gene. The siRNA can be a circular single-stranded polynucleotide having two or more loop structures and a stem comprising self-complementary sense and antisense regions, wherein the antisense region comprises complementarity to a target gene, and wherein the circular polynucleotide can be processed either in vivo or in vitro to generate an active siRNA capable of mediating RNAi. The siRNA can also comprise a single stranded polynucleotide having complementarity to a target gene, wherein the single stranded polynucleotide can further comprise a terminal phosphate group, such as a 5'-phosphate, or 5',3'-diphosphate. In certain embodiments, the siRNAs are non-enzymatic nucleic acids that bind to a target nucleic acid and alter the activity of the target nucleic acid. Binding and/or activity of the siRNA may be facilitated by interaction with one or more protein or protein complexes, such as the RNA Induced Silencing Complex (or RISC). In certain embodiments, the siRNAs comprise a sequence that is complementary to a target sequence along a single contiguous sequence of one strand of the siRNA molecule.

Optionally, the siRNAs of the application contain a nucleotide sequence that hybridizes under physiologic conditions (e.g., in a cellular environment) to the nucleotide sequence of at least a portion of the mRNA transcript for the gene to be inhibited (the "target" gene). The double-stranded RNA need only be sufficiently similar to natural RNA that it has the ability to mediate RNAi. Thus, the application has the advantage of being able to tolerate sequence variations that might be expected due to genetic mutation, strain polymorphism or evolutionary divergence. The number of tolerated nucleotide mismatches between the target sequence and the siRNA sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art and calculating the percent difference between the nucleotide sequences by, for example, the Smith-Waterman algorithm as implemented in the BESTFIT software program using default parameters. Greater than 90%, 95%, 96%, 97%, 98%, or 99% sequence identity, or even 100% sequence identity, between the siRNA and the portion of the target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing).

The double-stranded structure of dsRNA may be formed by a single self-complementary RNA strand, two complementary RNA strands, or a DNA strand and a complementary RNA strand. Optionally, RNA duplex formation may be initiated either inside or outside the cell. The RNA may be introduced in an amount that allows delivery of at least one copy per cell. Higher doses (e.g., at least 5, 10, 100, 500 or 1000 copies per cell) of double-stranded material may yield more effective inhibition, while lower doses may also be useful for specific applications Inhibition is sequence-specific in that nucleotide sequences corresponding to the duplex region of the RNA are targeted for inhibition.

As described herein, the subject siRNAs comprise a duplex region about 19-30 nucleotides in length, about 21-27 nucleotides in length, about 21-25 nucleotides in length, or about 21-23 nucleotides in length. The siRNAs are understood to recruit nuclease complexes and guide the complexes to the target gene transcript by pairing to the specific sequences. As a result, the target gene transcript is degraded by the nucleases in the protein complex. In certain embodiments, the siRNA molecules comprise a 3' hydroxyl group. In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 27 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject dsRNAs (e.g., siRNAs) can be carried out by chemical synthetic methods or by recombinant nucleic acid techniques. Endogenous RNA polymerase of the treated cell may mediate transcription in vivo, or cloned RNA polymerase can be used for transcription in vitro. As used herein, dsRNA or siRNA molecules of the application need not be limited to those molecules containing only RNA, but further encompasses chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs. Merely to illustrate, the backbone of an dsRNA or siRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the application lack 2'-hydroxy (2'-OH) containing nucleotides. In certain embodiments, the siRNA molecules comprise a phosphorothioate sense strand. In certain embodiments, the siRNA molecules comprise a phosphodiester antisense strand.

In a specific embodiment, at least one strand of the siRNA molecules has a 3' overhang from about 1 to about 10 nucleotides in length, about 1 to 5 nucleotides in length, about 1 to 3 nucleotides in length, or about 2 to 4 nucleotides in length. In certain embodiments, an siRNA may comprise one strand having a 3' overhang and the other strand is blunt-ended at the 3' end (e.g., does not have a 3' overhang). In another embodiment, an siRNA may comprise a 3' overhang on both strands. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects that may be caused by the sequence-independent dsRNA response. In such embodiments, the use of local delivery systems and/or agents which reduce the effects of interferon or PKR are preferred.

In a further specific embodiment, the dsRNA or siRNA is in the form of a short hairpin structure (shRNA). The shRNAs can be synthesized exogenously or can be formed by transcribing from RNA polymerase III promoters in vivo. Preferably, such shRNAs are engineered in cells or in an animal to ensure continuous and stable suppression of a target gene. It is known in the art that siRNAs can be produced by processing a hairpin RNA in the cell.

In preferred embodiments, an EVI1 siRNA is designed and constructed as described herein, which describes production of an siRNA that corresponds to nucleotide residues 246-266 (SEQ ID NO: 17-56), 969-1002 (SEQ ID NO: 57-120), 2900-2920 (SEQ ID NO: 121-160), or 2984-3004 (SEQ ID NO: 161-200) of the human EVI1 coding sequence (SEQ ID NO:1). The EVI1 siRNA described herein are exemplary EVI1 siRNA molecules that have a nucleotide sequence as shown herein. Alternatively, EVI1 siRNA can be constructed using the methods described in Elbashir et al. (2001, Genes Dev. 15:188-200; 2001, Nature 411:494-498), which is incorporated herein by reference.

In certain embodiments, EVI1 inhibitors as provided by the invention are species of short interfering RNA (siRNA). The term "short interfering RNA" or "siRNA" as used herein refers to a double stranded nucleic acid molecule capable of RNA interference or "RNAi", as disclosed, for example, in Bass, 2001, Nature 411: 428-429; Elbashir et al., 2001, Nature 411: 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., Intentional PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. As used herein, siRNA molecules need not be limited to those molecules containing only RNA, but may further encompass chemically modified nucleotides and non-nucleotides having RNAi capacity or activity.

RNA interference refers to the process of sequence-specific post-transcriptional gene silencing in animals mediated by short interfering RNAs (siRNA) (Fire et al., 1998, Nature 391:806). The presence of long dsRNAs in cells stimulates the activity of a ribonuclease III enzyme referred to as "dicer." Dicer is involved in processing of the long dsRNA into siRNA, which are short pieces of dsRNA (Berstein et al., 2001, Nature 409:363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science 293:834). The RNAi response also features an endonuclease complex containing an siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, Genes Dev. 15:188).

Short interfering RNA mediated RNAi has been studied in a variety of systems. Fire et al. were the first to observe RNAi in *C. elegans* (1998, Nature 391:806). Wianny and Goetz described RNAi mediated by dsRNA in mouse embryos (1999, Nature Cell Biol. 2:70). Hammond et al. described RNAi in Drosophila cells transfected with dsRNA (2000, Nature 404:293). Elbashir et al. described RNAi induced by introduction of duplexes of synthetic 21-nucleotide RNAs in cultured mammalian cells including human embryonic kidney and HeLa cells (2001, Nature 411:494).

Recent work in Drosophila embryo lysates has revealed certain requirements for siRNA length, structure, chemical composition, and sequence that are essential to mediate efficient RNAi activity. These studies have shown that siRNA duplexes comprising 21 nucleotides are most active when containing two nucleotide 3'-overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J. 20:6877). Other studies have indicated that a 5'-phosphate on the target-complementary strand of a siRNA duplex is required for siRNA activity and that ATP is utilized in cells to maintain the 5'-phosphate moiety on the siRNA (Nykanen et al., 2001, Cell 107:309). However siRNA molecules lacking a 5'-phosphate are active when introduced exogenously, suggesting that 5'-phosphorylation of siRNA constructs can occur in vivo.

An EVI1 siRNA molecule of the invention can be a double-stranded polynucleotide molecule comprising self-complementary sense and antisense regions, wherein the antisense region comprises a nucleotide sequence that is complementary to a portion of the nucleotide sequence of EVI1 and the sense region has a nucleotide sequence corresponding to the EVI1 nucleic acid sequence or a portion thereof. The EVI1 siRNA molecule can be assembled from two separate oligonucleotides, where one strand is the sense strand and the other is the antisense strand, wherein the antisense and sense strands are self-complementary. The EVI1 siRNA molecule can also be assembled from a single oligonucleotide having self-complementary sense and antisense regions linked by means of a nucleic acid based or non-nucleic acid-based linker. The EVI1 siRNA molecule can be a polynucleotide can form a substantially symmetrical duplex, asymmetric duplex, hairpin, or asymmetric hairpin secondary structure. The EVI1 siRNA molecule can also comprise a single stranded polynucleotide having nucleotide sequence complementary to the EVI1 nucleotide sequence or a portion thereof, wherein the single stranded polynucleotide can further comprise a terminal phosphate group, such as a 5',3'-diphosphate or a 5'-phosphate as discussed, for example, in Martinez et al., 2002, Cell 110:563-574 and Schwarz et al., 2002, Molecular: Cell 10:537-568.

An EVI1 siRNA molecule of the invention comprising a single stranded hairpin structure is preferably about 36 to about 70 nucleotides in length, having two complementary sequences of about 15 to about 30 nucleotides separated by a spacer sequence that allows hybridization of the complementary sequences. Thus, the single stranded hairpin structure has about 15 to, about 30 base pairs comprising the duplex portion of the molecule. In one embodiment, the hairpin siRNA has about 18, 19, 20, or 21 base pairs in the duplex portion and a loop portion of a length that accommodates hybridization of the complementary siRNA sequences.

In certain embodiments, the invention provides expression vectors comprising a nucleic acid sequence encoding at least one EVI1 siRNA molecule of the invention, in a manner that allows expression of the EVI1 siRNA molecule. For example, the vector can contain sequence(s) encoding both strands of a EVI1 siRNA molecule comprising a duplex. The vector can also contain sequence(s) encoding a single nucleic acid molecule that is self-complementary and thus forms an EVI1 hairpin siRNA molecule. Non-limiting examples of such expression vectors are described in Paul et al., 2002, Nature Biotechnology 19:505; Miyagishi and Taira, 2002, Nature Biotechnology 19:497; Lee et al., 2002, Nature Biotechnology 19:500; and Novina et al., 2002, Nature Medicine, online publication June 3.

In other embodiments, the invention provides mammalian cells, for example, human cells, comprising an expression vector of the invention. In further embodiments, the expression vector comprising said cells of the invention comprises a sequence for an siRNA molecule complementary to at least a portion of human EVI1 coding sequence, wherein expression of said siRNA in the cell inhibits EVI1 expression therein. In other embodiments, expression vectors of the invention comprise a nucleic acid sequence encoding two or more siRNA molecules, which can be the same or different. In other embodiments of the invention, siRNA molecules, preferably EVI1-specific siRNA molecules, are expressed from transcription units inserted into DNA or RNA vectors.

In certain embodiments, siRNA molecules according to the invention can comprise a delivery vehicle, including inter alia liposomes, for administration to a subject; carriers and diluents and their salts; and can be present in pharmaceutical compositions. Methods for the delivery of nucleic acid molecules are described, for example, in Akhtar et al., 1992, Trends Cell Bio. 2:139; Delivery Strategies for Antisense Oligonucleotide Therapeutics, ed. Akhtar, 1995, Maurer et al., 1999, Mol. Membr. Biol. 16:129-140; Hofland and Huang, 1999, Handb. Exp. Pharmacol., 137:165-192; and Lee et al., 2000, ACS Symp. Ser. 752:184-192, all of which are incorporated herein by reference. Beigelman et al., U.S. Pat. No. 6,395,713 and Sullivan et al., PCT WO 94/02595, further describe general methods for delivery of nucleic acid molecules into cells and tissues. These protocols can be utilized for the delivery of virtually any nucleic acid molecule into a cell. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722).

Alternatively, the nucleic acid/vehicle combination can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res. 5:2330-2337 and Barry et al., International PCT Publication No. WO 99/31262. Many examples in the art describe delivery methods of oligonucleotides by osmotic pump, (see Chun et al., 1998, Neuroscience Letters 257:135-138, D'Aldin et al., 1998, Mol. Brain Research 55:151-164, Dryden et al., 1998, J. Endocrinol. 157:169-175, Ghirnikar et al., 1998, Neuroscience Letters 247:21-24) or direct infusion (Broaddus et al., 1997, Neurosurg. Focus 3, article 4). Other delivery routes include, but are not limited to, oral delivery (such as in tablet or pill form) and/or intrathecal delivery (Gold, 1997, Neuroscience 76:1153-1158). More detailed descriptions of nucleic acid delivery and administration are provided in Sullivan et al., PCT WO 94/02595, Draper et al., PCT WO93/23569, Beigelman et al., PCT WO99/05094, and Klimuk et al., PCT WO99/04819, all of which are incorporated by reference herein.

Alternatively, certain siRNA molecules of the invention can be expressed within cells from eukaryotic promoters (see for example, Izant and Weintraub, 1985, Science 229:345; McGarry and Lindquist, 1986, Proc. Natl. Acad. Sci USA 83:399; Scanlon et al., 1991, Proc. Natl. Acad. Sci. USA 88:10591-5; Kashani-Sabet et al., 1992, Antisense Res. Dev. 2:3-15; Dropulic et al., 1992, J. Virol. 66:1432-41; Weerasinghe et al., 1991, J. Virol. 65:5531-4; Ojwang et al., 1992, Proc. Natl. Acad. Sci. USA 89:10802-6; Chen et al., 1992, Nucleic Acids Res. 20:4581-9; Sarver et al., 1990, Science 247:1222-1225; Thompson et al., 1995, Nucleic Acids Res. 23:2259; Good et al., 1997, Gene Therapy 4: 45. Those skilled in the art will recognize that any nucleic acid can be expressed in eukaryotic cells using the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595; Ohkawa et al., 1992, Nucleic Acids Symp. Ser. 27:15-6; Taira et al., 1991, Nucleic Acids Res. 19:5125-30; Ventura et al., 1993, Nucleic Acids Res. 21:3249-55; Chowrira et al., 1994, J. Biol. Chem. 269: 25856).

In another aspect of the invention, RNA molecules of the invention can be expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, but not limited to, adeno-associated virus, retrovirus, adenovirus, or alphavirus. In another embodiment, pol III based constructs are used to express nucleic acid molecules of the invention (see for example, Thompson, U.S. Pat. Nos. 5,902,880 and 6,146,886). The recombinant vectors capable of expressing the siRNA molecules can be delivered as described above, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response. Delivery of siRNA molecule expressing vectors can be systemic, such as by intravenous or intramuscular administration, by administration to target cells ex-planted from a subject followed by reintroduction into the subject, or by any other means that would allow for introduction into the desired target cell (for a review, see Couture et al., 1996, TIG. 12:510).

In certain embodiments, the invention provides expression vectors comprising a nucleic acid sequence encoding at least one siRNA molecule of the invention. The expression vector can encode one or both strands of a siRNA duplex, or a single self-complementary strand that self hybridizes into an siRNA duplex. The nucleic acid sequences encoding the siRNA molecules can be operably linked in a manner that allows expression in a cell of the siRNA molecule (see for example, Paul et al., 2002, Nature Biotechnology 19:505; Miyagishi and Taira, 2002, Nature Biotechnology 19:497; Lee et al., 2002, Nature Biotechnology 19:500; and Novina et al., 2002, Nature Medicine, online publication June 3).

In other aspects, the invention provides expression vectors comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siRNA molecules of the invention; wherein said sequence is operably linked to said initiation region and said termination region, in a manner that allows expression and/or delivery of the siRNA molecule. The vector can optionally include an open reading frame (ORF) for a protein operably linked on the 5' side or the 3'-side of the sequence encoding the siRNA of the invention; and/or an intron (intervening sequences).

Transcription of siRNA molecules can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA 87:6743-7; Gao and Huang 1993, Nucleic Acids Res. 21:2867-72; Lieber et al., 1993, Methods Enzymol. 217:47-66; Zhou et al., 1990, Mol Cell Biol. 10:4529-37). Several investigators have demonstrated that nucleic acid molecules expressed from such promoters can function in mammalian cells (e.g. Kashani-Sabet et al., 1992, Antisense Res. Dev. 2:3-15; Ojwang et al., 1992, Proc. Natl. Acad. Sci. USA 89:10802-6; Chen et al., 1992, Nucleic Acids Res. 20:4581-9; Yu et al., 1993, Proc. Natl. Acad. Sci. USA 90:6340-4; L'Huillier et al., 1992, EMBO J. 11:4411-8; Lisziewicz et al., 1993, Proc. Natl. Acad. Sci. U.S.A. 90:8000-4; Thompson et al., 1995, Nucleic Acids Res. 23:2259; Sullenger and Cech, 1993, Science 262:1566). More specifically, transcription units such as the ones derived from genes encoding U6 small nuclear (snRNA), transfer RNA (tRNA) and adenovirus VA RNA are useful in generating high concentrations of desired RNA molecules such as siRNA in cells (Thompson et al., 1995, Nucleic Acids. Res. 23:2259; Couture et al., 1996, TIG 12:510, Noonberg et al., 1994, Nucleic Acid Res. 22:2830; Noonberg et al., U.S. Pat. No. 5,624,803; Good et al., 1997, Gene Ther. 4:45; Beigelman et al., International PCT Publication No. WO 96/18736. The above siRNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavilis vectors) (for a review see Couture et al., 1996, TIG 12:510).

Expression vectors that are useful in the practice of the invention include expression vectors that comprise a nucleic acid sequence encoding two complementary sequences of an siRNA molecule separated by a small nucleotide spacer sequence, in a manner that allows expression of that siRNA molecule containing a hairpin loop. Generally, a useful expression vector comprises: a) a transcription initiation region; b) a transcription termination region; and c) a nucleic acid sequence encoding two complementary sequences of an siRNA molecule separated by a small nucleotide spacer sequence; wherein the sequence is operably linked to the initiation region and the termination region, in a manner that allows expression and/or delivery of the siRNA molecule containing the small hairpin loop.

In certain embodiments, the invention provides a method of inhibiting tumor growth in an animal comprising administering to the animal, which has at least one tumor cell present in its body, a therapeutically effective amount of an EVI1 siRNA molecule as provided herein for a therapeutically effective period of time, wherein the EVI1 siRNA molecule can inhibit EVI1 gene expression.

In certain embodiments, the invention provides pharmaceutical compositions comprising a therapeutically effective amount of an EVI1 siRNA molecule as provided herein that inhibits EVI1 expression in mammalian cells together with a pharmaceutically acceptable diluent, carrier, solubilizer, emulsifier, preservative and/or adjuvant. The invention further provides pharmaceutical compositions comprising an EVI1 siRNA molecule as provided herein.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (Such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing Company.

Optimal pharmaceutical compositions can be determined by one skilled in the art depending upon, for example, the intended route of administration, delivery format and desired dosage. See, for example, REMINGTON'S PHARMACEUTICAL SCIENCES, Id. Such compositions may influence the physical state, stability, rate of in vivo release and rate of in vivo clearance of the antibodies of the invention.

Primary vehicles or carriers in a pharmaceutical composition can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefor. Pharmaceutical compositions of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the EVI1-inhibiting siRNA may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical compositions of the invention can be delivered parenterally. When parenteral administration is contemplated, the therapeutic compositions for use in this invention may be in the form of a pyrogen-free, parenterally acceptable aqueous solution comprising the desired siRNA of the invention. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may be formulated for inhalation. In these embodiments, a compound identified in a screening method of the invention or an EVI1 siRNA disclosed herein is formulated as a dry powder for inhalation, or inhalation solutions may also be formulated with a propellant for aerosol delivery, such as by nebulization Pulmonary administration is further described in PCT Application No. PCT/US94/001875, which describes pulmonary delivery of chemically modified proteins and is incorporated by reference.

The pharmaceutical compositions of the invention can be delivered through the digestive tract, such as orally. The preparation of such pharmaceutically acceptable compositions is within the skill of the art. An EVI1 siRNA disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption of the EVI1 siRNA disclosed herein. Diluents, flavorings, low melting point waxes, vegetable oils, lubricants, suspending agents, tablet disintegrating agents, and binders may also be employed.

A pharmaceutical composition may involve an effective quantity of an EVI1 siRNA disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are evident to those skilled in the art, including formulations involving an EVI1 inhibitor disclosed herein or compounds of the invention in sustained- or controlled-delivery formulations. Techniques for formulating a variety of other sustained- or controlled-delivery means, such as liposome carriers, bioerodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, Biopolymers 22: 547-556), poly(2-hydroxyethyl-methacrylate) (Langer et al., 1981, J. Biomed. Mater. Res. 15: 167-277) and Langer, 1982, Chem. Tech. 12: 98-105), ethylene vinyl acetate (Langer et al., id.) or poly-D(-)-3-hydroxybutyric acid (EP 133.988). Sustained release compositions may also include liposomes, which can be prepared by any of several methods known in the art. See e.g., Eppstein et al., 1985, Proc. Natl. Acad. Sci. USA 82: 3688-3692; EP 036,676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The present invention is directed to kits for producing a single-dose administration unit. Kits according to the invention may each contain both a first container having a dried proteins compound identified in a screening method of the invention and a second container having an aqueous formulation, including for example single and multi-chambered pre-filled syringes (e.g., liquid syringes, lyosyringes or needle-free syringes).

The effective amount of a pharmaceutical composition of the invention to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the pharmaceutical composition is being used, the route of administration, and the size (body weight, body surface or organ size) and/or condition (the age and general health) of the patient. A clinician may titer the dosage and modify the route of administration to obtain the optimal therapeutic effect.

The dosing frequency will depend upon the pharmacokinetic parameters of an EVI1 siRNA disclosed herein. For example, a clinician administers the siRNA until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Administration routes for the pharmaceutical compositions of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In certain embodiments, it may be desirable to use an EVI1 siRNA disclosed herein or pharmaceutical compositions comprising an EVI1 siRNA of the invention in an ex vivo manner. In such instances, cells, tissues or organs that have been removed from the patient are exposed to pharmaceutical compositions of the invention or an siRNA disclosed herein after which the cells, tissues and/or organs are subsequently implanted back into the patient.

Pharmaceutical compositions of the invention can be administered alone or in combination with other therapeutic agents, in particular, in combination with other cancer therapy agents. Such agents generally include radiation therapy or chemotherapy. Chemotherapy, for example, can involve treatment with one or more of the following agents: anthracyclines, taxol, tamoxifene, doxorubicin, 5-fluorouracil, and other drugs known to one skilled in the art.

Introducing an siRNA of the invention into cells can be accomplished using any method known in the art or as described herein. For example, local delivery of an EVI1 siRNA can be accomplished by direct injection or by other appropriate viral or non-viral delivery vectors. (Hefti, 1994, Neurobiology 25:1418-35.) For example, a nucleic acid molecule encoding an EVI1 polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome used according to the teachings of the invention typically contains AAV inverted terminal repeats flanking a DNA sequence encoding an EVI1 siRNA operatively linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), and U.S. Pat. No. 5,635,399 (involving retroviral vectors expressing cytokines).

Nonviral delivery methods include, but are not limited to, liposome-mediated transfer, naked DNA delivery (e.g., by direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles aye propelled at cells at a speed whereby the particles penetrate the surface of the cells and become incorporated into the interior of the cells), and PCT Pub. No. WO 96/40958 (involving nuclear ligands).

The following Examples illustrate certain aspects of the above-described method and advantageous results. The following examples are shown by way of illustration and not by way of limitation.

EXAMPLES

Figure 4:
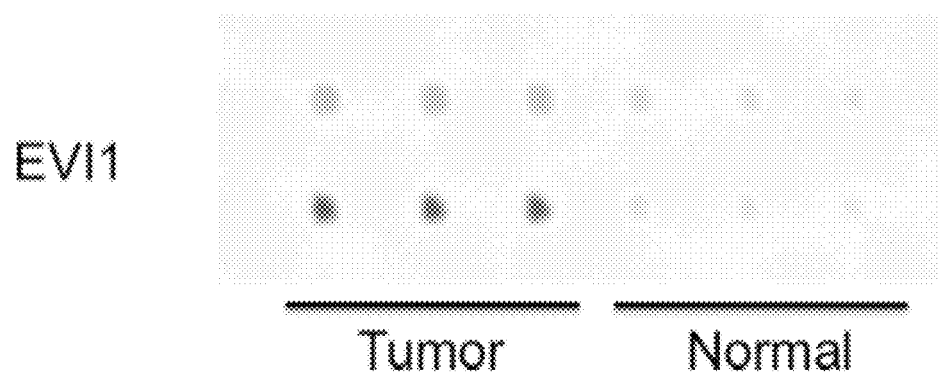
FIG. 4 is a photomicrograph of a microarray showing an example of tumor-specific expression of EVI1 in ovarian squamous cell carcinoma. Homogenates of tumor tissue (left) and adjacent normal tissue (right) are spotted onto a polyvinyldifluoride membrane in triplicate in SomaPlex™ Cancer Tissue Lysate Protein Microarray Slides (Gentel, Madison, Wis.).
Figure 5:
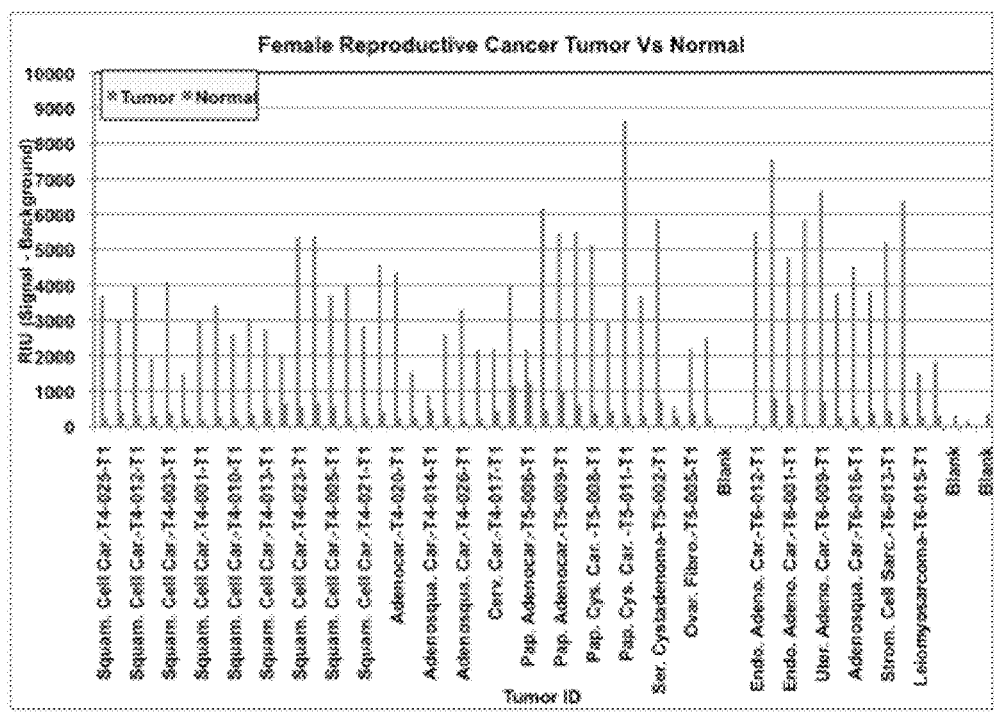
FIG. 5 is a graph showing relative expression of EVI1 in 24 tumors of the female reproductive tract compared to normal tissue from the same subject.

For the inventions described herein, nucleotide molecules that disrupt the function of EVI1 are used to reduce tumor burden and size of tumors in vivo. EVI1 is over-expressed in cancerous cells, and not expressed in non-cancerous cells. For example, EVI1 is over-expressed in tumors of the female reproductive tract (FIGS. 4 and 5). Homogenates of tumor tissue (left) and adjacent normal tissue (right) are spotted onto a polyvinyldifluoride membrane in triplicate in SomaPlex™ Cancer Tissue Lysate Protein Microarray Slides (Gentel, Madison, Wis.). The array was probed with an anti-EVI1 monoclonal antibody purchased from Cell Signaling. The EVI1 levels in the tissue homogenates were visualized using a sliver-coated goat-anti mouse secondary antibody. Densitometric volumes representing the amount of EVI1 protein in each spot were quantified using photographic scanning and relative expression displayed graphically in FIG. 5. EVI1 was found to be highly elevated in tumor samples from the female reproductive tissues compared to adjacent normal tissue from the same subject. These results suggest that over-expression of EVI1 is associated with tumorigenic properties of the tissues and is a putative anti-cancer target.

Polymerase Chain Reaction (PCR) Assays:

PCR assays are performed to detect changes in EVI1 gene expression in the presence of the siRNA reagents described herein. For these assays, PCR reaction conditions used are a melting temperature of 95° for 60 sec; thermocycling at 95° C., for 30 sec, 60° C., for 30 sec, and 72° C., for 30 sec, for 25-30 cycles, and elongation 72° C. for 60 sec.

In these assays, total RNA is isolated using a Fermentas GeneJET kit. Quantitative PCR (qPCR) is carried out using target-specific probes and primers obtained from IDT. Primers and reporters for EVI1 and β-actin mRNA are designed using the CloneManager program. The sequences of forward and reverse primers are shown in the below. PCR template is prepared using ThermoFisher Verso cDNA synthesis kit. All qPCR reagents are validated by demonstrating a linear relationship between sample concentration and amplification kinetics over a three-log range of nucleic acid concentrations, using cDNA made from total RNA. Taqman Universal Master Mix (Fermentas) is used for PCR reactions and amplification data are collected using an ABI Prism 7900 Sequence Detector and analyzed using the Sequence Detection System software (SDS V2.0) from ABI. Unless stated otherwise, abundance of mRNA is calculated by normalization to β-actin $\Delta C_T = C_{Ttarget} - C_{T\beta\text{-}actin}$ and calibrated to mRNA abundance in untreated tumor cells ($\Delta\Delta CT = \Delta C_{TEVIRNA} \Delta C_{TsiGlo}$). Data are represented as $2^{-\Delta\Delta CT}$, such that the abundance of the individual mRNAs in HT-29 is expressed as 1.0 ($\Delta C_{THT\text{-}29}=0$, and $2^{-0}=1.0$). The abundance of EVI1 mRNA in colon cancer cells is normalized to β-actin and calibrated to HFC cells. Statistical analysis for QPCR results is carried out using the Mann-Whitney Rank Sum analytical function of Sigma Stat.

| Primer | Sequence (5' to 3') | Fragment Size |
|---|---|---|
| EVI1 12-14 F | AAGGCATGTTCGCAACATCC (SEQ ID NO: 203) | 458 bp |
| EVI1 12-14 R | TAGTCATCCTCAGGGTTTCC (SEQ ID NO: 204) | 458 bp |
| β-actin F | GGGAAATCGTGCGTGACATTAAG (SEQ ID NO: 205) | 275 bp |

| Primer | Sequence (5' to 3') | Fragment Size |
|---|---|---|
| β-actin R | TGTGTTGGCGTACAGGTCTTTG (SEQ ID NO: 206) | 275 bp |

Example 1

In a preferred embodiment of the invention, the EVI1 inhibitor is a 21 bp small interfering RNA (siRNA). In silico analysis of the human EVI1 isoform 1b mRNA was performed using algorithms that identify potentially potent siRNAs capable of silencing EVI1 expression. Five core target sequences to which siRNAs provide potent EVI1 down-regulators are presented in Table 1 (SEQ ID NOs: 2-6). The corresponding siRNAs to these target sites A (SEQ ID NOs: 7-8), B (SEQ ID NOs: 9-10), C (SEQ ID NOs: 11-12), D (SEQ ID NOs: 13-14), and E (SEQ ID NOs: 15-16) are presented in Table 2. Sequences focused around the 256 core (SEQ ID NO 2) are presented in Table 3 (SEQ ID NOs 17-56). Sequences focused around the 979 core (SEQ ID NO 3) and the 992 core (SEQ ID NO 4) are presented in Table 4 (SEQ ID NOs 57-120). Sequences focused around the 2910 core (SEQ ID NO 5) are presented in Table 5 (SEQ ID NOs 121-160). Sequences focused around the 2994 core (SEQ ID NO 6) are presented in Table 6 (SEQ ID NOs 161-200).

Each of the five siRNA duplexes presented in Table 2 were introduced into cultures of ovarian tumor cells at a concentration of 50 nM. The properties of the ovarian tumor cells tested are shown in Table 4. Briefly, fifty to one hundred thousand tumor cells were added to each well of a 6 well plate and allowed to attach to the surface and grow for 18 hours in DMEM medium containing 10% fetal bovine serum. A total of 100 pmol of each siRNA was introduced into cells using 1 microliter DharmaFECT (Thermo Scientific) reagent in 2 ml total volume of media. Cells were incubated with the siRNA for 96 hours. The viability of the ovarian tumor cells was assessed by counting cells with a hemocytometer following trypan blue exclusion staining Results are presented in Table 5. Each of the five sequences reduced the number of viable cells at least 40% (compared to control siRNA-treated cells) in at least one ovarian tumor cell line.

Example 2

Figure 7B:
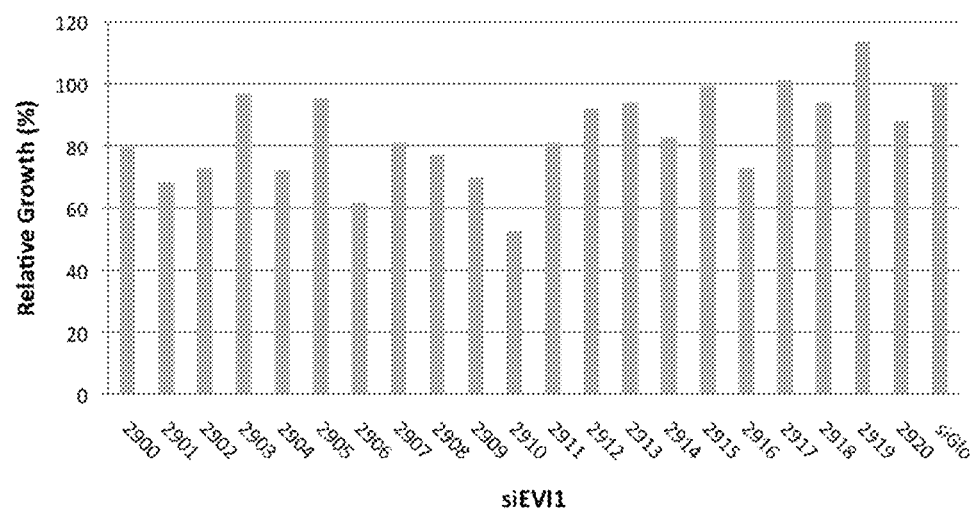
Figure 8:
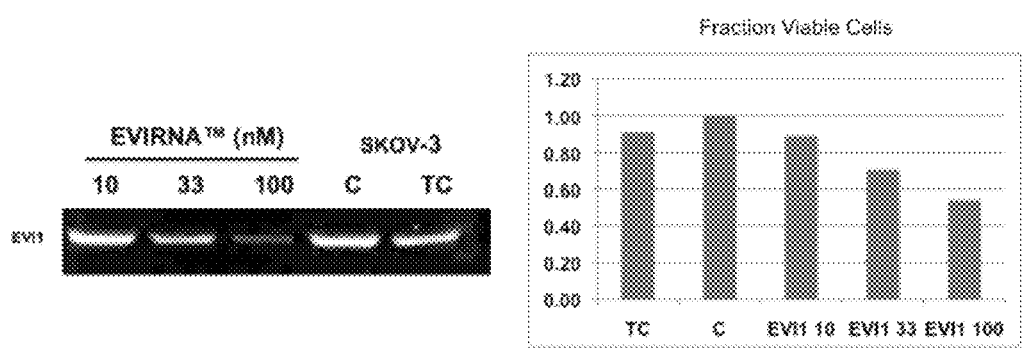
FIG. 8 shows a photograph (left panel) of immunoblot analysis and inhibition of tumor cell growth by anti-EVI1 siRNA. Ovarian tumor cells SKOV3 were seeded into each well of a 6 well plate. Increasing concentrations of siRNA were introduced into the cells using 2 microliter of Dharmafect reagent in 4 ml of medium. The number of viable cells was determined using trypan blue staining and counting in a hemacytometer. Nuclear protein was isolated form the cells and the amount of EVI1 present was detected using anti-EVI1 polyclonal antibody and visualized using goat anti-rabbit HRP conjugate and a chemiluminescent peroxidase stain. The right panel of FIG. 8 is a bar graph reflecting tumor cell growth inhibition by the siRNAs used in experiments used for the immunoblots show in the left panel.

For a substance to be an effective cancer therapeutic agent, it needs a robust cancer killing effect at very low concentrations, which for siRNA will be understood to be at subnanomolar concentrations in cell culture. The concentration of siRNA that inhibited growth of ovarian tumor cells by 50% ($IC_{50}$) was determined by measuring cell viability 96 hours after adding one of various dose levels of siRNA to identical numbers of tumor cells in culture. FIG. 6A shows the $IC_{50}$ of siEVI1-979 (SEQ ID NOs 9-10) for ES-2 cells is ~2.5 nM, and the $IC_{50}$ of siEVI1-2910 (SEQ ID NOs 13-14) is ~0.5 nM. For TOV-112D cells, the $IC_{50}$ of siEVI1-979 (SEQ ID NOs 9-10) is ~4 nM, and the $IC_{50}$ of siEVI1-2910 (SEQ ID NOs 13-14) is ~0.8 nM. To further identify potent sequences that inhibit the growth of ovarian tumor cells, sequences of up to 10 bp upstream and 10 bp downstream of siEVI1-2910 (SEQ ID NOs: 121-160) were prepared and administered to ES-2 and TOV-112D ovarian tumor cells at a concentration of 2.5 nM using DharmaFECT transfection reagent. FIG. 7A depicts the results of percent growth inhibition of TOV-112D ovarian tumor cells relative to a transfection control. The siRNA sequences (SEQ ID NOs: 121-124, 127-132, 133-136, and 137-138) were found to inhibit growth of TOV-112D ovarian tumor cells at concentrations at or below 2.5 nM. FIG. 7B depicts the results of percent growth inhibition of ES-2 ovarian tumor cells relative to a transfection control. The siRNA sequences (SEQ ID NOs: 121-126, 129-130, 133-142-147-148, and 151-152) were found to inhibit growth of ES-2 ovarian tumor cells at concentrations at or below 2.5 nM.

Example 3

Potent siRNA inhibitors of EVI1 can reduce the growth of tumors in mice following direct injection into the tumors. To assess siRNA potency, three million ovarian metastatic tumor cells are injected into female nude mice subcutaneously and tumors permitted to grow over a period of ten days. Up to five injections of 10 microliters each containing 1 nmol siRNA encapsulated into liposome nanoparticle are injected immediately underneath the tumors twice weekly for three weeks. An equal number of mice bearing similar tumors are injected with nanoparticle containing a scrambled siRNA sequence as a negative control. The tumors are removed after three weeks of dosing and measured and weighed. For potent siRNA species, tumors in mice dosed with siRNA targeting EVI1 are expected to have tumors averaging ~10% the size of those dosed with scrambled siRNA sequence. These results provide a demonstration of the efficacy and potency of the siRNA targeting EVI1 as an anticancer therapy. Overall expression of EVI1 in the tumors are expected to be decreased by more than 70% as evidenced, for example, by Western blot of the tumor homogenate probed with anti-EVI1 antibody. Expression of EVI1 mRNA is also expected to be diminished several fold as evidenced by quantitative PCR analysis of EVI1 gene expression with primers that amplify a 300 bp region of EVI1 exon 14.

Example 4

For effective embodiments of the reagents of the invention, siRNA reduce the growth of tumors in mice following direct injection into the tumors at subnanomolar concentrations. To assess siRNA potency, three million ovarian metastatic tumor cells are injected into female nude mice intraperitoneally and tumors permitted to grow over a period of twenty-one days. An amount of 100 microliters of 1 nmol siRNA encapsulated into liposome nanoparticles is injected into the mouse tail vein twice a week for three weeks. An equal number of mice bearing similar tumors are injected with nanoparticles containing a scrambled siRNA sequence as a negative control. Tumors are removed after three weeks of dosing, measured and weighed. For potent siRNA species, tumors from mice dosed with siRNA targeting EVI1 are expected to have tumors averaging ~10% the size of those from mice dosed with a scrambled siRNA sequence. These results provide a demonstration of the efficacy and potency of the siRNA targeting EVI1 as an anticancer therapy. Overall expression of EVI1 in the tumors are expected to be decreased by more than 70% as evidenced, for example, by Western blot of the tumor homogenate probed with anti-EVI1 antibody. Expression of EVI1 mRNA is also expected to be diminished several fold as evidenced by quantitative PCR analysis of EVI1 gene expression with primers that amplify a 300 bp region of EVI1 exon14.

Example 5

As set forth herein, small interfering RNA (siRNAs) are provided from in silico analysis of the human EVI1 isoform 1b mRNA, performed using algorithms that identify potentially potent siRNAs capable of silencing EVI1 expression. Five core target sequences to which siRNAs provide potent EVI1 down-regulators are presented in Table 1 (SEQ ID NOs: 2-6). The corresponding siRNAs to these target sites A (SEQ ID NOs: 7-8), B (SEQ ID NOs: 9-10), C (SEQ ID NOs: 11-12), D (SEQ ID NOs: 13-14), and E (SEQ ID NOs: 15-16) are presented in Table 2. Sequences focused around the 256 core (SEQ ID NO 2) are presented in Table 3 (SEQ ID NOs 17-56). Sequences focused around the 979 core (SEQ ID NO 3) and the 992 core (SEQ ID NO 4) are presented in Table 4 (SEQ ID NOs 57-120). Sequences focused around the 2910 core (SEQ ID NO 5) are presented in Table 5 (SEQ ID NOs 121-160). Sequences focused around the 2994 core (SEQ ID NO 6) are presented in Table 6 (SEQ ID NOs 161-200).

Each of the five siRNA duplexes presented in Table 2 were introduced into cultures of prostate tumor cells at a concentration of 50 nM. The properties of said prostate tumor cells tested are shown in Table 9. Briefly, fifty to one hundred thousand tumor cells were added to each well of a 6 well plate and allowed to attach to the surface and grow for 18 hours in DMEM medium containing 10% fetal bovine serum. A total of 200 picomol of each siRNA was introduced into cells using 1 microliter DharmaFECT reagent in 2 ml total volume of media. Cells were incubated with the siRNA for 96 hours. The viability of the prostate tumor cells was assessed by counting cells with a hemocytometer following trypan blue exclusion staining Results are presented in Table 10. Each of the five sequences reduced the number of viable cells at least 40% (compared to control siRNA-treated cells) in at least one prostate tumor cell line.

Example 6

For a substance to be an effective cancer therapeutic agent, it needs a robust cancer killing effect at very low concentrations, which for siRNA will be understood to be at subnanomolar concentrations in cell culture. The concentration of siRNA that inhibited growth of prostate tumor cells by 50% ($IC_{50}$) was determined by measuring cell viability 96 hrs after adding increasing doses of siRNA to identical numbers of tumor cells in culture.

Example 7

Each of the five siRNA duplexes presented in Table 2 were introduced into cultures of breast tumor cells at a concentration of 50 nM. The properties of the breast tumor cells tested are shown in Table 11. Briefly, fifty to one hundred thousand tumor cells were added to each well of a 6 well plate and allowed to attach to the surface and grow for 18 hours in DMEM medium containing 10% fetal bovine serum. A total of 200 picomol of each siRNA was introduced into cells using 1 microliter DharmaFECT reagent in 2 ml total volume of media. Cells were incubated with the siRNA for 96 hours. The viability of the breast tumor cells was assessed by counting cells with a hemocytometer following trypan blue exclusion. Results are presented in Table 12. Each of the five sequences reduced the number of viable cells at least 40% (compared to control siRNA-treated cells) in at least one ovarian tumor cell line.

Example 8

The concentration of siRNA that inhibited growth of breast tumor cells by 50% ($IC_{50}$) was determined by measuring cell viability 96 hrs after adding increasing doses of siRNA to identical numbers of tumor cells in culture.

Example 9

For effective embodiments of the reagents of the invention, siRNA reduce the growth of tumors in mice following direct injection into the tumors at subnanomolar concentrations. To further assess siRNA potency, three million prostate metastatic tumor cells were injected into female nude mice subcutaneously and tumors permitted to grow over a period of ten days. Up to five injections of 10 microliters each containing 1 nmol siRNA encapsulated into liposome nanoparticle was injected immediately underneath the tumors twice weekly for three weeks. An equal number of mice bearing similar tumors were injected with nanoparticle containing a scrambled siRNA sequence as a negative control. Tumors were removed after three weeks of dosing, measured and weighed. Tumors in mice dosed with siRNA targeting EVI1 had tumors averaging 10% the size of those dosed with scrambled siRNA sequence. The results demonstrate the efficacy and potency of the siRNA targeting EVI1 as an anticancer therapy. The overall expression of EVI1 in the tumors was decreased by more than 70% as evidenced by Western blot of the tumor homogenate probed with anti-EVI1 antibody. The expression of EVI1 mRNA was also diminished several fold as evidenced by quantitative PCR analysis of EVI1 gene expression with primers that amplify a 300 bp region of EVI1 exon 14.

Example 10

To further assess siRNA potency, three million prostate metastatic tumor cells were injected into female nude mice intraperitoneally and tumors permitted to grow over a period of twenty-one days. An amount of 100 microliters of 1 nmol siRNA encapsulated into liposome nanoparticle was injected into the mouse tail vein twice a week for three weeks. An equal number of mice bearing similar tumors were injected with nanoparticle containing a scrambled siRNA sequence as a negative control. Tumors were removed after three weeks of dosing, measured and weighed. Tumors from mice dosed with siRNA targeting EVI1 averaged ~10% the size of those from mice dosed with scrambled siRNA sequence. The results demonstrated the efficacy and potency of the siRNA targeting EVI1 as an anticancer therapy. Overall expression of EVI1 in these tumors was decreased by more than 70% as evidenced by Western blot analysis of the tumor homogenate probed with anti-EVI1 antibody. The expression of EVI1 mRNA was also diminished several fold as evidenced by quantitative PCR analysis of EVI1 gene expression with primers that amplify a 300 bp region of EVI1 exon14.

Example 11

Each of the five siRNA duplexes presented in Table 2 are introduced into cultures of lung tumor cells at a concentration of 50 nM. The properties of the lung tumor cells tested are shown in Table 13. Briefly, fifty to one hundred thousand tumor cells are added to each well of a 6 well plate and allowed to attach to the surface and grow for 18 hours in DMEM medium containing 10% fetal bovine serum. A total of 200 picomol of each siRNA is introduced into cells using 1 microliter DharmaFECT reagent in 2 ml total volume of media. Cells are incubated with the siRNA for 96 hours. Lung tumor cell viability is assessed by counting cells with a hemocytometer following trypan blue exclusion staining.

Each of the five sequences is expected to reduce the number of viable cells at least 40% (compared to control siRNA-treated cells) in at least one lung tumor cell line.

Example 12

The concentration of siRNA that inhibited growth of lung tumor cells by 50% ($IC_{50}$) is determined by measuring cell viability 96 hrs after adding increasing doses of siRNA to identical numbers of tumor cells in culture.

Example 13

To further assess siRNA potency, three million lung metastatic tumor cells are injected into female nude mice subcutaneously and tumors permitted to grow over a period of ten days. Up to five injections of 10 microliters each containing 1 nmol siRNA encapsulated into liposome nanoparticle was injected immediately underneath the tumors twice weekly for three weeks. An equal number of mice bearing similar tumors were injected with nanoparticle containing a scrambled siRNA sequence as a negative control. The tumors were removed after three weeks of dosing, measured and weighed. Tumors in mice dosed with siRNA targeting EVI1 averaged ~10% the size of those mice dosed with scrambled siRNA sequence. The results demonstrated the efficacy and potency of siRNA targeting EVI1 as an anticancer therapy. Overall expression of EVI1 in the tumors was decreased by more than 70% as evidenced by Western blot of the tumor homogenate probed with anti-EVI1 antibody. Expression of EVI1 mRNA was also diminished several fold as evidenced by quantitative PCR analysis of EVI1 gene expression with primers that amplify a 300 bp region of EVI1 exon 14.

Example 14

To further assess siRNA potency, three million lung metastatic tumor cells were injected into female nude mice intraperitoneally and tumors permitted to grow over a period of twenty-one days. An amount of 100 microliters of 1 nmol siRNA encapsulated into liposome nanoparticles was injected into the mouse tail vein twice a week for three weeks. An equal number of mice bearing similar tumors were injected with nanoparticle containing a scrambled siRNA sequence as a negative control. Tumors were removed after three weeks of dosing, measured and weighed. Tumors from mice dosed with siRNA targeting EVI1 averaged ~10% the size of those from mice dosed with scrambled siRNA sequence. These results demonstrated the efficacy and potency of the siRNA targeting EVI1 as an anticancer therapy. The overall expression of EVI1 in the tumors was decreased by more than 70% as evidenced by Western blot of the tumor homogenate probed with anti-EVI1 antibody. The expression of EVI1 mRNA was also diminished several fold as evidenced by quantitative PCR analysis of EVI1 gene expression with primers that amplify a 300 bp region of EVI1 exon14.

Example 15

Each of the five siRNA duplexes presented in Table 2 are introduced into cultures of colon tumor cells at a concentration of 50 nM. The properties of the colon tumor cells tested are shown in Table 14. Briefly, fifty to one hundred thousand tumor cells are added to each well of a 6 well plate and allowed to attach to the surface and grow for 18 hours in DMEM medium containing 10% fetal bovine serum. A total of 200 picomol of each siRNA is introduced into cells using 1 microliter DharmaFECT reagent in 2 ml total volume of media. Cells are incubated with the siRNA for 96 hours. Colon tumor cell viability is assessed by counting cells with a hemocytometer following trypan blue exclusion staining. Each of the five sequences are expected to reduce the number of viable cells at least 40% (compared to control siRNA-treated cells) in at least one colon tumor cell line.

Example 16

For a substance to be an effective cancer therapeutic agent, it needs a robust cancer killing effect at very low concentrations, which for siRNA will be understood to be at subnanomolar concentrations in cell culture. The concentration of siRNA that inhibit growth of colon tumor cells by 50% ($IC_{50}$) was determined by measuring cell viability 96 hrs after adding increasing doses of siRNA to identical numbers of tumor cells in culture.

Example 17

To further assess siRNA potency, three million colon metastatic tumor cells are injected into female nude mice subcutaneously and tumors permitted to grow over a period of ten days. Up to five injections of 10 microliters each containing 1 nmol siRNA encapsulated into liposome nanoparticles are injected immediately underneath the tumors twice weekly for three weeks. An equal number of mice bearing similar tumors are injected with nanoparticle containing a scrambled siRNA sequence as a negative control. Tumors are removed after three weeks of dosing, measured and weighed. Tumors in mice dosed with siRNA targeting EVI1 are expected to average ~10% the size of tumors from mice dosed with scrambled siRNA sequence. The results are expected to demonstrate the efficacy and potency of the siRNA targeting EVI1 as an anticancer therapy. Overall expression of EVI1 in the tumors is expected to be decreased by more than 70% as evidenced, for example, by Western blot of the tumor homogenate probed with anti-EVI1 antibody. Expression of EVI1 mRNA is also expected to be diminished several fold as evidenced by quantitative PCR analysis of EVI1 gene expression with primers that amplify a 300 bp region of EVI1 exon 14.

Example 18

To further assess siRNA potency, three million colon metastatic tumor cells are injected into female nude mice intraperitoneally and tumors permitted to grow over a period of twenty-one days. An amount of 100 microliters of 1 nmol siRNA encapsulated into liposome nanoparticles is injected into the mouse tail vein twice a week for three weeks. An equal number of mice bearing similar tumors are injected with nanoparticles containing a scrambled siRNA sequence as a negative control. Tumors are removed after three weeks of dosing, measured and weighed. Tumors from mice dosed with siRNA targeting EVI1 are expected to average ~10% the size of tumors from mice dosed with scrambled siRNA sequence. These results are expected to demonstrate the efficacy and potency of the siRNA targeting EVI1 as an anticancer therapy. Overall expression of EVI1 in the tumors is expected to be decreased by more than 70% as evidenced, for example, by Western blot of the tumor homogenate probed with anti-EVI1 antibody. The expression of EVI1 mRNA is also expected to be diminished several fold as evidenced by quantitative PCR analysis of EVI1 gene expression with primers that amplify a 300 bp region of EVI1 exon14.

Example 19

To further assess siRNA potency, three million breast metastatic tumor cells were injected into female nude mice subcutaneously and tumors permitted to grow over a period of ten days. Up to five injections of 10 microliters each containing 1 nmol siRNA encapsulated into liposome nanoparticles was injected immediately underneath the tumors twice weekly for three weeks. An equal number of mice bearing similar tumors were injected with nanoparticles containing a scrambled siRNA sequence as a negative control. Tumors were removed after three weeks of dosing, measured and weighed. Tumors in mice dosed with siRNA targeting EVI1 averaged ~10% the size of tumors from mice dosed with scrambled siRNA sequence. The results demonstrated the efficacy and potency of the siRNA targeting EVI1 as an anticancer therapy. The overall expression of EVI1 in the tumors was decreased by more than 70% as evidenced by Western blot of the tumor homogenate probed with anti-EVI1 antibody. The expression of EVI1 mRNA was also diminished several fold as evidenced by quantitative PCR analysis of EVI1 gene expression with primers that amplify a 300 bp region of EVI1 exon 14.

Example 20

To further assess siRNA potency, three million breast metastatic tumor cells were injected into female nude mice intraperitoneally and tumors permitted to grow over a period of twenty-one days. An amount of 100 microliters of 1 nmol siRNA encapsulated into liposome nanoparticles was injected into the mouse tail vein twice a week for three weeks. An equal number of mice bearing similar tumors were injected with nanoparticles containing a scrambled siRNA sequence as a negative control. Tumors were removed after three weeks of dosing, measured and weighed. Tumors from mice dosed with siRNA targeting EVI1 averaged ~10% the size of tumors from mice dosed with scrambled siRNA sequence. These results demonstrated the efficacy and potency of the siRNA targeting EVI1 as an anticancer therapy. The overall expression of EVI1 in the tumors was decreased by more than 70% as evidenced by Western blot of the tumor homogenate probed with anti-EVI1 antibody. Expression of EVI1 mRNA was also diminished several fold as evidenced by quantitative PCR analysis of EVI1 gene expression with primers that amplify a 300 bp region of EVI1 exon14.

Example 21

Each of the five siRNA duplexes presented in Table 2 are introduced into cultures of melanoma tumor cells at a concentration of 50 nM. The properties of the melanoma tumor cells tested are shown in Table 15. Briefly, fifty to one hundred thousand tumor cells are added to each well of a 6 well plate and allowed to attach to the surface and grow for 18 hours in DMEM medium containing 10% fetal bovine serum. A total of 200 picomol of each siRNA is introduced into cells using 1 microliter DharmaFECT reagent in 2 ml total volume of media. Cells are incubated with the siRNA for 96 hours. Melanoma tumor cell viability is assessed by counting cells with a hemocytometer following trypan blue exclusion staining. Each of the five sequences are expected to reduce the number of viable cells at least 40% (compared to control siRNA-treated cells) in at least one melanoma tumor cell line.

Example 22

The concentration of siRNA that inhibits growth of melanoma tumor cells by 50% ($IC_{50}$) is determined by measuring cell viability 96 hrs after adding increasing doses of siRNA to identical numbers of tumor cells in culture.

Example 23

To further assess siRNA potency, three million melanoma metastatic tumor cells are injected into female nude mice subcutaneously and tumors permitted to grow over a period of ten days. Up to five injections of 10 microliters each containing 1 nmol siRNA encapsulated into liposome nanoparticles are injected immediately underneath the tumors twice weekly for three weeks. An equal number of mice bearing similar tumors are injected with nanoparticles containing a scrambled siRNA sequence as a negative control. Tumors are removed after three weeks of dosing, measured and weighed. Tumors in mice dosed with siRNA targeting EVI1 are expected to average ~10% the size of tumors from mice dosed with scrambled siRNA sequence. The results are expected to demonstrate the efficacy and potency of the siRNA targeting EVI1 as an anticancer therapy. Overall expression of EVI1 in the tumors is expected to be decreased by more than 70% as evidenced, for example, by Western blot of the tumor homogenate probed with anti-EVI1 antibody. Expression of EVI1 mRNA is also expected to be diminished several fold as evidenced by quantitative PCR analysis of EVI1 gene expression with primers that amplify a 300 bp region of EVI1 exon 14.

Example 24

To further assess siRNA potency, three million melanoma metastatic tumor cells are injected into female nude mice intraperitoneally and tumors permitted to grow over a period of twenty-one days. An amount of 100 microliters of 1 nmol siRNA encapsulated into liposome nanoparticle is injected into the mouse tail vein twice a week for three weeks. An equal number of mice bearing similar tumors are injected with nanoparticle containing a scrambled siRNA sequence as a negative control. Tumors are removed after three weeks of dosing, measured and weighed. Tumors from mice dosed with siRNA targeting EVI1 are expected to average ~10% the size of tumors from mice dosed with scrambled siRNA sequence. The results are expected to demonstrate the efficacy and potency of the siRNA targeting EVI1 as an anticancer therapy. Overall expression of EVI1 in the tumors is expected to be decreased by more than 70% as evidenced, for example, by Western blot of the tumor homogenate probed with anti-EVI1 antibody. Expression of EVI1 mRNA is also expected to be diminished several fold as evidenced by quantitative PCR analysis of EVI1 gene expression with primers that amplify a 300 bp region of EVI1 exon14.

Example 25

Each of the five siRNA duplexes presented in Table 2 are introduced into cultures of HEL leukemia cells at a concentration of 50 nM. The properties of the HEL leukemia cells tested are shown in Table 16. Briefly, fifty to one hundred thousand HEL cells are added to each well of a 6 well plate and allowed to attach to the surface and grow for 18 hours in RPMI medium containing 10% fetal bovine serum. A total of 200 picomol of each siRNA is introduced into cells using 1 microliter DharmaFECT reagent in 2 ml total volume of media. Cells are incubated with the siRNA for 96 hours. Leukemia cell viability is assessed by counting cells with a hemocytometer following trypan blue exclusion staining. Each of the five sequences is expected to reduce the number of viable cells at least 40% (compared to control siRNA-treated cells) in at least one HEL leukemia tumor cell line.

Example 26

C57BL/Ly5.2 mice engrafted with EVI1 infected bone marrow cells (Buonamici, 2004) develop lethal myelodysplastic disease similar to acute myelogenous leukemia. Mice were treated with antiEVI1 siRNA in nanoparticle formulation and the degree of apoptosis in spleen and bone marrow measured and the number of Ter119 positive bone marrow cells. Mice receiving anti-EVI1 siRNA had prolonged survival and reduced numbers of Ter119 cells.

TABLE 1

Core Target Sequences of EVI1

| Description | Sequence | SEQ ID NO |
|---|---|---|
| EVI1-256 Core | 5'-ccagauaaaugaucagaua-3' | SEQ ID NO: 2 |
| EVI1-979 Core | 5'-gugcaaagacuguggacaa-3' | SEQ ID NO: 3 |
| EVI1-992 Core | 5'-ggacaaauguucagcacua-3' | SEQ ID NO: 4 |
| EVI1-2910 Core | 5'-ggaauguggaggagagaau-3' | SEQ ID NO: 5 |
| EVI1-2994 Core | 5'-augaagaaguugaagauga-3' | SEQ ID NO: 6 |

TABLE 2 siRNA Duplexes Directed to EVI1 Target Sites A, B, C, D, and E

| Description | Sequence | Strand | SEQ ID NO |
|---|---|---|---|
| siEVI1-256 or siEVI1-A | 5'-ccagauaaaugaucagauauu-3' | sense | SEQ ID NO: 7 |
|  | 3'-uuggucuauuuacuagucuau-5' | antisense | SEQ ID NO: 8 |
| siEVI1-979 or siEVI1-B | 5'-gugcaaagacuguggacaauu-3' | sense | SEQ ID NO: 9 |
|  | 3'-uucacguuucugacaccuguu-5' | antisense | SEQ ID NO: 10 |
| siEVI1-992 or siEVI1-C | 5'-ggacaaauguucagcacuauu-3' | sense | SEQ ID NO: 11 |
|  | 3'-uuccuguuuacaagucgugau-5' | antisense | SEQ ID NO: 12 |
| siEVI1-2910 or siEVI1-D | 5'-ggaauguggaggagagaauuu-3' | sense | SEQ ID NO: 13 |
|  | 3'-uuccuuacaccuccucucuua-5' | antisense | SEQ ID NO: 14 |
| siEVI1-2994 or siEVI1-E | 5'-augaagaaguugaagaugauu-3' | sense | SEQ ID NO: 15 |
|  | 3'-uuuacuucuucaacuucacu-5' | antisense | SEQ ID NO: 16 |

TABLE 3 siRNA Duplexes Directed to EVI1 Target Site A and Tiled from -10 to +10 Bases of the siEVI1-A siRNA Duplex

| Description | Sequence | Strand | SEQ ID NO |
|---|---|---|---|
| siEVI1-246 or siEVI1-A -10 | 5'-uuguugcaugccagauaaauu-3' | sense | SEQ ID NO: 17 |
|  | 3'-uuaacaacguacggucuauuu-5' | antisense | SEQ ID NO: 18 |
| siEVI1-247 or siEVI1-A -9 | 5'-uguugcaugccagauaaauuu-3' | sense | SEQ ID NO: 19 |
|  | 3'-uuacaacguacggucuauuua-5' | antisense | SEQ ID NO: 20 |
| siEVI1-248 or siEVI1-A -8 | 5'-guugcaugccagauaaauguu-3' | sense | SEQ ID NO: 21 |
|  | 3'-uucaacguacggucuauuuac-5' | antisense | SEQ ID NO: 22 |
| siEVI1-249 or siEVI1-A -7 | 5'-uugcaugccagauaaaugauu-3' | sense | SEQ ID NO: 23 |
|  | 3'-uuaacguacggucuauuuacu-5' | antisense | SEQ ID NO: 24 |
| siEVI1-250 or siEVI1-A -6 | 5'-ugcaugccagauaaaugauuu-3' | sense | SEQ ID NO: 25 |
|  | 3'-uuacguacggucuauuuacua-5' | antisense | SEQ ID NO: 26 |
| siEVI1-251 or siEVI1-A -5 | 5'-gcaugccagauaaaugaucuu-3' | sense | SEQ ID NO: 27 |
|  | 3'-uucguacggucuauuuacuag-5' | antisense | SEQ ID NO: 28 |
| siEVI1-252 or siEVI1-A -4 | 5'-caugccagauaaaugaucauu-3' | sense | SEQ ID NO: 29 |
|  | 3'-uuguacggucuauuuacuagu-5' | antisense | SEQ ID NO: 30 |
| siEVI1-253 or siEVI1-A -3 | 5'-augccagauaaaugaucaguu-3' | sense | SEQ ID NO: 31 |
|  | 3'-uuuacggucuauuuacuagu-5' | antisense | SEQ ID NO: 32 |
| siEVI1-254 or siEVI1-A -2 | 5'-ugccagauaaaugaucagauu-3' | sense | SEQ ID NO: 33 |
|  | 3'-uuacggucuauuuacuagucu-5' | antisense | SEQ ID NO: 34 |

TABLE 3-continued siRNA Duplexes Directed to EVI1 Target Site A and Tiled from −10 to +10 Bases of the siEVI1-A siRNA Duplex

| Description | Sequence | Strand | SEQ ID NO |
|---|---|---|---|
| siEVI1-255 or siEVI1-A −1 | 5'-gccagauaaaugaucagauuu-3'<br>3'-uucggucuauuuacuagucua-5' | sense<br>antisense | SEQ ID NO: 35<br>SEQ ID NO: 36 |
| siEVI1-257 or siEVI1-A +1 | 5'-cagauaaaugaucagauauuu-3'<br>3'-uugucuauuuacuagucuaua-5' | sense<br>antisense | SEQ ID NO: 37<br>SEQ ID NO: 38 |
| siEVI1-258 or siEVI1-A +2 | 5'-agauaaaugaucagauauuuu-3'<br>3'-uuucuauuuacuagucuauaa-5' | sense<br>antisense | SEQ ID NO: 39<br>SEQ ID NO: 40 |
| siEVI1-259 or siEVI1-A +3 | 5'-gauaaaugaucagauauucuu-3<br>3'-uucuauuuacuagucuauaag-5' | sense<br>antisense | SEQ ID NO: 41<br>SEQ ID NO: 42 |
| siEVI1-260 or siEVI1-A +4 | 5'-auaaaugaucagauauucuuu-3'<br>3'-uuuauuuacuagucuauaaga-5' | sense<br>antisense | SEQ ID NO: 43<br>SEQ ID NO: 44 |
| siEVI1-261 or siEVI1-A +5 | 5'-uaaaugaucagauauucuauu-3'<br>3'-uauuuacuagucuauaagau-5' | sense<br>antisense | SEQ ID NO: 45<br>SEQ ID NO: 46 |
| siEVI1-262 or siEVI1-A +6 | 5'-aaaugaucagauauucuauuu-3'<br>3'-uuuuacuagucuauaagaua-5' | sense<br>antisense | SEQ ID NO: 47<br>SEQ ID NO: 48 |
| siEVI1-263 or siEVI1-A +7 | 5'-aaugaucagauauucuauauu-3'<br>3'-uuuuacuagucuauaagauau-5 | sense<br>antisense | SEQ ID NO: 49<br>SEQ ID NO: 50 |
| siEVI1-264 or siEVI1-A +8 | 5'-augaucagauauucuauaguu-3'<br>3'-uuuacuagucuauaagauauc-5' | sense<br>antisense | SEQ ID NO: 51<br>SEQ ID NO: 52 |
| siEVI1-265 or siEVI1-A +9 | 5'-ugaucagauauucuauagauu-3'<br>3'-uuacuagucuauaagauaucu-5' | sense<br>antisense | SEQ ID NO: 53<br>SEQ ID NO: 54 |
| siEVI1-266 or siEVI1-A +10 | 5'-gaucagauauucuauagaguu-3'<br>3'-uucuagucuauaagauaucuc-5' | sense<br>antisense | SEQ ID NO: 55<br>SEQ ID NO: 56 |

TABLE 4 siRNA Duplexes Directed to EVI1 Target Sites B and C and Tiled from −10 to +10 Bases of the siEVI1-B and siEVI1-C siRNA Duplexes

| Description | Sequence | Strand | SEQ ID NO |
|---|---|---|---|
| siEVI1-969 or siEVI1-B −10 | 5'-cccaaaucaagugcaaagauu-3'<br>3'-uugguuuaguucacguuucu-5' | sense<br>antisense | SEQ ID NO: 57<br>SEQ ID NO: 58 |
| siEVI1-970 or siEVI1-B −9 | 5'-ccaaaucaagugcaaagacuu-3'<br>3'-uugguuuaguucacguuucug-5' | sense<br>antisense | SEQ ID NO: 59<br>SEQ ID NO: 60 |
| siEVI1-971 or siEVI1-B −8 | 5'-caaaucaagugcaaagacuuu-3'<br>3'-uuguuuaguucacguuucuga-5' | sense<br>antisense | SEQ ID NO: 61<br>SEQ ID NO: 62 |
| siEVI1-972 or siEVI1-B −7 | 5'-aaaucaagugcaaagacuguu-3'<br>3'-uuuuuaguucacguuucugac-5' | sense<br>antisense | SEQ ID NO: 63<br>SEQ ID NO: 64 |
| siEVI1-973 or siEVI1-B −6 | 5'-aaucaagugcaaagacuguuu-3'<br>3'-uuuuaguucacguuucugaca-5' | sense<br>antisense | SEQ ID NO: 65<br>SEQ ID NO: 66 |
| siEVI1-974 or siEVI1-B −5 | 5'-aucaagugcaaagacuguguu-3'<br>3'-uuuaguucacguuucugacac-5' | sense<br>antisense | SEQ ID NO: 67<br>SEQ ID NO: 68 |
| siEVI1-975 or siEVI1-B −4 | 5'-ucaagugcaaagacugugguu-3'<br>3'-uuaguucacguuucugacacc-5' | sense<br>antisense | SEQ ID NO: 69<br>SEQ ID NO: 70 |
| siEVI1-976 or siEVI1-B −3 | 5'-caagugcaaagacuguggauu-3'<br>3'-uuguucacguuucugacaccu-5' | sense<br>antisense | SEQ ID NO: 71<br>SEQ ID NO: 72 |
| siEVI1-977 or siEVI1-B −2 | 5'-aagugcaaagacuguggacuu-3'<br>3'-uuuucacguuucugacaccug-5' | sense<br>antisense | SEQ ID NO: 73<br>SEQ ID NO: 74 |
| siEVI1-978 or siEVI1-B −1 | 5'-agugcaaagacuguggacauu-3'<br>3'-uuucacguuucugacaccugu-5' | sense<br>antisense | SEQ ID NO: 75<br>SEQ ID NO: 76 |

TABLE 4-continued siRNA Duplexes Directed to EVI1 Target Sites B and C and Tiled from −10 to +10 Bases of the siEVI1-B and siEVI1-C siRNA Duplexes

| Description | Sequence | Strand | SEQ ID NO |
|---|---|---|---|
| siEVI1-980 or siEVI1-B +1 | 5'-ugcaaagacuguggacaaauu-3' | sense | SEQ ID NO: 77 |
| | 3'-uuacguuucugacaccuguuu-5' | antisense | SEQ ID NO: 78 |
| siEVI1-981 or siEVI1-B +2 | 5'-gcaaagacuguggacaaauuu-3' | sense | SEQ ID NO: 79 |
| | 3'-uucguuucugacaccuguuua-5' | antisense | SEQ ID NO: 80 |
| siEVI1-982 or siEVI1-B +3 or siEVI1-C -10 | 5'-caaagacuguggacaaauguu-3' | sense | SEQ ID NO: 81 |
| | 3'-uuguuucugacaccuguuuac-5' | antisense | SEQ ID NO: 82 |
| siEVI1-983 or siEVI1-B +4 or siEVI1-C -9 | 5'-aaagacuguggacaaauguuu-3' | sense | SEQ ID NO: 83 |
| | 3'-uuuuucugacaccuguuuaca-5' | antisense | SEQ ID NO: 84 |
| siEVI1-984 or siEVI1-B +5 or siEVI1-C -8 | 5'-aagacuguggacaaauguuu-3' | sense | SEQ ID NO: 85 |
| | 3'-uuuucugacaccuguuuacaa-5' | antisense | SEQ ID NO: 86 |
| siEVI1-985 or siEVI1-B +6 or siEVI1-C -7 | 5'-agacuguggacaaauguucuu-3' | sense | SEQ ID NO: 87 |
| | 3'-uuucugacaccuguuuacaag-5' | antisense | SEQ ID NO: 88 |
| siEVI1-986 or siEVI1-B +7 or siEVI1-C -6 | 5'-gacuguggacaaauguucauu-3' | sense | SEQ ID NO: 89 |
| | 3'-uucugacaccuguuuacaagu-5' | antisense | SEQ ID NO: 90 |
| siEVI1-987 or siEVI1-B +8 or siEVI1-C -5 | 5'-acuguggacaaauguucaguu-3' | sense | SEQ ID NO: 91 |
| | 3'-uuugacaccuguuuacaaguc-5' | antisense | SEQ ID NO: 92 |
| siEVI1-988 or siEVI1-B +9 or siEVI1-C -4 | 5'-cuguggacaaauguucagcuu-3' | sense | SEQ ID NO: 93 |
| | 3'-uugacaccuguuuacaagucg-5' | antisense | SEQ ID NO: 94 |
| siEVI1-989 or siEVI1-B +10 or siEVI1-C -3 | 5'-uguggacaaauguucagcauu-3' | sense | SEQ ID NO: 95 |
| | 3'-uuacaccuguuuacaagucgu-5' | antisense | SEQ ID NO: 96 |
| siEVI1-990 or siEVI1-C -2 | 5'-guggacaaauguucagcacuu-3' | sense | SEQ ID NO: 97 |
| | 3'-uucaccuguuuacaagucgug-5' | antisense | SEQ ID NO: 98 |
| siEVI1-991 or siEVI1-C -1 | 5'-uggacaaauguucagcacuu-3' | sense | SEQ ID NO: 99 |
| | 3'-uuaccuguuuacaagucguga-5' | antisense | SEQ ID NO: 100 |
| siEVI1-993 or siEVI1-C +1 | 5'-gacaaauguucagcacuacuu-3' | sense | SEQ ID NO: 101 |
| | 3'-uucuguuuacaagucgugaug-5' | antisense | SEQ ID NO: 102 |
| siEVI1-994 or siEVI1-C +2 | 5'-acaaauguucagcacuacguu-3' | sense | SEQ ID NO: 103 |
| | 3'-uuuguuuacaagucgugaugc-5' | antisense | SEQ ID NO: 104 |
| siEVI1-995 or siEVI1-C +3 | 5'-caaauguucagcacuacguuu-3' | sense | SEQ ID NO: 105 |
| | 3'-uuguuuacaagucgugaugca-5' | antisense | SEQ ID NO: 106 |
| siEVI1-996 or siEVI1-C +4 | 5'-aaauguucagcacuacgucuu-3' | sense | SEQ ID NO: 107 |
| | 3'-uuuuuacaagucgugaugcag-5' | antisense | SEQ ID NO: 108 |
| siEVI1-997 or siEVI1-C +5 | 5'-aauguucagcacuacgucuuu-3' | sense | SEQ ID NO: 109 |
| | 3'-uuuuacaagucgugaugcaga-5' | antisense | SEQ ID NO: 110 |
| siEVI1-998 or siEVI1-C +6 | 5'-auguucagcacuacgucuuuu-3' | sense | SEQ ID NO: 111 |
| | 3'-uuuacaagucgugaugcagaa-5' | antisense | SEQ ID NO: 112 |
| siEVI1-999 or siEVI1-C +7 | 5'-uguucagcacuacgucuucuu-3' | sense | SEQ ID NO: 113 |
| | 3'-uuacaagucgugaugcagaag-5' | antisense | SEQ ID NO: 114 |
| siEVI1-1000 or siEVI1-C +8 | 5'-guucagcacuacgucuuccuu-3' | sense | SEQ ID NO: 115 |
| | 3'-uucaagucgugaugcagaagg-5' | antisense | SEQ ID NO: 116 |
| siEVI1-1001 or siEVI1-C +9 | 5'-uucagcacuacgucuuccuuu-3' | sense | SEQ ID NO: 117 |
| | 3'-uuaagucgugaugcagaagga-5' | antisense | SEQ ID NO: IIS |
| siEVI1-1002 or siEVI1-C +10 | 5'-ucagcacuacgucuuccuuuu-3' | sense | SEQ ID NO: 119 |
| | 3'-uuagucgugaugcagaaggaa-5' | antisense | SEQ ID NO: 120 |

TABLE 5 siRNA Duplexes Directed to EVI1 Target Site D and Tiled from -10 to +10
Bases of the siEVI1-D siRNA Duplex

| Description | Sequence | Strand | SEQ ID NO |
|---|---|---|---|
| siEVI1-2900 or siEVI1-D -10 | 5'-caaucucccaggaaugugguu-3' | sense | SEQ ID NO: 121 |
| | 3'-uuguuagagggguccuuacacc-5' | antisense | SEQ ID NO: 122 |
| siEVI1-2901 or siEVI1-D -9 | 5'-aaucucccaggaauguggauu-3' | sense | SEQ ID NO: 123 |
| | 3'-uuuuagagggguccuuacaccu-5' | antisense | SEQ ID NO: 124 |
| siEVI1-2902 or siEVI1-D -8 | 5'-aucucccaggaaugugagguu-3' | sense | SEQ ID NO: 125 |
| | 3'-uuuagagggguccuuacaccuc-5' | antisense | SEQ ID NO: 126 |
| siEVI1-2903 or siEVI1-D -7 | 5'-ucucccaggaauguggagguu-3' | sense | SEQ ID NO: 127 |
| | 3'-uuagagggguccuuacaccucc-5' | antisense | SEQ ID NO: 128 |
| siEVI1-2904 or siEVI1-D -6 | 5'-cucccaggaauguggaggauu-3' | sense | SEQ ID NO: 129 |
| | 3'-uugagggguccuuacaccuccu-5' | antisense | SEQ ID NO: 130 |
| siEVI1-2905 or siEVI1-D -5 | 5'-ucccaggaauguggaggaguu-3' | sense | SEQ ID NO: 131 |
| | 3'-uuaggguccuuacaccuccuc-5' | antisense | SEQ ID NO: 132 |
| siEVI1-2906 or siEVI1-D -4 | 5'-cccaggaauguggaggagauu-3' | sense | SEQ ID NO: 133 |
| | 3'-uuggguccuuacaccuccucu-5' | antisense | SEQ ID NO: 134 |
| siEVI1-2907 or siEVI1-D -3 | 5'-ccaggaauguggaggagaguu-3' | sense | SEQ ID NO: 135 |
| | 3'-uugguccuuacaccuccucuc-5' | antisense | SEQ ID NO: 136 |
| siEVI1-2908 or siEVI1-D -2 | 5'-caggaauguggaggagagauu-3' | sense | SEQ ID NO: 137 |
| | 3'-uuguccuuacaccuccucucu-5' | antisense | SEQ ID NO: 138 |
| siEVI1-2909 or siEVI1-D -1 | 5'-aggaauguggaggagagaauu-3' | sense | SEQ ID NO: 139 |
| | 3'-uuuccuuacaccuccucucuu-5' | antisense | SEQ ID NO: 140 |
| siEVI1-2911 or siEVI1-D +1 | 5'-gaauguggaggagagaauguu-3' | sense | SEQ ID NO: 141 |
| | 3'-uucuuacaccuccucucuuac-5' | antisense | SEQ ID NO: 142 |
| siEVI1-2912 or siEVI1-D +2 | 5'-aauguggaggagagaaugauu-3' | sense | SEQ ID NO: 143 |
| | 3'-uuuuacaccuccucucuuacu-5' | antisense | SEQ ID NO: 144 |
| siEVI1-2913 or siEVI1-D +3 | 5'-auguggaggagagaaugaauu-3' | sense | SEQ ID NO: 145 |
| | 3'-uuuacaccuccucucuuacuu-5' | antisense | SEQ ID NO: 146 |
| siEVI1-2914 or siEVI1-D +4 | 5'-uguggaggagagaaugaauuu-3' | sense | SEQ ID NO: 147 |
| | 3'-uuacaccuccucucuuacuua-5' | antisense | SEQ ID NO: 148 |
| siEVI1-2915 or siEVI1-D +5 | 5'-guggaggagagaaugaauguu-3' | sense | SEQ ID NO: 149 |
| | 3'-uucaccuccucucuuacuuac-5' | antisense | SEQ ID NO: 150 |
| siEVI1-2916 or siEVI1-D +6 | 5'-uggaggagagaaugaaugguu-3' | sense | SEQ ID NO: 151 |
| | 3'-uuaccuccucucuuacuuacc-5' | antisense | SEQ ID NO: 152 |
| siEVI1-2917 or siEVI1-D +7 | 5'-ggaggagagaaugaauggcuu-3' | sense | SEQ ID NO: 153 |
| | 3'-uuccuccucucuuacuuaccg-5' | antisense | SEQ ID NO: 154 |
| siEVI1-2918 or siEVI1-D +8 | 5'-gaggagagaaugaauggcauu-3' | sense | SEQ ID NO: 155 |
| | 3'-uuccuccucucuuacuuaccgu-5' | antisense | SEQ ID NO: 156 |
| siEVI1-2919 or siEVI1-D +9 | 5'-aggagagaaugaauggcaguu-3' | sense | SEQ ID NO: 157 |
| | 3'-uuuccucucuuacuuaccguc-5' | antisense | SEQ ID NO: 158 |
| siEVI1-2920 or siEVI1-D +10 | 5'-ggagagaaugaauggcaguuu-3' | sense | SEQ ID NO: 159 |
| | 3'-uuccucucuuacuuaccguca-5' | antisense | SEQ ID NO: 160 |

TABLE 6 siRNA Duplexes Directed to EVI1 Target Site E and Tiled from -10 to +10 Bases of the
siEVI1-E siRNA Duplex

| Description | Sequence | Strand | SEQ ID NO |
|---|---|---|---|
| siEVI1-2984 or siEVI1-E -10 | 5'-uugcuggaugaugaagaaguu-3' | sense | SEQ ID NO: 161 |
| | 3'-uuaacgaccuacuacuucuuc-5' | antisense | SEQ ID NO: 162 |
| siEVI1-2985 or siEVI1-E -9 | 5'-ugcuggaugaugaagaaguuu-3' | sense | SEQ ID NO: 163 |
| | 3'-uuacgaccuacuacuucuuca-5' | antisense | SEQ ID NO: 164 |

TABLE 6-continued siRNA Duplexes Directed to EVI1 Target Site E and Tiled from -10 to +10 Bases of the siEVI1-E siRNA Duplex

| Description | Sequence | Strand | SEQ ID NO |
|---|---|---|---|
| siEVI1-2986 or siEVI1-E -8 | 5'-gcuggaugaugaagaaguuuu-3' | sense | SEQ ID NO: 165 |
|  | 3'-uucgaccuacuacuucuucaa-5' | antisense | SEQ ID NO: 166 |
| siEVI1-2987 or siEVI1-E -7 | 5'-cuggaugaugaagaaguuguu-3' | sense | SEQ ID NO: 167 |
|  | 3'-uugaccuacuacuucuucaac-5' | antisense | SEQ ID NO: 168 |
| siEVI1-2988 or siEVI1-E -6 | 5'-uggaugaugaagaaguugauu-3' | sense | SEQ ID NO: 169 |
|  | 3'-uuaccuacuacuucuucaacu-5' | antisense | SEQ ID NO: 170 |
| siEVI1-2989 or siEVI1-E -5 | 5'-ggaugaugaagaaguugaauu-3' | sense | SEQ ID NO: 171 |
|  | 3'-uuccuacuacuucuucaacuu-5' | antisense | SEQ ID NO: 172 |
| siEVI1-2990 or siEVI1-E -4 | 5'-gaugaugaagaaguugaaguu-3' | sense | SEQ ID NO: 173 |
|  | 3'-uucuacuacuucuucaacuuc-5' | antisense | SEQ ID NO: 174 |
| siEVI1-2991 or siEVI1-E -3 | 5'-augaugaagaaguugaagauu-3' | sense | SLO ID NO: 175 |
|  | 3'-uuuacuacuucuucaacuucu-5' | antisense | SEQ ID NO: 176 |
| siEVI1-2992 or siEVI1-E -2 | 5'-ugaugaagaaguugaagauu-3' | sense | SEQ ID NO: 177 |
|  | 3'-uuacuacuucuucaacuucua-5' | antisense | SEQ ID NO: 178 |
| siEVI1-2993 or siEVI1-E -1 | 5'-gaugaagaaguugaagauguu-3' | sense | SEQ ID NO: 179 |
|  | 3'-uucuacuucuucaacuucuac-5' | antisense | SEQ ID NO: 180 |
| siEVI1-2995 or siEVI1-E +1 | 5'-ugaagaaguugaagaugaguu-3' | sense | SEQ ID NO: 181 |
|  | 3'-uuacuucuucaacuucuacuc-5' | antisense | SEQ ID NO: 182 |
| siEVI1-2996 or siEVI1-E +2 | 5'-gaagaaguugaagaugagguu-3' | sense | SEQ ID NO: 183 |
|  | 3'-uucuucuucaacuucuacucc-5' | antisense | SEQ ID NO: 184 |
| siEVI1-2997 or siEVI1-E +3 | 5'-aagaaguugaagaugagguuu-3' | sense | SEQ ID NO: 185 |
|  | 3'-uuuucuucaacuucuacucca-5' | antisense | SEQ ID NO: 186 |
| siEVI1-2998 or siEVI1-E +4 | 5'-agaaguugaagaugagguguu-3' | sense | SEQ ID NO: 187 |
|  | 3'-uuucuucaacuucuacuccac-5' | antisense | SEQ ID NO: 188 |
| siEVI1-2999 or siEVI1-E +5 | 5'-gaaguugaagaugaggguguuu-3' | sense | SEQ ID NO: 189 |
|  | 3'-uucuucaacuucuacuccaca-5' | antisense | SEQ ID NO: 190 |
| siEVI1-3000 or siEVI1-E +6 | 5'-aaguugaagaugaggguguuuu-3' | sense | SEQ ID NO: 191 |
|  | 3'-uuuucaacuucuacuccacaa-5' | antisense | SEQ ID NO: 192 |
| siEVI1-3001 or siEVI1-E +7 | 5'-aguugaagaugagguguuguu-3' | sense | SEQ ID NO: 193 |
|  | 3'-uuucaacuucuacuccacaac-5' | antisense | SEQ ID NO: 194 |
| siEVI1-3002 or siEVI1-E +8 | 5'-guugaagaugagguguuguuu-3' | sense | SEQ ID NO: 195 |
|  | 3'-uucaacuucuacuccacaaca-5' | antisense | SEQ ID NO: 196 |
| siEVI1-3003 or siEVI1-E +9 | 5'-uugaagaugagguguuguuuu-3' | sense | SEQ ID NO: 197 |
|  | 3'-uuaacuucuacuccacaacaa-5' | antisense | SEQ ID NO: 198 |
| siEVI1-3004 or siEVI1-E +10 | 5'-ugaagaugagguguuguuauu-3' | sense | SEQ ID NO: 199 |
|  | 3'-uuacuucuacuccacaacaau-5' | antisense | SEQ ID NO: 200 |

TABLE 7

Properties of Ovarian Cell Lines

| Cell line | Disease | Morphology | Age/Ethnicity | Cytogenetics |
|---|---|---|---|---|
| OVCAR3 | Adenocarcinoma | Epithelial | 60/Caucasian | Chromosome counts near triploid |
| SK-OV-3 | Adenocarcinoma | Epithelial | 64/Caucasian | Chromosome number ranges 42-45 |
| OV-90 | Adenocarcinoma | Epithelial | 64/French-Canadian | 46, XX, der(1)t(1; 10)(p36; p15), hsr(3)(p11), der(9; 17)(q10; q10), der(10)t(10; 17)(p15; p12p13), der(13)t(13; 13)(p11; q14) |

TABLE 7-continued

Properties of Ovarian Cell Lines

| Cell line | Disease | Morphology | Age/Ethnicity | Cytogenetics |
|---|---|---|---|---|
| TOV-112D | Endometrioid carcinoma | Epithelial | 42/French-Canadian | 52, XX, add(X)(p22), +add(1)(p22), +add(1)(p22), +2, +9, +12, add(15)(p11), +17 |
| Hs832.Tc | Endometriosis | Fibroblast | ?/Caucasian | |
| PA-1 | Teratocarcinoma | Epithelial | 12/Caucasian | |
| ES-2 | Clear Cell Carcinoma | Fibroblast | 47/Black | Hyperdiploid karyotype of 66XX to 88XX |
| UWB1.289 | Carcinoma | Epithelial | 56/ | |
| Caov-3 | Adenocarcinoma | Epithelial | 54/Caucasian | |

TABLE 8

Summary of Ovarian Cell Lines with siRNA Treatment

Response to siRNA (% growth inhibition)

| Cell line | siEVI1-256 | siEVI1-979 | siEVI1-992 | siEVI1-2910 | siEVI1-2994 |
|---|---|---|---|---|---|
| OVCAR3 | 0 | 60 | 0 | 73 | 0 |
| SK-OV-3 | 12 | 42 | 31 | 12 | 0 |
| OV-90 | 26 | 16 | 25 | 23 | 33 |
| TOV-112D | 36 | 79 | 70 | 85 | 70 |
| Hs832.Tc | 0 | 0 | 10 | 0 | 0 |
| PA-1 | 0 | 0 | 0 | 0 | 18 |
| ES-2 | 0 | 63 | 54 | 92 | 54 |
| UWB1.289 | 43 | 14 | 73 | 67 | 0 |
| Caov-3 | 13 | 34 | 46 | 47 | 28 |

TABLE 9

Properties of Prostate Cell Lines

| Cell line | Disease | Morphology | Age/Ethnicity | Cytogenetics |
|---|---|---|---|---|
| LNCaP | Carcinoma | Epithelial | 50/Caucsian | Hypotetraploid 84 chromosomes |
| PC3 | Adeno-carcinoma | Epithelial | 62/Caucasian | Near-triploid 62 chromosomes |
| WPMY-1 | Normal | Epithelial | 54/Caucasian | Normal diploid |

TABLE 10

Summary of Prostate Cell Lines with siRNA Treatment

Response to siRNA (% growth inhibition)

| Cell line | siEVI1-256 | siEVI1-979 | siEVI1-992 | siEVI1-2910 | siEVI1-2994 |
|---|---|---|---|---|---|
| LNCaP | 4 | 12 | 12 | 46 | 12 |
| PC3 | 23 | 8 | 35 | 53 | 25 |
| WPMY-1 | N/A | N/A | N/A | N/A | N/A |

TABLE 11

Properties of Breast Cell Lines

| Cell line | Disease | Morphology | Age/Ethnicity | Cytogenetics |
|---|---|---|---|---|
| MCF-7 | Adeno-carcinoma | Epithelial | 69/Caucasian | Hypertriploidy to hypotetraploidy |
| MDA-MB-231 | Adeno-carcinoma | Epithelial | 51/Caucasiain | Aneuploid near tripoid |

TABLE 11-continued

Properties of Breast Cell Lines

| Cell line | Disease | Morphology | Age/Ethnicity | Cytogenetics |
|---|---|---|---|---|
| BT-483 | Ductal carcinoma | Epithelial | 23/Caucasian | Polyploid, 72 chromosomes |
| MCF10A | Fibroid cyst | Epithelial | 36/Caucasian | Normal Diploid |

TABLE 12

Summary of Breast Cell Lines with siRNA Treatment

Response to siRNA (% growth inhibition)

| Cell line | siEVI1-256 | siEVI1-979 | siEVI1-992 | siEVI1-2910 | siEVI1-2994 |
|---|---|---|---|---|---|
| MCF-7 | 32 | 0 | 0 | 67 | 57 |
| MDA-MB-231 | 31 | 14 | 23 | 21 | 21 |
| BT-483 | N/A | N/A | N/A | N/A | N/A |
| MCF10A | N/A | N/A | N/A | N/A | N/A |

TABLE 13

Properties of Lung Cell Lines

| Cell line | Disease | Morphology | Age/Ethnicity | Cytogenetics |
|---|---|---|---|---|
| HBE135-E6E7 | Normal bronchial epithelium | Epithelial | 54/Asian | |
| H2170 | Squamous cell carcinoma | Epithelial | nonsmoker | |
| H226 | Squamous cell carcinoma | Epithelial | | |
| SW900 | Squamous cell carcinoma | Epithelial | | |

TABLE 14

Properties of Colon Cell Lines

| Cell line | Disease | Morphology | Age/Ethnicity | Cytogenetics |
|---|---|---|---|---|
| HT-29 | Adenocarcinoma | Epithelial | 44/Caucasian | |
| HCT116 | Carcinoma | Epithelial | Asian | |
| CaCO-2 | Adenocarcinoma | Epithelial | 72/Caucasian | |
| FHC | normal | Epithelial | 13 weeks | |

TABLE 15

Properties of Melanoma Cell Lines

| Cell line | Disease | Morphology | Age/Ethnicity | Cytogenetics |
|---|---|---|---|---|
| WM-115 | Primary melanoma | Epithelial | 58/Caucasian | Chromosome counts near triploid |
| WM-266-4 | Malignant melanoma | Epithelial | 58/Caucasian | Chromosome number ranges 42-45 |
| M4A4 | Malignant melanoma | Epithelial | 31/Caucasian | 46, XX, der(1)t(1; 10)(p36; p15), hsr(3)(p11), der(9; 17)(q10; q10), der(10)t(10; 17)(p15; p12p13), der(13)t(13; 13)(p11; q14) |
| NM2C5 | Nonmalignant melanoma | Epithelial | 31/Caucasian | 52, XX, add(X)(p22), +add(1)(p22), +add(1)(p22), +2, +9, +12, add(15)(p11), +17 |

TABLE 16

Properties of Leukemia Cell Lines

| Cell line | Disease | Morphology | Age/Ethnicity | Cytogenetics |
|---|---|---|---|---|
| HEL 92.1.7 | Erythroleukemia | Lymphoblast | 30/Caucasian | |
| HL60 | Aciye myelocytic leukemia | Myeloblast | 36/Caucasian | Pseudodiplid |

It should be understood that the foregoing disclosure emphasizes certain specific embodiments of the invention and that all modifications or alternatives equivalent thereto are within the spirit and scope of the invention as set forth in the appended claims.

We claim:

1. A pharmaceutical composition for specifically reducing expression of the human Ecotropic Virus Integration site 1 (EVI1) gene in a tumor cell, the pharmaceutical composition comprising:

an isolated polynucleotide comprising a sequence that is a contiguous portion of nucleotide sequence of SEQ ID NO: 1, wherein said contiguous portion of the nucleotide sequence of SEQ ID NO: 1 is from nucleotide 2900 through 2930, and comprises a length of 19 to 30 nucleotides, the pharmaceutical composition further comprising a chemotherapeutic drug or agent; and a pharmaceutically acceptable carrier, excipient or adjuvant.

2. The pharmaceutical composition of claim 1, wherein the isolated polynucleotide is an oligoribonucleotide comprising a RNA sequence that hybridizes to mRNA transcribed from said contiguous portion of the nucleotide sequence of SEQ ID NO: 1.

3. The pharmaceutical composition of claim 1, wherein the isolated polynucleotide is double-stranded, and wherein the isolated polynucleotide comprises a combination of SEQ ID NOS: 13 and 14.

4. A method for inhibiting Ecotropic Virus Integration site 1 (EVI1) in a tumor cell, comprising the step of contacting a tumor cell with an effective amount of the pharmaceutical composition of claim 1.

5. The method of claim 4 wherein the tumor cell is from:
a tumor of lung, breast, prostate, or ovarian tissue or organ; or
a melanoma; or
acute myelocytic leukemia.

6. The pharmaceutical composition of claim 1, further comprising a liposome.

7. The pharmaceutical composition of claim 6, wherein the liposome is PEGylated.

8. The pharmaceutical composition of claim 6, wherein the liposome comprises a cell-targeting moiety.

9. The pharmaceutical composition of claim 8, wherein the cell-targeting moiety is a protein, a peptide or an aptamer.

10. The pharmaceutical composition of claim 1, further comprising a nanoparticle.

11. The pharmaceutical composition of claim 10, wherein the nanoparticle comprises lipids, cyclodextrin, chitosan, carbohydrate polymers, elastin-like polymers (ELP), calcium phosphate polymers or combinations thereof.

12. The pharmaceutical composition of claim 10, wherein the nanoparticle is PEGylated.

13. The pharmaceutical composition of claim 10, wherein the nanoparticle comprises a cell-targeting moiety.

14. The pharmaceutical composition of claim 13, wherein the cell-targeting moiety is a protein, a peptide or an aptamer.

15. The pharmaceutical composition of claim 6, wherein the pharmaceutical composition is encapsulated in the liposome.

16. The pharmaceutical composition of claim 10, wherein the pharmaceutical composition is encapsulated in the liposome.

* * * * *

```
                    SEQUENCE LISTING

<160> NUMBER OF SEQ ID NOS: 206

<210> SEQ ID NO 1
<211> LENGTH: 4891
<212> TYPE: DNA
<213> ORGANISM: Homo sapiens

<400> SEQUENCE: 1
agccttcttt cctcctcgcc cgcagtctcg cggagccctg ctgcttatct acgttgctaa      60
gccgggcgat ttccttgttc ctcctgcgaa acggtgcggt ctggacacgt ctccggggtg     120
ggtcgtccgg ccttcgatct tagacgaatt ttacaatgtg aagttctgca tagatgccag     180
tcaaccagat gttggaagct ggctcaagta cattagattc gctggctgtt atgatcagca     240
caaccttgtt gcatgccaga taaatgatca gatattctat agagtagttg cagacattgc     300
gccgggagag gagcttctgc tgttcatgaa gagcgaagac tatccccatg aaactatggc     360
gccggatatc cacgaagaac ggcaatatcg ctgcgaagac tgtgaccagc tctttgaatc     420
taaggctgaa ctagcagatc accaaaagtt tccatgcagt actcctcact cagcattttc     480
aatggttgaa gaggactttc agcaaaaact cgaaagcgag aatgatctcc aagagataca     540
cacgatccag gagtgtaagg aatgtgacca agttttcct gatttgcaaa gcctggagaa      600
acacatgctg tcacatactg aagagaggga atacaagtgt gatcagtgtc caaggcatt     660 taactggaag tccaatttaa ttcgccacca gatgtcacat gacagtggaa agcactatga      720
atgtgaaaac tgtgccaagg ttttcacgga ccctagcaac cttcagcggc acattcgctc      780
tcagcatgtc ggtgcccggg cccatgcatg cccggagtgt ggcaaaacgt tgccacttc     840 gtcgggcctc aaacaacaca agcacatcca cagcagtgtg aagcccttta tctgtgaggt      900
ctgccataaa tcctatactc agttttcaaa cctttgccgt cataagcgca tgcatgctga      960
ttgcagaacc caaatcaagt gcaaagactg tggacaaatg ttcagcacta cgtcttcctt     1020
```

```
aaataaacac aggaggtttt gtgagggcaa gaaccattt  gcggcaggtg gattttttgg    1080
ccaaggcatt tcacttcctg gaaccccagc tatggataaa acgtccatgg ttaatatgag    1140
tcatgccaac ccgggccttg ctgactattt tggcgccaat aggcatcctg ctggtcttac    1200
ctttccaaca gctcctggat tttcttttag cttccctggt ctgtttcctt ccggcttgta    1260
ccacaggcct cctttgatac ctgctagttc cctgttaaa  ggactatcaa gtactgaaca    1320
gacaaacaaa agtcaaagtc ccctcatgac acatcctcag atactgccag ctacacagga    1380
tattttgaag gcactatcta aacacccatc tgtagggggac aataagccag tggagctcca   1440
gcccgagagg tcctctgaag agaggcccct tgagaaaatc agtgaccagt cagagagtag    1500
tgaccttgat gatgtcagta caccaagtgg cagtgacctg aaacaacct  cgggctctga    1560 tctggaaagt gacattgaaa gtgataaaga gaaatttaaa gaaatggta  aaatgttcaa    1620 agacaaagta agccctcttc agaatctggc ttcaataaat aataagaaag aatacagcaa    1680
tcattccatt ttctcaccat ctttagagga gcagactgcg gtgtcaggag ctgtgaatga    1740
ttctataaag gctattgctt ctattgctga aaaatacttt ggttcaacag gactggtggg    1800
gctgcaagac aaaaaagttg gagctttacc ttacccttcc atgtttcccc tcccattttt    1860
tccagcattc tctcaatcaa tgtacccatt tcctgataga gacttgagat cgttaccttt    1920
gaaaatggaa ccccaatcac caggtgaagt aaagaaactg cagaagggca gctctgagtc    1980
cccctttgat ctcaccacta agcgaaagga tgagaagccc ttgactccag tcccctccaa    2040
gcctccagtg acacctgcca caagccaaga ccagcccctg gatctaagta tgggcagtag    2100
gagtagagcc agtgggacaa agctgactga gcctcgaaaa aaccacgtgt ttgggggaaa    2160
aaaaggaagc aacgtcgaat caagacctgc ttcagatggt tccttgcagc atgcaagacc    2220
cactcctttc tttatggacc ctatttacag agtagagaaa agaaaactaa ctgacccact    2280
tgaagcttta aaagagaaat acttgaggcc ttctccagga ttcttgtttc acccacaatt    2340
ccaactgcct gatcagagaa cttggatgtc agctattgaa aacatggcag aaaagctaga    2400
gagcttcagt gccctgaaac ctgaggccag tgagctctta cagtcagtgc cctctatgtt    2460
caacttcagg gcgcctccca atgccctgcc agagaacctt ctgcggaagg gaaaggagcg    2520
ctatacctgc agatactgtg gcaagatttt tccaaggtct gcaaacctaa cacggcactt    2580
gagaacccac acaggagagc agccttacag atgcaaatac tgtgacagat catttagcat    2640
atcttctaac ttgcaaaggc atgttcgcaa catccacaat aaagagaagc catttaagtg    2700
tcacttatgt gataggtgtt ttggtcaaca aaccaattta gacagacacc taaagaaaca    2760
tgagaatggg aacatgtccg gtacagcaac atcgtcgcct cattctgaac tggaaagtac    2820
aggtgcgatt ctggatgaca aagaagatgc ttacttcaca gaaattcgaa atttcattgg    2880
gaacagcaac catggcagcc aatctcccag gaatgtggag gagagaatga atggcagtca    2940
ttttaaagat gaaaaggctt tggtgaccag tcaaaattca gacttgctgg atgatgaaga    3000
agttgaagat gaggtgttgt tagatgagga ggatgaagac aatgatatta ctggaaaaac    3060
aggaaaggaa ccagtgacaa gtaatttaca tgaaggaaac cctgaggatg actatgaaga    3120
aaccagtgcc ctggagatga gttgcaagac atccccagtg aggtataaag aggaagaata    3180
taaaagtgga cttctgctc  tagatcatat aaggcacttc acagatagcc tcaaaatgag    3240
gaaaatggaa gataatcaat attctgaagc tgagctgtct tcttttagta cttcccatgt    3300
gccagaggaa cttaagcagc cgttacacag aaagtccaaa tcgcaggcat atgctatgat    3360
```

```
gctgtcactg tctgacaagg agtccctcca ttctacatcc cacagttctt ccaacgtgtg    3420
gcacagtatg gccagggctg cggcggaatc cagtgctatc cagtccataa gccacgtatg    3480
acgttatcaa ggttgaccag agtgggacca agtccaacag tagcatggct ctttcatata    3540
ggactattta caagactgct gagcagaatg ccttataaac ctgcagggtc actcatctaa    3600
agtctagtga ccttaaactg aatgatttaa aaagaaaag aaagaaaaaa gaaactattt    3660
attctcgata ttttgttttg cacagcaaag gcagctgctg acttctggaa gatcaatcaa    3720
tgcgacttaa agtgattcag tgaaaacaaa aaacttggtg ggctgaaggc atcttccagt    3780
ttaccccacc ttagggtatg ggtgggtgag aagggcagtt gagatggcag cattgatatg    3840
aatgaacact ccatagaaac tgaattctct tttgtacaag atcacctgac atgattggga    3900
acagttgctt ttaattacag atttaatttt tttcttcgtt aaagttttat gtaatttaac    3960
cctttgaaga cagaagtagt tggatgaaat gcacagtcaa ttattataga aactgataac    4020
agggagtact tgttccccct tttgccttct taagtacatt gtttaaaact agggaaaaag    4080
ggtatgtgta tattgtaaac tatggatgtt aacactcaaa gaggttaagt cagtgaagta    4140
acctattcat caccagtacc gctgtaccac taataaattg tttgccaaat ccttgtaata    4200
acatcttaat tttagacaat catgtcactg ttttaatgt ttattttttt gtgtgtgttg    4260
cgtgtatcat gtatttattt gttggcaaac tattgtttgt tgattaaaat agcactgttc    4320
cagtcagcca ctactttatg acgtctgagg cacacccctt tccgaatttc aaggaccaag    4380
gtgacccgac ctgtgtatga gagtgccaaa tggtgtttgg cttttcttaa cattccttt    4440 tgtttgtttg ttttgttttc cttcttaatg aactaaatac gaatagatgc aacttagttt    4500
ttgtaatact gaaatcgatt caattgtata aacgattata atttctttca tggaagcatg    4560
attcttctga ttaaaaactg tactccatat tttatgctgg ttgtctgcaa gcttgtgcga    4620
tgttatgttc atgttaatcc tatttgtaaa atgaagtgtt cccaacctta tgttaaaaga    4680
gagaagtaaa taacagactg tattcagtta ttttgccctt tattgaggaa ccagatttgt    4740 tttcttttg tttgtaatct cattttgaaa taatcagcaa gttgaggtac tttcttcaaa    4800
tgctttgtac aatataaact gttatgcctt tcagtgcatt actatgggag gagcaactaa    4860
aaaataaaga cttacaaaaa ggagtatttt t                                   4891
```

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
ccagauaaau gaucagaua                                                   19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
gugcaaagac uguggacaa                                                   19

<210> SEQ ID NO 4
<211> LENGTH: 19

```
<212> TYPE: RNA
<213> ORGANISM: Artificial Sequence
<220> FEATURE:
<223> OTHER INFORMATION: Synthetic

<400> SEQUENCE: 4
ggacaaaugu ucagcacua                                                    19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5 ggaugugga ggagagaau                                                     19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
augaagaagu ugaagauga                                                    19

<210> SEQ ID NO 7
<211> LENGTH: 21
<212> TYPE: RNA
<213> ORGANISM: Artificial Sequence
<220> FEATURE:
<223> OTHER INFORMATION: Synthetic

<400> SEQUENCE: 7
ccagauaaau gaucagauau u                                                 21

<210> SEQ ID NO 8
<211> LENGTH: 21
<212> TYPE: RNA
<213> ORGANISM: Artificial Sequence
<220> FEATURE:
<223> OTHER INFORMATION: Synthetic

<400> SEQUENCE: 8
uaucugauca uuuaucuggu u                                                 21

<210> SEQ ID NO 9
<211> LENGTH: 21
<212> TYPE: RNA
<213> ORGANISM: Artificial Sequence
<220> FEATURE:
<223> OTHER INFORMATION: Synthetic

<400> SEQUENCE: 9
gugcaaagac uguggacaau u                                                 21

<210> SEQ ID NO 10
<211> LENGTH: 21
<212> TYPE: RNA
<213> ORGANISM: Artificial Sequence
<220> FEATURE:
<223> OTHER INFORMATION: Synthetic

<400> SEQUENCE: 10
``` uguccacag ucuuugcacu u                                              21

<210> SEQ ID NO 11
<211> LENGTH: 21
<212> TYPE: RNA
<213> ORGANISM: Artificial Sequence
<220> FEATURE:
<223> OTHER INFORMATION: Synthetic

<400> SEQUENCE: 11
ggacaaaugu ucagcacuau u                                             21

<210> SEQ ID NO 12
<211> LENGTH: 21
<212> TYPE: RNA
<213> ORGANISM: Artificial Sequence
<220> FEATURE:
<223> OTHER INFORMATION: Synthetic

<400> SEQUENCE: 12
uagugcugaa cauuuguccu u                                             21

<210> SEQ ID NO 13
<211> LENGTH: 21
<212> TYPE: RNA
<213> ORGANISM: Artificial Sequence
<220> FEATURE:
<223> OTHER INFORMATION: Synthetic

<400> SEQUENCE: 13
ggaaugugga ggagagaauu u                                             21

<210> SEQ ID NO 14
<211> LENGTH: 21
<212> TYPE: RNA
<213> ORGANISM: Artificial Sequence
<220> FEATURE:
<223> OTHER INFORMATION: Synthetic

<400> SEQUENCE: 14
auucucuccu ccacauuccu u                                             21

<210> SEQ ID NO 15
<211> LENGTH: 21
<212> TYPE: RNA
<213> ORGANISM: Artificial Sequence
<220> FEATURE:
<223> OTHER INFORMATION: Synthetic

<400> SEQUENCE: 15
augaagaagu ugaagaugau u                                             21

<210> SEQ ID NO 16
<211> LENGTH: 21
<212> TYPE: RNA
<213> ORGANISM: Artificial Sequence
<220> FEATURE:
<223> OTHER INFORMATION: Synthetic

<400> SEQUENCE: 16
ucaucuucaa cuucuucauu u                                             21

<210> SEQ ID NO 17
<211> LENGTH: 21
<212> TYPE: RNA
<213> ORGANISM: Artificial Sequence

```
<220> FEATURE:
<223> OTHER INFORMATION: Synthetic

<400> SEQUENCE: 17
uuguugcaug ccagauaaau u                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetic

<400> SEQUENCE: 18
uuuaucuggc augcaacaau u                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetic

<400> SEQUENCE: 19
uguugcaugc cagauaaauu u                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic

<400> SEQUENCE: 20
auuuaucugg caugcaacau u                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic

<400> SEQUENCE: 21
guugcaugcc agauaaaugu u                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic

<400> SEQUENCE: 22
cauuuaucug gcaugcaacu u                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic

<400> SEQUENCE: 23
uugcaugcca gauaaaugau u                                              21
```

<210> SEQ ID NO 24
<211> LENGTH: 21
<212> TYPE: RNA
<213> ORGANISM: Artificial Sequence
<220> FEATURE:
<223> OTHER INFORMATION: Synthetic

<400> SEQUENCE: 24
ucauuuaucu ggcaugcaau u                                              21

<210> SEQ ID NO 25
<211> LENGTH: 21
<212> TYPE: RNA
<213> ORGANISM: Artificial Sequence
<220> FEATURE:
<223> OTHER INFORMATION: Synthetic

<400> SEQUENCE: 25
ugcaugccag auaaaugauu u                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic

<400> SEQUENCE: 26
aucauuuauc uggcaugcau u                                              21

<210> SEQ ID NO 27
<211> LENGTH: 21
<212> TYPE: RNA
<213> ORGANISM: Artificial Sequence
<220> FEATURE:
<223> OTHER INFORMATION: Synthetic

<400> SEQUENCE: 27
gcaugccaga uaaaugaucu u                                              21

<210> SEQ ID NO 28
<211> LENGTH: 21
<212> TYPE: RNA
<213> ORGANISM: Artificial Sequence
<220> FEATURE:
<223> OTHER INFORMATION: Synthetic

<400> SEQUENCE: 28
gaucauuuau cuggcaugcu u                                              21

<210> SEQ ID NO 29
<211> LENGTH: 21
<212> TYPE: RNA
<213> ORGANISM: Artificial Sequence
<220> FEATURE:
<223> OTHER INFORMATION: Synthetic

<400> SEQUENCE: 29
caugccagau aaaugaucau u                                              21

<210> SEQ ID NO 30
<211> LENGTH: 21
<212> TYPE: RNA
<213> ORGANISM: Artificial Sequence
<220> FEATURE:
<223> OTHER INFORMATION: Synthetic

<400> SEQUENCE: 30
ugaucauuua ucuggcaugu u                                              21

<210> SEQ ID NO 31
<211> LENGTH: 21
<212> TYPE: RNA
<213> ORGANISM: Artificial Sequence
<220> FEATURE:
<223> OTHER INFORMATION: Synthetic

<400> SEQUENCE: 31
augccagaua aaugaucagu u                                              21

<210> SEQ ID NO 32
<211> LENGTH: 21
<212> TYPE: RNA
<213> ORGANISM: Artificial Sequence
<220> FEATURE:
<223> OTHER INFORMATION: Synthetic

<400> SEQUENCE: 32
cugaucauuu aucuggcauu u                                              21

<210> SEQ ID NO 33
<211> LENGTH: 21
<212> TYPE: RNA
<213> ORGANISM: Artificial Sequence
<220> FEATURE:
<223> OTHER INFORMATION: Synthetic

<400> SEQUENCE: 33
ugccagauaa augaucagau u                                              21

<210> SEQ ID NO 34
<211> LENGTH: 21
<212> TYPE: RNA
<213> ORGANISM: Artificial Sequence
<220> FEATURE:
<223> OTHER INFORMATION: Synthetic

<400> SEQUENCE: 34
ucugaucauu uaucuggcau u                                              21

<210> SEQ ID NO 35
<211> LENGTH: 21
<212> TYPE: RNA
<213> ORGANISM: Artificial Sequence
<220> FEATURE:
<223> OTHER INFORMATION: Synthetic

<400> SEQUENCE: 35
gccagauaaa ugaucagauu u                                              21

<210> SEQ ID NO 36
<211> LENGTH: 21
<212> TYPE: RNA
<213> ORGANISM: Artificial Sequence
<220> FEATURE:
<223> OTHER INFORMATION: Synthetic

<400> SEQUENCE: 36
aucugaucau uuaucuggcu u                                              21

<210> SEQ ID NO 37

```
<211> LENGTH: 21
<212> TYPE: RNA
<213> ORGANISM: Artificial Sequence
<220> FEATURE:
<223> OTHER INFORMATION: Synthetic

<400> SEQUENCE: 37
cagauaaaug aucagauauu u                                              21

<210> SEQ ID NO 38
<211> LENGTH: 21
<212> TYPE: RNA
<213> ORGANISM: Artificial Sequence
<220> FEATURE:
<223> OTHER INFORMATION: Synthetic

<400> SEQUENCE: 38
auaucugauc auuuaucugu u                                              21

<210> SEQ ID NO 39
<211> LENGTH: 21
<212> TYPE: RNA
<213> ORGANISM: Artificial Sequence
<220> FEATURE:
<223> OTHER INFORMATION: Synthetic

<400> SEQUENCE: 39
agauaaauga ucagauauuu u                                              21

<210> SEQ ID NO 40
<211> LENGTH: 21
<212> TYPE: RNA
<213> ORGANISM: Artificial Sequence
<220> FEATURE:
<223> OTHER INFORMATION: Synthetic

<400> SEQUENCE: 40
aauaucugau cauuuaucuu u                                              21

<210> SEQ ID NO 41
<211> LENGTH: 21
<212> TYPE: RNA
<213> ORGANISM: Artificial Sequence
<220> FEATURE:
<223> OTHER INFORMATION: Synthetic

<400> SEQUENCE: 41
gauaaaugau cagauauucu u                                              21

<210> SEQ ID NO 42
<211> LENGTH: 21
<212> TYPE: RNA
<213> ORGANISM: Artificial Sequence
<220> FEATURE:
<223> OTHER INFORMATION: Synthetic

<400> SEQUENCE: 42
gaauaucuga ucauuuaucu u                                              21

<210> SEQ ID NO 43
<211> LENGTH: 21
<212> TYPE: RNA
<213> ORGANISM: Artificial Sequence
<220> FEATURE:
<223> OTHER INFORMATION: Synthetic

<400> SEQUENCE: 43
```
auaaaugauc agauauucuu u                                        21

<210> SEQ ID NO 44
<211> LENGTH: 21
<212> TYPE: RNA
<213> ORGANISM: Artificial Sequence
<220> FEATURE:
<223> OTHER INFORMATION: Synthetic

<400> SEQUENCE: 44
agaauaucug aucauuuauu u                                        21

<210> SEQ ID NO 45
<211> LENGTH: 21
<212> TYPE: RNA
<213> ORGANISM: Artificial Sequence
<220> FEATURE:
<223> OTHER INFORMATION: Synthetic

<400> SEQUENCE: 45
uaaaugauca gauauucuau u                                        21

<210> SEQ ID NO 46
<211> LENGTH: 21
<212> TYPE: RNA
<213> ORGANISM: Artificial Sequence
<220> FEATURE:
<223> OTHER INFORMATION: Synthetic

<400> SEQUENCE: 46
uagaauaucu gaucauuuau u                                        21

<210> SEQ ID NO 47
<211> LENGTH: 21
<212> TYPE: RNA
<213> ORGANISM: Artificial Sequence
<220> FEATURE:
<223> OTHER INFORMATION: Synthetic

<400> SEQUENCE: 47
aaaugaucag auauucuauu u                                        21

<210> SEQ ID NO 48
<211> LENGTH: 21
<212> TYPE: RNA
<213> ORGANISM: Artificial Sequence
<220> FEATURE:
<223> OTHER INFORMATION: Synthetic

<400> SEQUENCE: 48
auagaauauc ugaucauuuu u                                        21

<210> SEQ ID NO 49
<211> LENGTH: 21
<212> TYPE: RNA
<213> ORGANISM: Artificial Sequence
<220> FEATURE:
<223> OTHER INFORMATION: Synthetic

<400> SEQUENCE: 49
aaugaucaga uauucuauau u                                        21

<210> SEQ ID NO 50
<211> LENGTH: 21
<212> TYPE: RNA

```
<213> ORGANISM: Artificial Sequence
<220> FEATURE:
<223> OTHER INFORMATION: Synthetic

<400> SEQUENCE: 50
uauagaauau cugaucauuu u                                              21

<210> SEQ ID NO 51
<211> LENGTH: 21
<212> TYPE: RNA
<213> ORGANISM: Artificial Sequence
<220> FEATURE:
<223> OTHER INFORMATION: Synthetic

<400> SEQUENCE: 51
augaucagau auucuauagu u                                              21

<210> SEQ ID NO 52
<211> LENGTH: 21
<212> TYPE: RNA
<213> ORGANISM: Artificial Sequence
<220> FEATURE:
<223> OTHER INFORMATION: Synthetic

<400> SEQUENCE: 52
cuauagaaua ucgaucauu u                                               21

<210> SEQ ID NO 53
<211> LENGTH: 21
<212> TYPE: RNA
<213> ORGANISM: Artificial Sequence
<220> FEATURE:
<223> OTHER INFORMATION: Synthetic

<400> SEQUENCE: 53
ugaucagaua uucuauagau u                                              21

<210> SEQ ID NO 54
<211> LENGTH: 21
<212> TYPE: RNA
<213> ORGANISM: Artificial Sequence
<220> FEATURE:
<223> OTHER INFORMATION: Synthetic

<400> SEQUENCE: 54
ucuauagaau aucgaucau u                                               21

<210> SEQ ID NO 55
<211> LENGTH: 21
<212> TYPE: RNA
<213> ORGANISM: Artificial Sequence
<220> FEATURE:
<223> OTHER INFORMATION: Synthetic

<400> SEQUENCE: 55
gaucagauau ucuauagagu u                                              21

<210> SEQ ID NO 56
<211> LENGTH: 21
<212> TYPE: RNA
<213> ORGANISM: Artificial Sequence
<220> FEATURE:
<223> OTHER INFORMATION: Synthetic

<400> SEQUENCE: 56
cucuauagaa uaucgaucu u                                               21
```

<210> SEQ ID NO 57
<211> LENGTH: 21
<212> TYPE: RNA
<213> ORGANISM: Artificial Sequence
<220> FEATURE:
<223> OTHER INFORMATION: Synthetic

<400> SEQUENCE: 57
cccaaaucaa gugcaaagau u                                              21

<210> SEQ ID NO 58
<211> LENGTH: 21
<212> TYPE: RNA
<213> ORGANISM: Artificial Sequence
<220> FEATURE:
<223> OTHER INFORMATION: Synthetic

<400> SEQUENCE: 58
ucuuugcacu ugauuugggu u                                              21

<210> SEQ ID NO 59
<211> LENGTH: 21
<212> TYPE: RNA
<213> ORGANISM: Artificial Sequence
<220> FEATURE:
<223> OTHER INFORMATION: Synthetic

<400> SEQUENCE: 59
ccaaaucaag ugcaaagacu u                                              21

<210> SEQ ID NO 60
<211> LENGTH: 21
<212> TYPE: RNA
<213> ORGANISM: Artificial Sequence
<220> FEATURE:
<223> OTHER INFORMATION: Synthetic

<400> SEQUENCE: 60
gucuuugcac uugauuuggu u                                              21

<210> SEQ ID NO 61
<211> LENGTH: 21
<212> TYPE: RNA
<213> ORGANISM: Artificial Sequence
<220> FEATURE:
<223> OTHER INFORMATION: Synthetic

<400> SEQUENCE: 61
caaaucaagu gcaaagacuu u                                              21

<210> SEQ ID NO 62
<211> LENGTH: 21
<212> TYPE: RNA
<213> ORGANISM: Artificial Sequence
<220> FEATURE:
<223> OTHER INFORMATION: Synthetic

<400> SEQUENCE: 62
agucuuugca cuugauuugu u                                              21

<210> SEQ ID NO 63
<211> LENGTH: 21
<212> TYPE: RNA
<213> ORGANISM: Artificial Sequence
<220> FEATURE:

<223> OTHER INFORMATION: Synthetic

<400> SEQUENCE: 63
aaaucaagug caaagacugu u                                        21

<210> SEQ ID NO 64
<211> LENGTH: 21
<212> TYPE: RNA
<213> ORGANISM: Artificial Sequence
<220> FEATURE:
<223> OTHER INFORMATION: Synthetic

<400> SEQUENCE: 64
cagucuuugc acuugauuuu u                                        21

<210> SEQ ID NO 65
<211> LENGTH: 21
<212> TYPE: RNA
<213> ORGANISM: Artificial Sequence
<220> FEATURE:
<223> OTHER INFORMATION: Synthetic

<400> SEQUENCE: 65
aaucaagugc aaagacuguu u                                        21

<210> SEQ ID NO 66
<211> LENGTH: 21
<212> TYPE: RNA
<213> ORGANISM: Artificial Sequence
<220> FEATURE:
<223> OTHER INFORMATION: Synthetic

<400> SEQUENCE: 66
acagucuuug cacuugauuu u                                        21

<210> SEQ ID NO 67
<211> LENGTH: 21
<212> TYPE: RNA
<213> ORGANISM: Artificial Sequence
<220> FEATURE:
<223> OTHER INFORMATION: Synthetic

<400> SEQUENCE: 67
aucaagugca aagacugugu u                                        21

<210> SEQ ID NO 68
<211> LENGTH: 21
<212> TYPE: RNA
<213> ORGANISM: Artificial Sequence
<220> FEATURE:
<223> OTHER INFORMATION: Synthetic

<400> SEQUENCE: 68
cacagucuuu gcacuugauu u                                        21

<210> SEQ ID NO 69
<211> LENGTH: 21
<212> TYPE: RNA
<213> ORGANISM: Artificial Sequence
<220> FEATURE:
<223> OTHER INFORMATION: Synthetic

<400> SEQUENCE: 69
ucaagugcaa agacuguggu u                                        21

```
<210> SEQ ID NO 70
<211> LENGTH: 21
<212> TYPE: RNA
<213> ORGANISM: Artificial Sequence
<220> FEATURE:
<223> OTHER INFORMATION: Synthetic

<400> SEQUENCE: 70
ccacagucuu ugcacuugau u                                              21

<210> SEQ ID NO 71
<211> LENGTH: 21
<212> TYPE: RNA
<213> ORGANISM: Artificial Sequence
<220> FEATURE:
<223> OTHER INFORMATION: Synthetic

<400> SEQUENCE: 71
caagugcaaa gacuguggau u                                              21

<210> SEQ ID NO 72
<211> LENGTH: 21
<212> TYPE: RNA
<213> ORGANISM: Artificial Sequence
<220> FEATURE:
<223> OTHER INFORMATION: Synthetic

<400> SEQUENCE: 72
uccacagucu uugcacuugu u                                              21

<210> SEQ ID NO 73
<211> LENGTH: 21
<212> TYPE: RNA
<213> ORGANISM: Artificial Sequence
<220> FEATURE:
<223> OTHER INFORMATION: Synthetic

<400> SEQUENCE: 73
aagugcaaag acuguggacu u                                              21

<210> SEQ ID NO 74
<211> LENGTH: 21
<212> TYPE: RNA
<213> ORGANISM: Artificial Sequence
<220> FEATURE:
<223> OTHER INFORMATION: Synthetic

<400> SEQUENCE: 74
guccacaguc uuugcacuuu u                                              21

<210> SEQ ID NO 75
<211> LENGTH: 21
<212> TYPE: RNA
<213> ORGANISM: Artificial Sequence
<220> FEATURE:
<223> OTHER INFORMATION: Synthetic

<400> SEQUENCE: 75
agugcaaaga cuguggacau u                                              21

<210> SEQ ID NO 76
<211> LENGTH: 21
<212> TYPE: RNA
<213> ORGANISM: Artificial Sequence
<220> FEATURE:
<223> OTHER INFORMATION: Synthetic
```

```
<400> SEQUENCE: 76
uguccacagu cuuugcacuu u                                              21

<210> SEQ ID NO 77
<211> LENGTH: 21
<212> TYPE: RNA
<213> ORGANISM: Artificial Sequence
<220> FEATURE:
<223> OTHER INFORMATION: Synthetic

<400> SEQUENCE: 77
ugcaaagacu guggacaaau u                                              21

<210> SEQ ID NO 78
<211> LENGTH: 21
<212> TYPE: RNA
<213> ORGANISM: Artificial Sequence
<220> FEATURE:
<223> OTHER INFORMATION: Synthetic

<400> SEQUENCE: 78
uuuguccaca gucuuugcau u                                              21

<210> SEQ ID NO 79
<211> LENGTH: 21
<212> TYPE: RNA
<213> ORGANISM: Artificial Sequence
<220> FEATURE:
<223> OTHER INFORMATION: Synthetic

<400> SEQUENCE: 79
gcaaagacug uggacaaauu u                                              21

<210> SEQ ID NO 80
<211> LENGTH: 21
<212> TYPE: RNA
<213> ORGANISM: Artificial Sequence
<220> FEATURE:
<223> OTHER INFORMATION: Synthetic

<400> SEQUENCE: 80
auuuguccac agucuuugcu u                                              21

<210> SEQ ID NO 81
<211> LENGTH: 21
<212> TYPE: RNA
<213> ORGANISM: Artificial Sequence
<220> FEATURE:
<223> OTHER INFORMATION: Synthetic

<400> SEQUENCE: 81
caaagacugu ggacaaaugu u                                              21

<210> SEQ ID NO 82
<211> LENGTH: 21
<212> TYPE: RNA
<213> ORGANISM: Artificial Sequence
<220> FEATURE:
<223> OTHER INFORMATION: Synthetic

<400> SEQUENCE: 82
cauuugucca cagucuuugu u                                              21

<210> SEQ ID NO 83
<211> LENGTH: 21
```

```
<212> TYPE: RNA
<213> ORGANISM: Artificial Sequence
<220> FEATURE:
<223> OTHER INFORMATION: Synthetic

<400> SEQUENCE: 83
aaagacugug gacaaauguu u                                              21

<210> SEQ ID NO 84
<211> LENGTH: 21
<212> TYPE: RNA
<213> ORGANISM: Artificial Sequence
<220> FEATURE:
<223> OTHER INFORMATION: Synthetic

<400> SEQUENCE: 84
acauuugucc acagucuuuu u                                              21

<210> SEQ ID NO 85
<211> LENGTH: 21
<212> TYPE: RNA
<213> ORGANISM: Artificial Sequence
<220> FEATURE:
<223> OTHER INFORMATION: Synthetic

<400> SEQUENCE: 85
aagacugugg acaaauguuu u                                              21

<210> SEQ ID NO 86
<211> LENGTH: 21
<212> TYPE: RNA
<213> ORGANISM: Artificial Sequence
<220> FEATURE:
<223> OTHER INFORMATION: Synthetic

<400> SEQUENCE: 86
aacauuuguc cacagucuuu u                                              21

<210> SEQ ID NO 87
<211> LENGTH: 21
<212> TYPE: RNA
<213> ORGANISM: Artificial Sequence
<220> FEATURE:
<223> OTHER INFORMATION: Synthetic

<400> SEQUENCE: 87
agacugugga caaauguucu u                                              21

<210> SEQ ID NO 88
<211> LENGTH: 21
<212> TYPE: RNA
<213> ORGANISM: Artificial Sequence
<220> FEATURE:
<223> OTHER INFORMATION: Synthetic

<400> SEQUENCE: 88
gaacauuugu ccacagucuu u                                              21

<210> SEQ ID NO 89
<211> LENGTH: 21
<212> TYPE: RNA
<213> ORGANISM: Artificial Sequence
<220> FEATURE:
<223> OTHER INFORMATION: Synthetic

<400> SEQUENCE: 89
```
gacuguggac aaauguucau u                                                    21

<210> SEQ ID NO 90
<211> LENGTH: 21
<212> TYPE: RNA
<213> ORGANISM: Artificial Sequence
<220> FEATURE:
<223> OTHER INFORMATION: Synthetic

<400> SEQUENCE: 90
ugaacauuug uccacagucu u                                                    21

<210> SEQ ID NO 91
<211> LENGTH: 21
<212> TYPE: RNA
<213> ORGANISM: Artificial Sequence
<220> FEATURE:
<223> OTHER INFORMATION: Synthetic

<400> SEQUENCE: 91
acuguggaca aauguucagu u                                                    21

<210> SEQ ID NO 92
<211> LENGTH: 21
<212> TYPE: RNA
<213> ORGANISM: Artificial Sequence
<220> FEATURE:
<223> OTHER INFORMATION: Synthetic

<400> SEQUENCE: 92
cugaacauuu guccacaguu u                                                    21

<210> SEQ ID NO 93
<211> LENGTH: 21
<212> TYPE: RNA
<213> ORGANISM: Artificial Sequence
<220> FEATURE:
<223> OTHER INFORMATION: Synthetic

<400> SEQUENCE: 93
cuguggacaa auguucagcu u                                                    21

<210> SEQ ID NO 94
<211> LENGTH: 21
<212> TYPE: RNA
<213> ORGANISM: Artificial Sequence
<220> FEATURE:
<223> OTHER INFORMATION: Synthetic

<400> SEQUENCE: 94
gcugaacauu uguccacagu u                                                    21

<210> SEQ ID NO 95
<211> LENGTH: 21
<212> TYPE: RNA
<213> ORGANISM: Artificial Sequence
<220> FEATURE:
<223> OTHER INFORMATION: Synthetic

<400> SEQUENCE: 95
uguggacaaa uguucagcau u                                                    21

<210> SEQ ID NO 96
<211> LENGTH: 21
<212> TYPE: RNA
<213> ORGANISM: Artificial Sequence

```
<220> FEATURE:
<223> OTHER INFORMATION: Synthetic

<400> SEQUENCE: 96
ugcugaacau uuguccacau u                                              21

<210> SEQ ID NO 97
<211> LENGTH: 21
<212> TYPE: RNA
<213> ORGANISM: Artificial Sequence
<220> FEATURE:
<223> OTHER INFORMATION: Synthetic

<400> SEQUENCE: 97
guggacaaau guucagcacu u                                              21

<210> SEQ ID NO 98
<211> LENGTH: 21
<212> TYPE: RNA
<213> ORGANISM: Artificial Sequence
<220> FEATURE:
<223> OTHER INFORMATION: Synthetic

<400> SEQUENCE: 98
gugcugaaca uuuguccacu u                                              21

<210> SEQ ID NO 99
<211> LENGTH: 21
<212> TYPE: RNA
<213> ORGANISM: Artificial Sequence
<220> FEATURE:
<223> OTHER INFORMATION: Synthetic

<400> SEQUENCE: 99
uggacaaaug uucagcacuu u                                              21

<210> SEQ ID NO 100
<211> LENGTH: 21
<212> TYPE: RNA
<213> ORGANISM: Artificial Sequence
<220> FEATURE:
<223> OTHER INFORMATION: Synthetic

<400> SEQUENCE: 100
agugcugaac auuuguccau u                                              21

<210> SEQ ID NO 101
<211> LENGTH: 21
<212> TYPE: RNA
<213> ORGANISM: Artificial Sequence
<220> FEATURE:
<223> OTHER INFORMATION: Synthetic

<400> SEQUENCE: 101
gacaaauguu cagcacuacu u                                              21

<210> SEQ ID NO 102
<211> LENGTH: 21
<212> TYPE: RNA
<213> ORGANISM: Artificial Sequence
<220> FEATURE:
<223> OTHER INFORMATION: Synthetic

<400> SEQUENCE: 102
guagugcuga acauuugucu u                                              21
```

```
<210> SEQ ID NO 103
<211> LENGTH: 21
<212> TYPE: RNA
<213> ORGANISM: Artificial Sequence
<220> FEATURE:
<223> OTHER INFORMATION: Synthetic

<400> SEQUENCE: 103
acaaauguuc agcacuacgu u                                              21

<210> SEQ ID NO 104
<211> LENGTH: 21
<212> TYPE: RNA
<213> ORGANISM: Artificial Sequence
<220> FEATURE:
<223> OTHER INFORMATION: Synthetic

<400> SEQUENCE: 104
cguagugcug aacauuuguu u                                              21

<210> SEQ ID NO 105
<211> LENGTH: 21
<212> TYPE: RNA
<213> ORGANISM: Artificial Sequence
<220> FEATURE:
<223> OTHER INFORMATION: Synthetic

<400> SEQUENCE: 105
caaauguuca gcacuacguu u                                              21

<210> SEQ ID NO 106
<211> LENGTH: 21
<212> TYPE: RNA
<213> ORGANISM: Artificial Sequence
<220> FEATURE:
<223> OTHER INFORMATION: Synthetic

<400> SEQUENCE: 106
acguagugcu gaacauuugu u                                              21

<210> SEQ ID NO 107
<211> LENGTH: 21
<212> TYPE: RNA
<213> ORGANISM: Artificial Sequence
<220> FEATURE:
<223> OTHER INFORMATION: Synthetic

<400> SEQUENCE: 107
aaauguucag cacuacgucu u                                              21

<210> SEQ ID NO 108
<211> LENGTH: 21
<212> TYPE: RNA
<213> ORGANISM: Artificial Sequence
<220> FEATURE:
<223> OTHER INFORMATION: Synthetic

<400> SEQUENCE: 108
gacguagugc ugaacauuuu u                                              21

<210> SEQ ID NO 109
<211> LENGTH: 21
<212> TYPE: RNA
<213> ORGANISM: Artificial Sequence
<220> FEATURE:
<223> OTHER INFORMATION: Synthetic
```

```
<400> SEQUENCE: 109
aauguucagc acuacgucuu u                                          21

<210> SEQ ID NO 110
<211> LENGTH: 21
<212> TYPE: RNA
<213> ORGANISM: Artificial Sequence
<220> FEATURE:
<223> OTHER INFORMATION: Synthetic

<400> SEQUENCE: 110
agacguagug cugaacauuu u                                          21

<210> SEQ ID NO 111
<211> LENGTH: 21
<212> TYPE: RNA
<213> ORGANISM: Artificial Sequence
<220> FEATURE:
<223> OTHER INFORMATION: Synthetic

<400> SEQUENCE: 111
auguucagca cuacgucuuu u                                          21

<210> SEQ ID NO 112
<211> LENGTH: 21
<212> TYPE: RNA
<213> ORGANISM: Artificial Sequence
<220> FEATURE:
<223> OTHER INFORMATION: Synthetic

<400> SEQUENCE: 112
aagacguagu gcugaacauu u                                          21

<210> SEQ ID NO 113
<211> LENGTH: 21
<212> TYPE: RNA
<213> ORGANISM: Artificial Sequence
<220> FEATURE:
<223> OTHER INFORMATION: Synthetic

<400> SEQUENCE: 113
uguucagcac uacgucuucu u                                          21

<210> SEQ ID NO 114
<211> LENGTH: 21
<212> TYPE: RNA
<213> ORGANISM: Artificial Sequence
<220> FEATURE:
<223> OTHER INFORMATION: Synthetic

<400> SEQUENCE: 114
gaagacguag ugcugaacau u                                          21

<210> SEQ ID NO 115
<211> LENGTH: 21
<212> TYPE: RNA
<213> ORGANISM: Artificial Sequence
<220> FEATURE:
<223> OTHER INFORMATION: Synthetic

<400> SEQUENCE: 115
guucagcacu acgucuuccu u                                          21

<210> SEQ ID NO 116
```

```
<211> LENGTH: 21
<212> TYPE: RNA
<213> ORGANISM: Artificial Sequence
<220> FEATURE:
<223> OTHER INFORMATION: Synthetic

<400> SEQUENCE: 116
ggaagacgua gugcugaacu u                                              21

<210> SEQ ID NO 117
<211> LENGTH: 21
<212> TYPE: RNA
<213> ORGANISM: Artificial Sequence
<220> FEATURE:
<223> OTHER INFORMATION: Synthetic

<400> SEQUENCE: 117
uucagcacua cgucuuccuu u                                              21

<210> SEQ ID NO 118
<211> LENGTH: 21
<212> TYPE: RNA
<213> ORGANISM: Artificial Sequence
<220> FEATURE:
<223> OTHER INFORMATION: Synthetic

<400> SEQUENCE: 118
aggaagacgu agugcugaau u                                              21

<210> SEQ ID NO 119
<211> LENGTH: 21
<212> TYPE: RNA
<213> ORGANISM: Artificial Sequence
<220> FEATURE:
<223> OTHER INFORMATION: Synthetic

<400> SEQUENCE: 119
ucagcacuac gucuuccuuu u                                              21

<210> SEQ ID NO 120
<211> LENGTH: 21
<212> TYPE: RNA
<213> ORGANISM: Artificial Sequence
<220> FEATURE:
<223> OTHER INFORMATION: Synthetic

<400> SEQUENCE: 120
aaggaagacg uagugcugau u                                              21

<210> SEQ ID NO 121
<211> LENGTH: 21
<212> TYPE: RNA
<213> ORGANISM: Artificial Sequence
<220> FEATURE:
<223> OTHER INFORMATION: Synthetic

<400> SEQUENCE: 121
caaucuccca ggaauguggu u                                              21

<210> SEQ ID NO 122
<211> LENGTH: 21
<212> TYPE: RNA
<213> ORGANISM: Artificial Sequence
<220> FEATURE:
<223> OTHER INFORMATION: Synthetic

<400> SEQUENCE: 122
```
ccacauuccu gggagauugu u                                              21

<210> SEQ ID NO 123
<211> LENGTH: 21
<212> TYPE: RNA
<213> ORGANISM: Artificial Sequence
<220> FEATURE:
<223> OTHER INFORMATION: Synthetic

<400> SEQUENCE: 123
aaucucccag gaauguggau u                                              21

<210> SEQ ID NO 124
<211> LENGTH: 21
<212> TYPE: RNA
<213> ORGANISM: Artificial Sequence
<220> FEATURE:
<223> OTHER INFORMATION: Synthetic

<400> SEQUENCE: 124
uccacauucc ugggagauuu u                                              21

<210> SEQ ID NO 125
<211> LENGTH: 21
<212> TYPE: RNA
<213> ORGANISM: Artificial Sequence
<220> FEATURE:
<223> OTHER INFORMATION: Synthetic

<400> SEQUENCE: 125
aucucccagg aauguggagu u                                              21

<210> SEQ ID NO 126
<211> LENGTH: 21
<212> TYPE: RNA
<213> ORGANISM: Artificial Sequence
<220> FEATURE:
<223> OTHER INFORMATION: Synthetic

<400> SEQUENCE: 126
cuccacauuc cugggagauu u                                              21

<210> SEQ ID NO 127
<211> LENGTH: 21
<212> TYPE: RNA
<213> ORGANISM: Artificial Sequence
<220> FEATURE:
<223> OTHER INFORMATION: Synthetic

<400> SEQUENCE: 127
ucucccagga auguggaggu u                                              21

<210> SEQ ID NO 128
<211> LENGTH: 21
<212> TYPE: RNA
<213> ORGANISM: Artificial Sequence
<220> FEATURE:
<223> OTHER INFORMATION: Synthetic

<400> SEQUENCE: 128
ccuccacauu ccugggagau u                                              21

<210> SEQ ID NO 129
<211> LENGTH: 21
<212> TYPE: RNA

```
<213> ORGANISM: Artificial Sequence
<220> FEATURE:
<223> OTHER INFORMATION: Synthetic

<400> SEQUENCE: 129
cucccaggaa uguggaggau u                                              21

<210> SEQ ID NO 130
<211> LENGTH: 21
<212> TYPE: RNA
<213> ORGANISM: Artificial Sequence
<220> FEATURE:
<223> OTHER INFORMATION: Synthetic

<400> SEQUENCE: 130
uccuccacau uccugggagu u                                              21

<210> SEQ ID NO 131
<211> LENGTH: 21
<212> TYPE: RNA
<213> ORGANISM: Artificial Sequence
<220> FEATURE:
<223> OTHER INFORMATION: Synthetic

<400> SEQUENCE: 131
ucccaggaau guggaggagu u                                              21

<210> SEQ ID NO 132
<211> LENGTH: 21
<212> TYPE: RNA
<213> ORGANISM: Artificial Sequence
<220> FEATURE:
<223> OTHER INFORMATION: Synthetic

<400> SEQUENCE: 132
cuccuccaca uuccuggau u                                               21

<210> SEQ ID NO 133
<211> LENGTH: 21
<212> TYPE: RNA
<213> ORGANISM: Artificial Sequence
<220> FEATURE:
<223> OTHER INFORMATION: Synthetic

<400> SEQUENCE: 133
cccaggaaug uggaggagau u                                              21

<210> SEQ ID NO 134
<211> LENGTH: 21
<212> TYPE: RNA
<213> ORGANISM: Artificial Sequence
<220> FEATURE:
<223> OTHER INFORMATION: Synthetic

<400> SEQUENCE: 134
ucuccuccac auuccugggu u                                              21

<210> SEQ ID NO 135
<211> LENGTH: 21
<212> TYPE: RNA
<213> ORGANISM: Artificial Sequence
<220> FEATURE:
<223> OTHER INFORMATION: Synthetic

<400> SEQUENCE: 135
ccaggaaugu ggaggagagu u                                              21
```

<210> SEQ ID NO 136
<211> LENGTH: 21
<212> TYPE: RNA
<213> ORGANISM: Artificial Sequence
<220> FEATURE:
<223> OTHER INFORMATION: Synthetic

<400> SEQUENCE: 136
cucuccucca cauuccuggu u					21

<210> SEQ ID NO 137
<211> LENGTH: 21
<212> TYPE: RNA
<213> ORGANISM: Artificial Sequence
<220> FEATURE:
<223> OTHER INFORMATION: Synthetic

<400> SEQUENCE: 137
caggaaugug gaggagagau u					21

<210> SEQ ID NO 138
<211> LENGTH: 21
<212> TYPE: RNA
<213> ORGANISM: Artificial Sequence
<220> FEATURE:
<223> OTHER INFORMATION: Synthetic

<400> SEQUENCE: 138
ucucuccucc acauuccugu u					21

<210> SEQ ID NO 139
<211> LENGTH: 21
<212> TYPE: RNA
<213> ORGANISM: Artificial Sequence
<220> FEATURE:
<223> OTHER INFORMATION: Synthetic

<400> SEQUENCE: 139
aggaaugugg aggagagaau u					21

<210> SEQ ID NO 140
<211> LENGTH: 21
<212> TYPE: RNA
<213> ORGANISM: Artificial Sequence
<220> FEATURE:
<223> OTHER INFORMATION: Synthetic

<400> SEQUENCE: 140
uucucuccuc cacauuccuu u					21

<210> SEQ ID NO 141
<211> LENGTH: 21
<212> TYPE: RNA
<213> ORGANISM: Artificial Sequence
<220> FEATURE:
<223> OTHER INFORMATION: Synthetic

<400> SEQUENCE: 141
gaauguggag gagagaaugu u					21

<210> SEQ ID NO 142
<211> LENGTH: 21
<212> TYPE: RNA
<213> ORGANISM: Artificial Sequence
<220> FEATURE:

<223> OTHER INFORMATION: Synthetic

<400> SEQUENCE: 142
cauucucucc uccacauucu u                                              21

<210> SEQ ID NO 143
<211> LENGTH: 21
<212> TYPE: RNA
<213> ORGANISM: Artificial Sequence
<220> FEATURE:
<223> OTHER INFORMATION: Synthetic

<400> SEQUENCE: 143
aauguggagg agagaaugau u                                              21

<210> SEQ ID NO 144
<211> LENGTH: 21
<212> TYPE: RNA
<213> ORGANISM: Artificial Sequence
<220> FEATURE:
<223> OTHER INFORMATION: Synthetic

<400> SEQUENCE: 144
ucauucucuc cuccacauuu u                                              21

<210> SEQ ID NO 145
<211> LENGTH: 21
<212> TYPE: RNA
<213> ORGANISM: Artificial Sequence
<220> FEATURE:
<223> OTHER INFORMATION: Synthetic

<400> SEQUENCE: 145
auguggagga gagaaugaau u                                              21

<210> SEQ ID NO 146
<211> LENGTH: 21
<212> TYPE: RNA
<213> ORGANISM: Artificial Sequence
<220> FEATURE:
<223> OTHER INFORMATION: Synthetic

<400> SEQUENCE: 146
uucauucucu ccuccacauu u                                              21

<210> SEQ ID NO 147
<211> LENGTH: 21
<212> TYPE: RNA
<213> ORGANISM: Artificial Sequence
<220> FEATURE:
<223> OTHER INFORMATION: Synthetic

<400> SEQUENCE: 147
uguggaggag agaaugaauu u                                              21

<210> SEQ ID NO 148
<211> LENGTH: 21
<212> TYPE: RNA
<213> ORGANISM: Artificial Sequence
<220> FEATURE:
<223> OTHER INFORMATION: Synthetic

<400> SEQUENCE: 148
auucauucuc uccuccacau u                                              21

```
<210> SEQ ID NO 149
<211> LENGTH: 21
<212> TYPE: RNA
<213> ORGANISM: Artificial Sequence
<220> FEATURE:
<223> OTHER INFORMATION: Synthetic

<400> SEQUENCE: 149
guggaggaga gaaugaaugu u                                              21

<210> SEQ ID NO 150
<211> LENGTH: 21
<212> TYPE: RNA
<213> ORGANISM: Artificial Sequence
<220> FEATURE:
<223> OTHER INFORMATION: Synthetic

<400> SEQUENCE: 150
cauucauucu cuccuccacu u                                              21

<210> SEQ ID NO 151
<211> LENGTH: 21
<212> TYPE: RNA
<213> ORGANISM: Artificial Sequence
<220> FEATURE:
<223> OTHER INFORMATION: Synthetic

<400> SEQUENCE: 151
uggaggagag aaugaauggu u                                              21

<210> SEQ ID NO 152
<211> LENGTH: 21
<212> TYPE: RNA
<213> ORGANISM: Artificial Sequence
<220> FEATURE:
<223> OTHER INFORMATION: Synthetic

<400> SEQUENCE: 152
ccauucauuc ucuccuccau u                                              21

<210> SEQ ID NO 153
<211> LENGTH: 21
<212> TYPE: RNA
<213> ORGANISM: Artificial Sequence
<220> FEATURE:
<223> OTHER INFORMATION: Synthetic

<400> SEQUENCE: 153
ggaggagaga augaauggcu u                                              21

<210> SEQ ID NO 154
<211> LENGTH: 21
<212> TYPE: RNA
<213> ORGANISM: Artificial Sequence
<220> FEATURE:
<223> OTHER INFORMATION: Synthetic

<400> SEQUENCE: 154
gccauucauu cucuccuccu u                                              21

<210> SEQ ID NO 155
<211> LENGTH: 21
<212> TYPE: RNA
<213> ORGANISM: Artificial Sequence
<220> FEATURE:
<223> OTHER INFORMATION: Synthetic
```

<400> SEQUENCE: 155
gaggagagaa ugaauggcau u                                              21

<210> SEQ ID NO 156
<211> LENGTH: 21
<212> TYPE: RNA
<213> ORGANISM: Artificial Sequence
<220> FEATURE:
<223> OTHER INFORMATION: Synthetic

<400> SEQUENCE: 156
ugccauucau ucucuccucu u                                              21

<210> SEQ ID NO 157
<211> LENGTH: 21
<212> TYPE: RNA
<213> ORGANISM: Artificial Sequence
<220> FEATURE:
<223> OTHER INFORMATION: Synthetic

<400> SEQUENCE: 157
aggagagaau gaauggcagu u                                              21

<210> SEQ ID NO 158
<211> LENGTH: 21
<212> TYPE: RNA
<213> ORGANISM: Artificial Sequence
<220> FEATURE:
<223> OTHER INFORMATION: Synthetic

<400> SEQUENCE: 158
cugccauuca uucucuccuu u                                              21

<210> SEQ ID NO 159
<211> LENGTH: 21
<212> TYPE: RNA
<213> ORGANISM: Artificial Sequence
<220> FEATURE:
<223> OTHER INFORMATION: Synthetic

<400> SEQUENCE: 159
ggagagaaug aauggcaguu u                                              21

<210> SEQ ID NO 160
<211> LENGTH: 21
<212> TYPE: RNA
<213> ORGANISM: Artificial Sequence
<220> FEATURE:
<223> OTHER INFORMATION: Synthetic

<400> SEQUENCE: 160
acugccauuc auucucuccu u                                              21

<210> SEQ ID NO 161
<211> LENGTH: 21
<212> TYPE: RNA
<213> ORGANISM: Artificial Sequence
<220> FEATURE:
<223> OTHER INFORMATION: Synthetic

<400> SEQUENCE: 161
uugcuggaug augaagaagu u                                              21

<210> SEQ ID NO 162
<211> LENGTH: 21

-continued

```
<212> TYPE: RNA
<213> ORGANISM: Artificial Sequence
<220> FEATURE:
<223> OTHER INFORMATION: Synthetic

<400> SEQUENCE: 162
cuucuucauc auccagcaau u                                              21

<210> SEQ ID NO 163
<211> LENGTH: 21
<212> TYPE: RNA
<213> ORGANISM: Artificial Sequence
<220> FEATURE:
<223> OTHER INFORMATION: Synthetic

<400> SEQUENCE: 163
ugcuggauga ugaagaaguu u                                              21

<210> SEQ ID NO 164
<211> LENGTH: 21
<212> TYPE: RNA
<213> ORGANISM: Artificial Sequence
<220> FEATURE:
<223> OTHER INFORMATION: Synthetic

<400> SEQUENCE: 164
acuucuucau cauccagcau u                                              21

<210> SEQ ID NO 165
<211> LENGTH: 21
<212> TYPE: RNA
<213> ORGANISM: Artificial Sequence
<220> FEATURE:
<223> OTHER INFORMATION: Synthetic

<400> SEQUENCE: 165
gcuggaugau gaagaaguuu u                                              21

<210> SEQ ID NO 166
<211> LENGTH: 21
<212> TYPE: RNA
<213> ORGANISM: Artificial Sequence
<220> FEATURE:
<223> OTHER INFORMATION: Synthetic

<400> SEQUENCE: 166
aacuucuuca ucauccagcu u                                              21

<210> SEQ ID NO 167
<211> LENGTH: 21
<212> TYPE: RNA
<213> ORGANISM: Artificial Sequence
<220> FEATURE:
<223> OTHER INFORMATION: Synthetic

<400> SEQUENCE: 167
cuggaugaug aagaaguugu u                                              21

<210> SEQ ID NO 168
<211> LENGTH: 21
<212> TYPE: RNA
<213> ORGANISM: Artificial Sequence
<220> FEATURE:
<223> OTHER INFORMATION: Synthetic

<400> SEQUENCE: 168
```
caacuucuuc aucauccagu u                                              21

<210> SEQ ID NO 169
<211> LENGTH: 21
<212> TYPE: RNA
<213> ORGANISM: Artificial Sequence
<220> FEATURE:
<223> OTHER INFORMATION: Synthetic

<400> SEQUENCE: 169
uggaugauga agaaguugau u                                              21

<210> SEQ ID NO 170
<211> LENGTH: 21
<212> TYPE: RNA
<213> ORGANISM: Artificial Sequence
<220> FEATURE:
<223> OTHER INFORMATION: Synthetic

<400> SEQUENCE: 170
ucaacuucuu caucauccau u                                              21

<210> SEQ ID NO 171
<211> LENGTH: 21
<212> TYPE: RNA
<213> ORGANISM: Artificial Sequence
<220> FEATURE:
<223> OTHER INFORMATION: Synthetic

<400> SEQUENCE: 171
ggaugaugaa gaaguugaau u                                              21

<210> SEQ ID NO 172
<211> LENGTH: 21
<212> TYPE: RNA
<213> ORGANISM: Artificial Sequence
<220> FEATURE:
<223> OTHER INFORMATION: Synthetic

<400> SEQUENCE: 172
uucaacuucu ucaucauccu u                                              21

<210> SEQ ID NO 173
<211> LENGTH: 21
<212> TYPE: RNA
<213> ORGANISM: Artificial Sequence
<220> FEATURE:
<223> OTHER INFORMATION: Synthetic

<400> SEQUENCE: 173
gaugaugaag aaguugaagu u                                              21

<210> SEQ ID NO 174
<211> LENGTH: 21
<212> TYPE: RNA
<213> ORGANISM: Artificial Sequence
<220> FEATURE:
<223> OTHER INFORMATION: Synthetic

<400> SEQUENCE: 174
cuucaacuuc uucaucaucu u                                              21

<210> SEQ ID NO 175
<211> LENGTH: 21
<212> TYPE: RNA
<213> ORGANISM: Artificial Sequence

```
<220> FEATURE:
<223> OTHER INFORMATION: Synthetic

<400> SEQUENCE: 175
augaugaaga aguugaagau u                                              21

<210> SEQ ID NO 176
<211> LENGTH: 21
<212> TYPE: RNA
<213> ORGANISM: Artificial Sequence
<220> FEATURE:
<223> OTHER INFORMATION: Synthetic

<400> SEQUENCE: 176
ucuucaacuu cuucaucauu u                                              21

<210> SEQ ID NO 177
<211> LENGTH: 21
<212> TYPE: RNA
<213> ORGANISM: Artificial Sequence
<220> FEATURE:
<223> OTHER INFORMATION: Synthetic

<400> SEQUENCE: 177
ugaugaagaa guugaagauu u                                              21

<210> SEQ ID NO 178
<211> LENGTH: 21
<212> TYPE: RNA
<213> ORGANISM: Artificial Sequence
<220> FEATURE:
<223> OTHER INFORMATION: Synthetic

<400> SEQUENCE: 178
aucuucaacu ucuucaucau u                                              21

<210> SEQ ID NO 179
<211> LENGTH: 21
<212> TYPE: RNA
<213> ORGANISM: Artificial Sequence
<220> FEATURE:
<223> OTHER INFORMATION: Synthetic

<400> SEQUENCE: 179
gaugaagaag uugaagaugu u                                              21

<210> SEQ ID NO 180
<211> LENGTH: 21
<212> TYPE: RNA
<213> ORGANISM: Artificial Sequence
<220> FEATURE:
<223> OTHER INFORMATION: Synthetic

<400> SEQUENCE: 180
caucuucaac uucuucaucu u                                              21

<210> SEQ ID NO 181
<211> LENGTH: 21
<212> TYPE: RNA
<213> ORGANISM: Artificial Sequence
<220> FEATURE:
<223> OTHER INFORMATION: Synthetic

<400> SEQUENCE: 181
ugaagaaguu gaagaugagu u                                              21
```

```
<210> SEQ ID NO 182
<211> LENGTH: 21
<212> TYPE: RNA
<213> ORGANISM: Artificial Sequence
<220> FEATURE:
<223> OTHER INFORMATION: Synthetic

<400> SEQUENCE: 182
cucaucuuca acuucuucau u                                              21

<210> SEQ ID NO 183
<211> LENGTH: 21
<212> TYPE: RNA
<213> ORGANISM: Artificial Sequence
<220> FEATURE:
<223> OTHER INFORMATION: Synthetic

<400> SEQUENCE: 183
gaagaaguug aagaugaggu u                                              21

<210> SEQ ID NO 184
<211> LENGTH: 21
<212> TYPE: RNA
<213> ORGANISM: Artificial Sequence
<220> FEATURE:
<223> OTHER INFORMATION: Synthetic

<400> SEQUENCE: 184
ccucaucuuc aacuucuucu u                                              21

<210> SEQ ID NO 185
<211> LENGTH: 21
<212> TYPE: RNA
<213> ORGANISM: Artificial Sequence
<220> FEATURE:
<223> OTHER INFORMATION: Synthetic

<400> SEQUENCE: 185
aagaaguuga agaugagguu u                                              21

<210> SEQ ID NO 186
<211> LENGTH: 21
<212> TYPE: RNA
<213> ORGANISM: Artificial Sequence
<220> FEATURE:
<223> OTHER INFORMATION: Synthetic

<400> SEQUENCE: 186
accucaucuu caacuucuuu u                                              21

<210> SEQ ID NO 187
<211> LENGTH: 21
<212> TYPE: RNA
<213> ORGANISM: Artificial Sequence
<220> FEATURE:
<223> OTHER INFORMATION: Synthetic

<400> SEQUENCE: 187
agaaguugaa gaugaggugu u                                              21

<210> SEQ ID NO 188
<211> LENGTH: 21
<212> TYPE: RNA
<213> ORGANISM: Artificial Sequence
<220> FEATURE:
<223> OTHER INFORMATION: Synthetic
```

```
<400> SEQUENCE: 188
caccucaucu ucaacuucuu u                                              21

<210> SEQ ID NO 189
<211> LENGTH: 21
<212> TYPE: RNA
<213> ORGANISM: Artificial Sequence
<220> FEATURE:
<223> OTHER INFORMATION: Synthetic

<400> SEQUENCE: 189
gaaguugaag augaggguguu u                                             21

<210> SEQ ID NO 190
<211> LENGTH: 21
<212> TYPE: RNA
<213> ORGANISM: Artificial Sequence
<220> FEATURE:
<223> OTHER INFORMATION: Synthetic

<400> SEQUENCE: 190
acaccucauc uucaacuucu u                                              21

<210> SEQ ID NO 191
<211> LENGTH: 21
<212> TYPE: RNA
<213> ORGANISM: Artificial Sequence
<220> FEATURE:
<223> OTHER INFORMATION: Synthetic

<400> SEQUENCE: 191
aaguugaaga ugagguguuu u                                              21

<210> SEQ ID NO 192
<211> LENGTH: 21
<212> TYPE: RNA
<213> ORGANISM: Artificial Sequence
<220> FEATURE:
<223> OTHER INFORMATION: Synthetic

<400> SEQUENCE: 192
aacaccucau cuucaacuuu u                                              21

<210> SEQ ID NO 193
<211> LENGTH: 21
<212> TYPE: RNA
<213> ORGANISM: Artificial Sequence
<220> FEATURE:
<223> OTHER INFORMATION: Synthetic

<400> SEQUENCE: 193
aguugaagau gagguguugu u                                              21

<210> SEQ ID NO 194
<211> LENGTH: 21
<212> TYPE: RNA
<213> ORGANISM: Artificial Sequence
<220> FEATURE:
<223> OTHER INFORMATION: Synthetic

<400> SEQUENCE: 194
caacaccuca ucuucaacuu u                                              21

<210> SEQ ID NO 195
```

```
<211> LENGTH: 21
<212> TYPE: RNA
<213> ORGANISM: Artificial Sequence
<220> FEATURE:
<223> OTHER INFORMATION: Synthetic

<400> SEQUENCE: 195
guugaagaug agguguuguu u                                                21

<210> SEQ ID NO 196
<211> LENGTH: 21
<212> TYPE: RNA
<213> ORGANISM: Artificial Sequence
<220> FEATURE:
<223> OTHER INFORMATION: Synthetic

<400> SEQUENCE: 196
acaacaccuc aucuucaacu u                                                21

<210> SEQ ID NO 197
<211> LENGTH: 21
<212> TYPE: RNA
<213> ORGANISM: Artificial Sequence
<220> FEATURE:
<223> OTHER INFORMATION: Synthetic

<400> SEQUENCE: 197
uugaagauga gguguuguuu u                                                21

<210> SEQ ID NO 198
<211> LENGTH: 21
<212> TYPE: RNA
<213> ORGANISM: Artificial Sequence
<220> FEATURE:
<223> OTHER INFORMATION: Synthetic

<400> SEQUENCE: 198 aacaaccaccu caucuucaau u                                               21

<210> SEQ ID NO 199
<211> LENGTH: 21
<212> TYPE: RNA
<213> ORGANISM: Artificial Sequence
<220> FEATURE:
<223> OTHER INFORMATION: Synthetic

<400> SEQUENCE: 199
ugaagaugag guguuguuau u                                                21

<210> SEQ ID NO 200
<211> LENGTH: 21
<212> TYPE: RNA
<213> ORGANISM: Artificial Sequence
<220> FEATURE:
<223> OTHER INFORMATION: Synthetic

<400> SEQUENCE: 200
uaacaacacc ucaucuucau u                                                21

<210> SEQ ID NO 201
<211> LENGTH: 15
<212> TYPE: DNA
<213> ORGANISM: Artificial Sequence
<220> FEATURE:
<223> OTHER INFORMATION: Synthetic

<400> SEQUENCE: 201
```

```
gayaagayaa gataa                                                    15

<210> SEQ ID NO 202
<211> LENGTH: 9
<212> TYPE: DNA
<213> ORGANISM: Artificial Sequence
<220> FEATURE:
<223> OTHER INFORMATION: Synthetic

<400> SEQUENCE: 202 gaagatgag                                                            9

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
aaggcatgtt cgcaacatcc                                               20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
tagtcatcct cagggtttcc                                               20

<210> SEQ ID NO 205
<211> LENGTH: 23
<212> TYPE: DNA
<213> ORGANISM: Artificial Sequence
<220> FEATURE:
<223> OTHER INFORMATION: Synthetic

<400> SEQUENCE: 205
gggaaatcgt gcgtgacatt aag                                           23

<210> SEQ ID NO 206
<211> LENGTH: 22
<212> TYPE: DNA
<213> ORGANISM: Artificial Sequence
<220> FEATURE:
<223> OTHER INFORMATION: Synthetic

<400> SEQUENCE: 206
tgtgttggcg tacaggtctt tg                                            22
```